(12) United States Patent
Matzuk et al.

(10) Patent No.: US 7,232,678 B2
(45) Date of Patent: Jun. 19, 2007

(54) IDENTIFICATION OF OLIGOADENYLATE SYNTHETASE-LIKE GENES

(75) Inventors: Martin M. Matzuk, Pearland, TX (US); Yuchen Bai, Newtown, PA (US); Wei Yan, Houston, TX (US)

(73) Assignees: Wyeth, Madison, NJ (US); Baylor College of Medicine, Houston, TX (US)

( * ) Notice: Subject to any disclaimer, the term of this patent is extended or adjusted under 35 U.S.C. 154(b) by 391 days.

(21) Appl. No.: 10/439,741

(22) Filed: May 16, 2003

(65) Prior Publication Data

US 2003/0235575 A1 Dec. 25, 2003

Related U.S. Application Data

(60) Provisional application No. 60/381,408, filed on May 17, 2002.

(51) Int. Cl.
*C12N 9/22* (2006.01)
*C12N 15/70* (2006.01)
*C12Q 1/68* (2006.01)
*C12P 21/06* (2006.01)
*C07H 21/04* (2006.01)
*A61K 38/47* (2006.01)

(52) U.S. Cl. .......................... 435/199; 435/6; 435/325; 435/69.1; 435/320.1; 536/23.2; 424/94.61

(58) Field of Classification Search ................ 435/199, 435/6, 69.1, 320.1, 325; 536/23.2; 424/94.61
See application file for complete search history.

(56) References Cited

OTHER PUBLICATIONS

Kakuta et al. GenBank Accession No. BAB84129, 2',5'-oligoadenylate synthetase-like 1 [Mus musculus].*
UniProt Accession No. Q8V195, 2',5'-oligoadenylate synthetase-like 8 (Mus musculus).*
Coccia et al. A full-length murine 2-5A synthetase cDNA transfected in NIH-3T3 cells impairs EMCV but not VSV replication. Virology. Nov. 1990;179(1):228-33.*
Bachvarova et al., "Polyadenylated RNA of Mouse Ova and Loss of Maternal RNA in Early Development," Developmental Biology 714, 1980, pp. 1-8.
Clegg et al., "Poly(A) Length, Cytoplasmic Adenylation and Synthesis of Poly(a)+ RNA in Early Mouse Embryos," Developmental Biology 95, 1983, pp. 331-341.
Huarte et al., "Meiotic Maturation of Mouse Oocytes triggers the Translation and Polyadenylation of Dormant tissue-Type Plasminogen Activator mRNA," Genes & Development 1, 1987, pp. 1201-1211.
Bachvarova et al., "Amounts and Modulation of Actin mRNAs in Mouse Oocytes and Embryos," Development 106, 1989, pp. 561-565.
Perreault, Sally D., "Chromatin Remodeling in Mammalian Zygotes," Mutation Research, 296, 1992, pp. 43-55.

McLay et al., "The Ability to Organize Sperm DNA into Functional Chromatin is Acquired During Meiotic Maturation in Murine Oocytes," Developmental Biology 186, 1997, pp. 73-84.
Eppig et al., "Oocyte Control of Granulosa Cell Development: How and Why," Human Reproduction 12, 1997, pp. 127-132.
Rebouillat et al., "Molecular Cloning and Characterization of Two Related and Interferon-Induced 56-kDa and 30-kDa Proteins Highly Similar to 2'-5' Oligoadenylate Synthetase," Eur. J. Biochem 257, 1998, pp. 319-330.
Latham et al., "Comparison of Protein Synthesis Patterns in Mouse Cumulus Cells and Mural Granulosa Cells: Effects of Follicles-Stimulating Hormone and Insulin on Granulosa Cell Differentiation In Vitro," Biology of Reproduction 61, 1999, pp. 482-492.
Rebouillat et al, "The Human 2', 5' -Oligoadenylate Synthetase Family: Interferon-Induced Proteins with Unique Enzymatic Properties," Journal of Interferon and Cytokine Research 19, 1999, pp. 295-308.
Yamamoto et al., "Effects of Specific Mutations in Active Site Motifs of 2', 5'-Oligoadenylate Synthetase on Enzymatic Activity," Journal of Interferon and Cytokine Research 20, 2000, pp. 337-344.
Shibata et al., "Cloning of a Novel 2',5'-Oligoadenylate Synthetase-like Molecule, OasI5 in Mice," Gene 271, 2001, pp. 261-271.
Rajkovic et al., "Discovery of Germ Cell-Specific Transcripts by Expressed Sequence Tag Database Analysis," Fertility and Sterility vol. 76, No. 3, Sep. 2001, pp. 550-554.
Eskildsen et al., "Gene Structure of the Murine 2'-5'- Oligoadenylate Synthetase Family," Cell Mol. Life Sci. 59, 2002, pp. 1212-1222.
Carpten et al., "Germline Mutations in the Ribonuclease L Gene in Families Showing Linkage with HPC1," Nature Genetics vol. 30, Feb. 2002, pp. 181-184.
Kakuta et al., "Database GENBANK, 29, Database Accession No. AB067532, SEQ ID No. 1 and SEQ ID No. 2," Jan. 29, 2002, 5 pages.
Perelygin, et al."Positional cloning of the murine flavivirus resistance gene," Department of Biology, Georgia State University, Atlanta, Jul. 9, 2002, pp. 9322-9327.
International Search Report issued for PCT/US2003/15453, dated Nov. 22, 2006.
Yaffe, A., et al., "Inhibition of 2-5A synthetase Expression by antisense RNA interferes with Interferon-mediated antiviral and antiproliferative effects and induces anchorage-independent cell growth," Cell Growth & Differentiation, vol. 7, pp. 969-978.
Salzberg, S., et al., "Ectopic expression of 2-5A synthetase in myeloid cells induces growth arrest and facilitates the appearance of a myeloid differentiation marker," Cancer Research, vol. 57, pp. 2732-2740.
Examination Report issued for AU2003299505, dated Apr. 4, 2007.

* cited by examiner

*Primary Examiner*—Ponnathapu Achutamurthy
*Assistant Examiner*—Iqbal Chowdury
(74) *Attorney, Agent, or Firm*—Fulbright & Jaworksi LLP

(57) ABSTRACT

The present invention relates to compositions and methods for modulating conception in animals. More particularly, the composition modulates mRNA degradation during gametogenesis and early development. Yet further, the present invention relates to pharmaceutical compositions and methods for modulating diseases of the reproductive organs, such as hyperproliferative diseases.

4 Claims, 26 Drawing Sheets

```
                                                        OAS1a
                                                        OAS1b
                                                        OAS1c
                                                        OAS4
                                                        OAS5
                                                        OAS6
                                                        OAS7
                                                        OAS11

348  - - - - - - - - - - - - - - - - - - - P T V V P V P F E Q V E E N W T C I L L
348  - - - - - - - - - - - - - - - - - - - P
348  - - - - - - - - - - - - - - - - - - - P T V V P V P F E Q V
446  S K P F T I D P D D T I L D L K E K I E D A G A G G L T
358  - - - - - - - - - - - - - - - - - - - - - - - - E C A F Q
357  - - - - - - - - - - - - - - - - - - - - - - - - E C V F L
356
251
```

Decoration 'Decoration #1': Shade (with solid black) residues that match the Consensus exactly.

IDENTIFICATION OF OLIGOADENYLATE SYNTHETASE-LIKE GENES

This application claims priority to U.S. Provisional Application No. 60/381,408 filed on May 17, 2002, which is incorporated herein by reference.

This invention was made with government support under NIH Grant No. HD42500 awarded by the National Institutes of Health. The United States Government may have certain rights in the invention.

FIELD OF INVENTION

The present invention relates to the field of medicine. More particularly, it relates to pharmaceutical compositions and methods for modulating conception in animals. Yet further, the present invention relates to pharmaceutical compositions and methods for modulating diseases of the reproductive organs, such as hyperproliferative diseases.

BACKGROUND

Viral infection and interferons can induce the expression of 2', 5'-oligoadenylate synthetases (OAS) (Rebouillat et al., 1999). These OAS proteins are expressed "ubiquitously" in humans and mice. In humans, there are three reported OAS genes (small, OAS1; medium, OAS2; and large, OAS3) and one OAS-like gene (OASL) which are linked on human chromosome 12. There are two mouse OAS genes (Oas1A and Oas1B) that arose from a gene duplication and encode "small" OAS proteins, as well as an OAS-like gene (Oasl5). OASL5 protein is 60% identical to mouse OAS1A and 1B (Shibata et al., 2001) but distinct from human OASL. The three human OAS proteins and the mouse OAS proteins, except OASL or OASL5, share the ability to convert ATP into 2', 5'-linked oligomers of adenosine (2–5A) in the presence of double stranded (ds) RNA. GTP can also act as a substrate for OAS, though the in vivo significance of this is not understood. 2–5A oligomers bind and activate RNAse L leading to degradation of viral and cellular RNA and thereby downregulating protein production. However, it is not known if OAS or OAS-like proteins have RNAse L-independent antiviral activities or function in cellular processes unrelated to viral infection (i.e., degradation of oocyte mRNA species after fertilization).

Thus, the inventors of the present invention have identified an OAS related family member and provide the first indication that oligoadenylate synthetase-like proteins function in gametogenesis and early embryonic development. It is envisioned that modulation of this protein play a role in contraception, fertility, cell proliferative disease, i.e., cancer, or other reproductive diseases.

BRIEF SUMMARY OF THE INVENTION

The present invention is drawn to a novel polynucleotide, polypeptide and variants thereof. Compositions of the present inveniton are involved in gametogenesis or early embryonic development. It is envisioned that the novel polynucleotide or polypeptide mediates mRNA degradation pathways important for gametogenesis or early embryonic development. Yet further, the polynucleotide or polypeptide can mediate mRNA degradation pathways that play a role in the cell proliferation.

The present invention provides polynucleotide sequences SEQ. ID. NO.1, SEQ. ID. NO.3, SEQ. ID. NO.5, SEQ. ID. NO.7, SEQ. ID. NO.9, and SEQ. ID. NO.11.; the protein products they encode, fragments, homologues, and derivatives thereof, and antibodies which are immunoreactive with these protein products.

In a specific embodiment, the present invention provides nucleic acid molecules. These specific nucleic acids may be a naturally-occurring cDNA, genomic DNA, RNA, or a fragment of one of these nucleic acids, or may be a non-naturally-occurring nucleic acid molecule. In preferred embodiment, the nucleic acid molecule encodes a polypeptide that comprises an amino acid sequence of SEQ. ID. NO.2, SEQ. ID. NO.4, SEQ. ID. NO.6, SEQ. ID. NO.8, SEQ. ID. NO.10, or SEQ. ID. NO.12. In yet another embodiment, the nucleic acid molecule comprises a nucleic acid sequence of SEQ. ID. NO.1, SEQ. ID. NO.3, SEQ. ID. NO.5, SEQ. ID. NO.7, SEQ. ID. NO.9, and SEQ. ID. NO.11. By nucleic acid molecule, it is also meant to be inclusive of sequences that selectively hybridize or exhibit substantial sequence similarity to a nucleic acid molecule encoding a gonadal specific protein, or that selectively hybridize or exhibit substantial sequence similarity to a gonadal specific nucleic acids, as well as allelic variants of a nucleic acid molecule encoding a gonadal specific protein, and allelic variants of a gonadal specific nucleic acids.

It is also contemplated that the polynucleotide sequence of the present invention may be an expression cassette comprising the polynucleotide sequence of the present invention operatively linked to a promoter sequence. Still further, the expression cassette may be comprised in a vector.

Another embodiment of the present invention is a pharmaceutical composition comprising a modulator of OASL expression dispersed in a pharmaceutically acceptable carrier. The modulator suppresses and/or enhances transcription of an Oasl gene, for example Oasl6, Oasl7, Oasl8, Oasl9, Oasl10 or Oasl11. Specifically, the modulator can be a polypeptide, a small molecule, a polynucleotide sequence (e.g., is DNA or RNA), and/or an expression vector containing a polynucleotide sequence.

Still further, the present invention provides a pharmaceutical composition comprising a modulator of OASL activity dispersed in a pharmaceutically acceptable carrier. The modulator is a composition that inhibits or stimulates OASL activity, for example, OASL6, OASL7, OASL8, OASL9, OASL10 and OASL11.

Another embodiment is a method of identifying compounds that modulate the activity of OASL comprising the steps of: obtaining an isolated OASL polypeptide or functional equivalent thereof, admixing the OASL polypeptide or functional equivalent thereof with a candidate compound; and measuring an effect of the candidate compound on the activity of OASL. The OASL is selected from the group consisting of OASL6, OASL7, OASL8, OASL9, OASL10 and OASL11. The effect is a decrease in mRNA degradation and/or an increase in mRNA degradation.

A further embodiment is a method of screening for a compound which modulates the activity of OASL comprising: exposing OASL or an OASL binding fragment thereof to a candidate compound; and determining whether the compound binds to OASL or the OASL binding fragment thereof; and further determining whether the compound modulates OASL activity or the interaction of OASL its binding partner.

Still further, another embodiment is a method of screening for an interactive protein which binds with OASL protein comprising: exposing the OASL protein, or OASL fragment thereof to a candidate compound; and determining whether the compound binds to the OASL protein, wherein binding of the candidate compound to the OASL protein indicates an interactive protein.

Another embodiment is a method of identifying a compound that effects OASL activity comprising the steps of: providing a transgenic animal having a regulatable one or more genes encoding an OASL protein, a knock-out of one or more genes encoding an OASL protein, or a knock-in of one or more genes encoding an OASL protein; providing a control animal for the transgenic animal and exposing the transgenic animal group and control animal group to a candidate OASL-modulating compound; and comparing the transgenic animal and the control animal and determining the effect of the compound on one or more OASL proteins related to infertility or fertility in the transgenic animals as compared to the control animals.

A specific embodiment is a method of detecting a binding interaction of a first peptide and a second peptide of a peptide binding pair, comprising the steps of: culturing at least one eukaryotic cell under conditions suitable to detect the selected phenotype; wherein the cell comprises; a polynucleotide sequence encoding a first heterologous fusion protein comprising the first peptide or a segment thereof joined to a DNA binding domain of a transcriptional activation protein; a nucleotide sequence encoding a second heterologous fusion protein comprising the second peptide or a segment thereof joined to a transcriptional activation domain of a transcriptional activation protein; wherein binding of the first peptide or segment thereof and the second peptide or segment thereof reconstitutes a transcriptional activation protein; and; a reporter element activated under positive transcriptional control of the reconstituted transcriptional activation protein, wherein expression of the reporter element produces a selected phenotype; detecting the binding interaction of the peptide binding pair by determining the level of the expression of the reporter element which produces the selected phenotype; wherein said first or second peptide is an OASL peptide and the other peptide is a test peptide, preferably selected peptides/proteins present in the ovary.

Another specific embodiment is a rescue screen for detecting thee binding interaction of a first peptide and a second peptide of a peptide binding pair, comprising: culturing at least one eukaryotic cell under conditions to detect a selected phenotype or the absence of such phenotype, wherein the cell comprises; a nucleotide sequence encoding a first heterologous fusion protein comprising the first peptide or a segment thereof joined to a DNA binding domain of a transcriptional activation protein; a nucleotide sequence encoding a second heterologous fusion protein comprising the second peptide or a segment thereof joined to a transcriptional activation domain of a transcriptional activation protein; wherein binding of the first peptide or segment thereof and the second peptide or segment thereof reconstitutes a transcriptional activation protein; and a reporter element activated under positive transcriptional control of the reconstituted transcriptional activation protein, wherein expression of the reporter element prevents exhibition of a selected phenotype; detecting the ability of the test peptide to interact with OASL by determining whether the test peptide affects the expression of the reporter element which prevents exhibition of the selected phenotype, wherein said first or second peptide is an OASL peptide and the other peptide is a test peptide, preferably selected peptides/proteins present in the ovary.

Another embodiment is a method of identifying binding partners for OASL comprising the steps of: exposing the protein to a potential binding partner; and determining if the potential binding partner binds to OASL.

Still further, another embodiment is a method of screening for a modulator of OASL activity comprising the steps of: providing a cell expressing an OASL polypeptide; contacting the cell with a candidate modulator; measuring OASL expression; and comparing said OASL expression in the presence of said candidate modulator with the expression of OASL expression in the absence of said candidate modulator; wherein a difference in the expression of OASL in the presence of said candidate modulator, as compared with the expression of OASL in the absence of said candidate modulator, identifies said candidate modulator as a modulator of OASL expression. The OASL is selected from the group consisting of OASL6, OASL7, OASL8, OASL9, OASL10 and OASL11.

Another embodiment is a method of producing a modulator of OASL activity comprising the steps of: providing a cell expressing an OASL polypeptide; contacting the cell with a candidate modulator; measuring OASL expression; comparing the OASL expression in the presence of the candidate modulator with the expression of OASL expression in the absence of the candidate modulator; wherein a difference in the expression of OASL in the presence of the candidate modulator, as compared with the expression of OASL in the absence of the candidate modulator, identifies the candidate modulator as a modulator of OASL expression; and producing the modulator.

Still further, another method is a method of modulating mRNA degradation in a germ cell or early embryo of an animal comprising the step of administering to the animal an inhibitor of OASL activity. The germ cell is an oocyte or egg and/or spermatid or spermatazoon. The inhibitor suppresses transcription of an Oasl6, Oasl7, Oasl8, Oasl9, Oasl10 or Oasl11 gene. The inhibitor is a polypeptide or a polynucleotide sequence. The polynucleotide sequence is DNA or RNA. The RNA is an antisense Oasl RNA or is an interference RNA of Oasl RNA.

Another embodiment is a method of contraception comprising administering to an animal an effective amount of a modulator of OASL activity dispersed in a pharmacologically acceptable carrier, wherein said amount is capable of decreasing conception. The OASL is selected from the group consisting of OASL6, OASL7, OASL8, OASL9, OASL10, and OASL11. The animal is female or male.

Still further, another embodiment is a method of modulating mRNA degradation in a germ cell or early embryo of an animal comprising the step of administering to the animal a stimulator of OASL activity. The germ cell is an oocyte or egg and/or spermatid or spermatazoon. The stimulator enhances transcription of an Oasl6, Oasl7, Oasl8, Oasl9, Oasl10 or Oasl11 gene.

A specific embodiment is a method of enhancing fertility comprising administering to an animal an effective amount of a modulator of OASL activity dispersed in a pharmacologically acceptable carrier, wherein said amount is capable of decreasing conception.

Another embodiment is a method of diagnosing infertility comprising identifying a mutation in an OASL polypeptide or polynucleotide.

Still further, another embodiment is a method of modulating a hyperproliferative disease comprising administering to an animal an effective amount of a modulator of OASL activity dispersed in a pharmacologically acceptable carrier. The hyperproliferative disease is further defined as cancer. The cancer is selected from the group consisting of melanoma, non-small cell lung, small-cell lung, lung hepatocarcinoma, retinoblastoma, astrocytoma, gliobastoma, leukemia, neuroblastoma, squamous cell, head, neck, gum, tongue, breast, pancreatic, prostate, renal, bone, testicular, ovarian, mesothelioma, cervical, gastrointestinal, lymphoma, brain, colon, and bladder. In further embodiments, the hyperproliferative disease is selected from the group consisting of benign prostatic hypertrophy (BPH), rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, and psoriasis.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying figures.

FIG. 1A, FIG. 1B and FIG. 1C show a multiple alignment analysis of all murine OAS and OASL proteins. Conserved residues are shaded.

FIG. 2A and FIG. 2B show a multiple alignment analysis of murine OAS1a–c, OASL4–7, and OASL11 proteins. Conserved residues are shaded.

FIG. 3A and FIG. 3B show a multiple alignment analysis of murine OAS1a–c, OASL8–10 proteins. Conserved residues are shaded.

FIG. 10A shows a Northern Blot analysis of Oasl mRNA levels in multiple tissues of Poly [I:C]-treated (+) and control (−) mice. FIG. 10B shows a semi-quantitative PCR analysis of Oasl mRNA expression in multiple tissues of Poly [I:C]-treated and control mice.

FIG. 11A shows total RNA that was reverse transcribed and then the resultant cDNAs were used for PCR amplification. FIG. 11B shows total RNAs isolated from whole prostate (WP), ventral prostate (VP), lateral prostate (LP), dorsal prostate (DP), and coagulating gland (GC) of Poly[I:C]-treated (+) or control (−) mice.

FIG. 15A shows the adult ovary, and FIG. 15B shows the oocytes of primary follicles in the Gdf9 null or knockout ovary. FIG. 15C shows the oocytes, granulosa cells, and luteal cells of the adult ovary, and FIG. 15D shows the oocytes, granulosa cells, and luteal cells Gdf9 null or knockout ovary. Sections stained with pre-immune sera are shown in FIG. 15E and FIG. 15F.

FIG. 16C and FIG. 16D show OASL6 and OAS1 expression in GV oocytes. FIG. 16E and FIG. 16F show OASL6 and OAS1 expression in MII oocytes. FIG. 16G and FIG. 16H show OASL6 and OAS1 expression in 2-cell embryos. FIG. 16I and FIG. 16J show OASL6 and OAS1 expression in 8-cell embryos. Sections stained with pre-immune sera are shown in FIG. 16A and FIG. 16B.

FIG. 17A shows the binding assay of OAS1 and OASL6. FIG. 17B shows the amount of protein used in the binding assay.

DETAILED DESCRIPTION OF THE INVENTION

Figure 4:
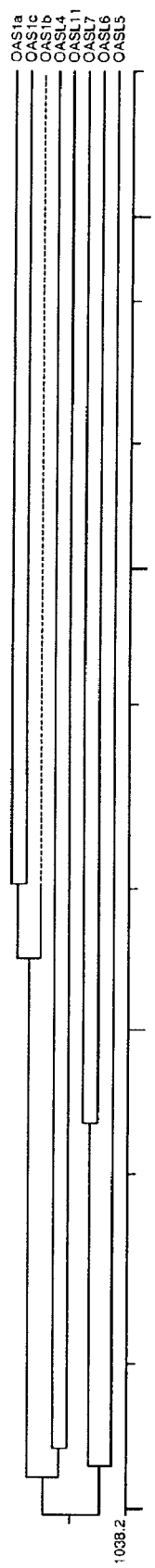
FIG. 4 shows a phylogenetic analysis of murine OAS1a–c, OASL4–7, and OASL11 proteins.

It is readily apparent to one skilled in the art that various embodiments and modifications can be made to the invention disclosed in this Application without departing from the scope and spirit of the invention.

As used herein, the use of the word "a" or "an" when used in conjunction with the term "comprising" in the claims and/or the specification may mean "one," but it is also consistent with the meaning of "one or more," "at least one," and "one or more than one."

As used herein, the term "animal" refers to a mammal, such as human, non-human primates, horse, cow, elephant, cat, dog, rat or mouse. In specific embodiments, the animal is a human.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. Thus, one of skill in the art understands that the term "antibody" refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. (See, i.e., Antibodies: A Laboratory Manual, Cold Spring Harbor Laboratory, 1988).

As used herein, the term "binding protein" refers to proteins that demonstrate binding affinity for a specific ligand. Binding proteins may be produced from separate and distinct genes. For a given ligand, the binding proteins that are produced from specific genes are distinct from the ligand binding domain of the receptor or its soluble receptor.

As used herein, the term "binding partner" or "interacting proteins" refer to a molecule capable of binding another molecule with specificity, as for example, an antigen and an antigen-specific antibody or an enzyme and its inhibitor. Binding partners may include, for example, biotin and avidin or streptavidin, IgG and protein A, receptor-ligand couples, protein-protein interaction, and complementary polynucleotide strands. The term "binding partner" may also refer to polypeptides, lipids, small molecules, or nucleic acids that bind to OASLs in cells. A change in the interaction between a protein and a binding partner can manifest itself as an increased or decreased probability that the interaction forms, or an increased or decreased concentration of OASLs in cells-binding partner complex.

As used herein, the term "OASLs binding fragment" refers to the nucleic acid fragment and/or amino acid fragment of OASLs respectively that is capable of binding to the binding partner or interacting protein, for example polypeptides, lipids, small molecules, or nucleic acids.

As used herein, the terms "cell," "cell line," and "cell culture" may be used interchangeably. All of these terms also include their progeny, which are any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal. Host cell can be used as a recipient for vectors and may include any transformable organisms that are capable of replicating a vector and/or expressing a heterologous nucleic acid encoded by a vector.

As used herein, the term "conception" refers to the union of the male sperm and the ovum of the female; fertilization.

As used herein, the term "contraception" refers to the prevention or blocking of conception. A contraceptive device, thus, refers to any process, device, or method that prevents conception. Well known categories of contraceptives include, steroids, chemical barrier, physical barrier; combinations of chemical and physical barriers; use of immunocontraceptive methods by giving either antibodies to the reproductive antigen of interest or by developing a natural immune response to the administered reproductive antigen; abstinence and permanent surgical procedures. Contraceptives can be administered to either males or females.

As used herein, the term "complementary" is used to describe the relationship between nucleotide bases that are capable to hybridizing to one another. For example, with respect to DNA, adenosine is complementary to thymine and cytosine is complementary to guanine.

As used herein, "cDNA" refers to DNA that is complementary to and derived from an mRNA template. The cDNA can be single-stranded or converted to double-stranded form using, for example, the Klenow fragment of DNA polymerase I.

As used herein, the term "DNA" is defined as deoxyribonucleic acid.

As used herein, the term "DNA segment" refers to a DNA molecule that has been isolated free of total genomic DNA of a particular species. Included within the term "DNA segment" are DNA segments and smaller fragments of such segments, and also recombinant vectors, including, for example, plasmids, cosmids, phage, viruses, and the like.

As used herein, the term "expression construct" or "transgene" is defined as any type of genetic construct containing a nucleic acid coding for gene products in which part or all of the nucleic acid encoding sequence is capable of being transcribed can be inserted into the vector. The transcript is translated into a protein, but it need not be. In certain embodiments, expression includes both transcription of a gene and translation of mRNA into a gene product. In other embodiments, expression only includes transcription of the nucleic acid encoding genes of interest. In the present invention, the term "therapeutic construct" may also be used to refer to the expression construct or transgene. One skilled in the art realizes that the present invention utilizes the expression construct or transgene as a therapy to treat infertility. Yet further, the present invention utilizes the expression construct or transgene as a "prophylactic construct" for contraception. Thus, the "prophylactic construct" is a contraceptive.

As used herein, the term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well and are described infra.

As used herein, the term "gene" is used for simplicity to refer to a functional protein, polypeptide or peptide encoding unit. This functional term includes both genomic sequences, cDNA sequences and engineered segments that express, or may be adapted to express, proteins, polypeptides, domains, peptides, fusion proteins and mutant. Thus, one of skill in the art is aware that the term "native gene" refers to a gene as found in nature with its own regulatory sequences and the term "chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences that are derived from the same source, but arranged in a manner different than that found in nature.

As used herein, the term "fertility" refers to the quality of being productive or able to conceive. Fertility relates to both male and female animals.

As used herein, the terms "identity" or "similarity", as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991. Methods commonly employed to determine identity or similarity between sequences include, but are not limited to those disclosed in Carillo, H., and Lipman, D., SIAM J Applied Math., 48:1073 (1988). Methods to determine identity and similarity are codified in publicly available computer programs. Preferred computer program methods to determine identity and similarity between two sequences include, but are not limited to, GCG program package, Devereux, J., et al., Nucleic Acids Research, 12(1), 387 (1984)), BLASTP, BLASTN, and FASTA Atschul, S. F. et al., J Molec. Biol., 215, 403 (1990)).

As used herein, the term "homologous" refers to the degree of sequence similarity between two polymers (i.e. polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

As used herein, the term "percent homology" refers to the extent of amino acid sequence identity between polypeptides. The homology between any two polypeptides is a direct function of the total number of matching amino acids at a given position in either sequence, e.g, if half of the total number of amino acids in either of the sequences are the same then the two sequences are said to exhibit 50% homology.

The term "fragment", "analog", and "derivative" when referring to the polypeptide of the present invention (e.g., SEQ. ID. NO:2, SEQ. ID. NO.4, SEQ. ID. NO.6, SEQ. ID. NO.8, SEQ. ID. NO.10 or SEQ. ID. NO.12), refers to a polypeptide which may retain essentially the same biological function or activity as such polypeptide. Thus, an analog includes a precursor protein that can be activated by cleavage of the precursor protein portion to produce an active mature polypeptide. The fragment, analog, or derivative of the polypeptide of the present invention (SEQ. ID. NO:2, SEQ. ID. NO.4, SEQ. ID. NO.6, SEQ. ID. NO.8, SEQ. ID. NO.10 or SEQ. ID. NO.12), may be one in which one or more of the amino acids are substituted with a conserved or non-conserved amino acid residues and such amino acid residues may or may not be one encoded by the genetic code, or one in which one or more of the amino acid residues includes a substituent group, or one in which the polypeptide is fused with a compound such as polyethylene glycol to increase the half-life of the polypeptide, or one in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

The term "functional equivalent" as used herein is defined as a polynucleotide that has been engineered to contain distinct sequences while at the same time retaining the capacity to perform the biologic function of interest of the wild-type or reference protein. Thus, as used herein, the term functional equivalent includes truncations, deletions, insertions or substitutions of OASLs (e.g, SEQ. ID. NO:2, SEQ. ID. NO.4, SEQ. ID. NO.6, SEQ. ID. NO.8, SEQ. ID. NO.10 or SEQ. ID. NO.12) which retains their function to play a role in fertility and embryonic development. This also can be accomplished to the degeneracy of the genetic code, i.e., the presence of multiple codons, which encode for the same amino acids. In one example, one of skill in the art may wish to introduce a restriction enzyme recognition sequence into a polynucleotide while not disturbing the ability of that polynucleotide to encode a protein. In another example, a polynucleotide may be (and encode) a functional equivalent with more significant changes. Certain amino acids may be substituted for other amino acids in a protein structure without appreciable loss of interactive binding capacity with structures such as, for example, antigen-binding regions of antibodies, binding sites on substrate molecules, receptors, and such like. So-called "conservative" changes do not disrupt the biological activity of the protein, as the structural change is not one that impinges of the protein's ability to carry out its designed function. It is thus contemplated by the inventors that various changes may be made in the sequence of genes and proteins disclosed herein, while still fulfilling the goals of the present invention.

The term "hyperproliferative disease" is defined as a disease that results from a hyperproliferation of cells. Hyperproliferative disease is further defined as cancer. The hyperproliferation of cells results in unregulated growth, lack of differentiation, local tissue invasion, and metastasis. Exemplary hyperproliferative diseases include, but are not limited to cancer or autoimmune diseases. Other hyperproliferative diseases can include vascular occlusion, restenosis, atherosclerosis, benign prostate hyperplasia (BPH) or inflammatory bowel disease.

As used herein, the term "infertility" refers to the inability or diminished ability to conceive or produce offspring. Infertility can be present in either male or female. In the present invention, administration of a composition to enhance infertility or decrease fertility is reversible.

Examples of infertility include, without limitation, azoospermia; genetic disorders associated with defective spermatogenesis (e.g., Klinefelter's syndrome and gonadal dysgenesis); oligospermia, varicocele, and other sperm disorders relating to low sperm counts, sperm motility, and sperm morphology; and ovulatory dysfunction (e.g., polycystic ovary syndrome (PCOS) or chronic anovulation).

As used herein, the term "inhibitor" refers to a compound or composition that decreases OASL or OAS activity. For example, an inhibitor can decrease OASL gene or protein activity or decrease OAS gene or protein activity. An inhibitor can be a polynucleotide, a polypeptide, an antibody, or a small molecule.

As used herein, the term "modulate" refers to the suppression, enhancement, or induction of a function. For example, "modulation" or "regulation" of gene expression refers to a change in the activity of a gene. Modulation of expression can include, but is not limited to, gene activation and gene repression. "Modulate" or "regulate" also refers to methods, conditions, or agents which increase or decrease the biological activity of a protein, enzyme, inhibitor, signal transducer, receptor, transcription activator, co-factor, and the like. This change in activity can be an increase or decrease of mRNA translation, DNA transcription, and/or mRNA or protein degradation, which may in turn correspond to an increase or decrease in biological activity. Such enhancement or inhibition may be contingent upon occurrence of a specific event, such as activation of a signal transduction pathway and/or may be manifest only in particular cell types.

As used herein, the term "modulated activity" refers to any activity, condition, disease or phenotype that is modulated by a biologically active form of a protein. Modulation may be affected by affecting the concentration of biologically active protein, e.g., by regulating expression or degradation, or by direct agonistic or antagonistic effect as, for example, through inhibition, activation, binding, or release of substrate, modification either chemically or structurally, or by direct or indirect interaction which may involve additional factors.

As used herein, the term "modulator" refers to any composition and/or compound that alters the expression of a specific activity, such as OAS or OASLs activity or expression. The modulator is intended to comprise any composition or compound, e.g., antibody, small molecule, peptide, oligopeptide, polypeptide, or protein.

The term "small molecule" refers to a synthetic or naturally occurring chemical compound, for instance a peptide or oligonucleotide that may optionally be derivatized, natural product or any other low molecular weight (typically less than about 5 kDalton) organic, bioinorganic or inorganic compound, of either natural or synthetic origin. Such small molecules may be a therapeutically deliverable substance or may be further derivatized to facilitate delivery.

The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation. As used herein, the term "peptide binding pair" refers to any pair of peptides having a known binding affinity for which the DNA sequence is known or can be deduced. The peptides of the peptide binding pair must exhibit preferential binding for each other over any other components of the modified cell.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic and/or prophylactic compositions is contemplated. Supplementary active ingredients also can be incorporated into the compositions.

As used herein, the terms "polynucleotide", "nucleotide sequence", "nucleic acid", "nucleic acid molecule", "nucleic acid sequence", "oligonucleotide", refer to a series of nucleotide bases (also called "nucleotides") in DNA and RNA, and mean any chain of two or more nucleotides. The polynucleotides can be chimeric mixtures or derivatives or modified versions thereof, single-stranded or double-stranded. The oligonucleotide can be modified at the base moiety, sugar moiety, or phosphate backbone, for example, to improve stability of the molecule, its hybridization parameters, etc. The antisense oligonuculeotide may comprise a modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine. A nucleotide sequence typically carries genetic information, including the information used by cellular machinery to make proteins and enzymes. These terms include double- or single-stranded genomic and cDNA, RNA, any synthetic and genetically manipulated polynucleotide, and both sense and antisense polynucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil, or containing carbohydrate, or lipids.

As used herein, the term "polypeptide" is defined as a chain of amino acid residues, usually having a defined sequence. As used herein, the term polypeptide is interchangeable with the terms "peptides" and "proteins".

As used herein, the term "promoter" is defined as a DNA sequence recognized by the synthetic machinery of the cell, or introduced synthetic machinery, required to initiate the specific transcription of a gene.

As used herein, the term "purified protein or peptide" is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

As used herein, the term "stimulator" is defined as a compound or composition that enhances the activity of OASL or OAS. The enhanced activity can be OASL gene activity, OASL protein activity, OAS gene activity or OAS protein activity. A stimulator can be a polynucleotide, a polypeptide, an antibody, or a small molecule.

As used herein, "messenger RNA (mRNA)" refers to the RNA that is without introns and can be translated into polypeptides by the cell.

As used herein, the term "RNA" is defined as ribonucleic acid.

As used herein, the term "RNA interference" or "iRNA" is an RNA molecule that is used to inhibit a particular gene of interest.

As used herein, the term "under transcriptional control" or "operatively linked" is defined as the promoter is in the correct location and orientation in relation to the nucleic acid to control RNA polymerase initiation and expression of the gene.

As used herein, the term "regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

As used herein, the term "sense" refers to sequences of nucleic acids that are in the same orientation as the coding MRNA nucleic acid sequence. A DNA sequence linked to a promoter in a "sense orientation" is linked such that an RNA molecule which contains sequences identical to an mRNA is transcribed. The produced RNA molecule, however, need not be transcribed into a functional protein.

As used herein, the term an "anti-sense" copy of a particular polynucleotide refers to a complementary sequence that is capable of hydrogen bonding to the polynucleotide and can therefor be capable of modulating expression of the polynucleotide. These are DNA, RNA or analogs thereof, including analogs having altered backbones, as described above. The polynucleotide to which the anti-sense copy binds may be in single-stranded form or in double-stranded form. A DNA sequence linked to a promoter in an "anti-sense orientation" may be linked to the promoter such that an RNA molecule complementary to the coding mRNA of the target gene is produced.

As used herein, the terms "sense" strand and an "anti-sense" strand when used in the same context refer to single-stranded polynucleotides that are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

I. OASL Proteins

The protein sequences for OASLs are provided in the following SEQ. ID. NO:2, SEQ. ID. NO.4, SEQ. ID. NO.6, SEQ. ID. NO.8, SEQ. ID. NO.10 or SEQ. ID. NO.12.

In this patent, the terms "OASL gene product" or "OAS gene product" refer to proteins and polypeptides having amino acid sequences that are substantially identical to the native OASLs or OAS, e.g, OASL6, OASL7, OASL8, OASL9, OASL10 or OASL11 amino acid sequences (or RNA, if applicable) or that are biologically active, in that they are capable of performing functional activities similar to an endogenous OASL or OAS and/or cross-reacting with anti-OASL or anti-OAS antibody raised against OASL and/or OAS.

The terms "OASL gene product" and/or "OAS gene product" also include analogs of the respective molecules that exhibit at least some biological activity in common with their native counterparts. Such analogs include, but are not limited to, truncated polypeptides and polypeptides having fewer amino acids than the native polypeptide.

In addition to the entire OASL molecules, the present invention also relates to fragments of the polypeptides that may or may not retain the functions described below. Fragments, including the N-terminus of the molecule, may be generated by genetic engineering of translation stop sites within the coding region. Alternatively, treatment of the OASLs with proteolytic enzymes, known as proteases, can produces a variety of N-terminal, C-terminal and internal fragments. Examples of fragments may include contiguous residues of SEQ. ID. NO:2, SEQ. ID. NO.4, SEQ. ID. NO.6, SEQ. ID. NO.8, SEQ. ID. NO.10 or SEQ. ID. NO.12 of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, 200 or more amino acids in length. These fragments may be purified according to known methods, such as precipitation (i.e., ammonium sulfate), HPLC, ion exchange chromatography, affinity chromatography (including immunoaffinity chromatography) or various size separations (sedimentation, gel electrophoresis, gel filtration).

It is also contemplated that other OAS and/or OASL protein sequences can be used in the present invention, for example, but not limited to OAS1a: SEQ. ID. NO.13; OAS1b: SEQ. ID. NO.14, OAS1c: SEQ. ID. NO.15, OASL4: SEQ. ID. NO.16; OASL5: SEQ. ID. NO.17; OAS1: SEQ. ID. NO.24; OAS2: SEQ. ID. NO.26; and OAS3: SEQ. ID. NO.28.

The term substantially pure as used herein refers to OASLs and/or OAS which are substantially free of other proteins, lipids, carbohydrates or other materials with which they are naturally associated. One skilled in the art can purify OASLs and/or OAS using standard techniques for protein purification. The substantially pure polypeptide will yield a single major band on a non-reducing polyacrylamide gel. The purity of the OASLs and/or OAS polypeptides can also be determined by amino-terminal amino acid sequence analysis. OASLs and/or OAS polypeptides include functional fragments of the polypeptides, as long as their activities remain. Smaller peptides containing the biological activities of OASLs and/or OAS may also be used in the present invention.

A. Variants of OASLs

Amino acid sequence variants of the OASL polypeptides can be substitutional, insertional or deletion variants. These changes may be conservative or non-conservative changes. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within 12 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (-0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Equally, the same considerations may be employed to create a protein, polypeptide or peptide with countervailing, i.e., antagonistic properties. This is relevant to the present invention in which OASL mutants or analogues may be generated using non-conservative substitutions, insertions and/or deletions. For example, a OASL mutant may be generated and tested for OASL activity to identify those residues important for OASL activity. OASL6 mutants may also be synthesized to reflect a OASL mutant that occurs in the human population and that is linked to the development of cancer. Also, OASL mutants may be used as antagonists to inhibit or enhance fertility. Thus, OASL mutants may be used as potential contraceptive compositions and/or fertility enhancement compositions.

B. Domain Switching

Yet further, the present invention has identified murine and human OASL proteins. An interesting series of mutants can be created by substituting homologous regions of various proteins. This is known, in certain contexts, as "domain switching."

Domain switching involves the generation of chimeric molecules using different but, in this case, related polypeptides. By comparing various OASL proteins, one can make predictions as to the functionally significant regions of these molecules. It is possible, then, to switch related domains of these molecules in an effort to determine the criticality of these regions to OASL function. These molecules may have additional value in that these "chimeras" can be distinguished from natural molecules, while often providing the same function.

C. Fusion Proteins

A specialized kind of insertional variant is the fusion protein. This molecule generally has all or a substantial portion of the native molecule, linked at the N- or C-terminus, to all or a portion of a second polypeptide. Fusions typically employ leader sequences from other species to permit the recombinant expression of a protein in a heterologous host. For example, a fusion protein of the present invention can includes the addition of a protein transduction domains, for example, but not limited to Antennepedia transduction domain (ANTP), HSV1 (VP22) and HIV-1

(Tat). Fusion proteins containing protein transduction domains (PTDs) can traverse biological membranes efficiently, thus delivering the protein of interest (OAS, OASL or variant thereof, such as an activator or inhibitor) into the cell. (Tremblay, 2001; Forman et al., 2003).

Yet further, inclusion of a cleavage site at or near the fusion junction will facilitate removal of the extraneous polypeptide after purification. Other useful fusions include linking of functional domains, such as active sites from enzymes, glycosylation domains, other cellular targeting signals or transmembrane regions.

D. Purification of Proteins

In specific embodiments of the present invention, it is desirable to purify OASLs or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

E. Synthetic Peptides

The present invention also describes smaller OASL-related peptides for use in various embodiments of the present invention. Because of their relatively small size, the peptides of the invention can also be synthesized in solution or on a solid support in accordance with conventional techniques. Various automatic synthesizers are commercially available and can be used in accordance with known protocols. See, for example, Stewart and Young (1984); Tam et al. (1983); Merrifield (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

F. Antigen Compositions

The present invention also provides for the use of OASL proteins or peptides as antigens for the immunization of animals relating to the production of antibodies. It is envisioned that OASL or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyanin (KLH) or bovine serum albumin (BSA).

1. Antibody Production

In certain embodiments, the present invention provides antibodies that bind with high specificity to the OASL polypeptides provided herein. Thus, antibodies that bind to the polypeptide of SEQ. ID. NO:2, SEQ. ID. NO.4, SEQ. ID. NO.6, SEQ. ID. NO.8, SEQ. ID. NO.10 or SEQ. ID. NO.12 are provided. In addition to antibodies generated against the full length proteins, antibodies may also be generated in response to smaller constructs comprising epitopic core regions, including wild-type and mutant epitopes.

Monoclonal antibodies (MAbs) are recognized to have certain advantages, i.e., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, humanized antibodies are also contemplated, as are chimeric antibodies from mouse, rat, or other species, bearing human constant and/or variable region domains, bispecific antibodies, recombinant and engineered antibodies and fragments thereof. Methods for the development of antibodies that are "custom-tailored" to the patient's disease are likewise known and such custom-tailored antibodies are also contemplated.

A polyclonal antibody is prepared by immunizing an animal with an immunogenic OASL composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, toxins or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, Pa.); low-dose Cyclophosphamide (CYP; 300 mg/m2) (Johnson/ Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, may also be given. The process of boosting and titering is repeated until a suitable titer is achieved. When a desired level of immunogenicity is obtained, the immunized animal can be bled and the serum isolated and stored, and/or the animal can be used to generate MAbs.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Mycloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, i.e., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (i.e., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods, which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in *E. coli*.

2. Antibody Conjugates

The present invention further provides antibodies against OASL, generally of the monoclonal type, that are linked to one or more other agents to form an antibody conjugate. Any antibody of sufficient selectivity, specificity and affinity may be employed as the basis for an antibody conjugate. Such properties may be evaluated using conventional immunological screening methodology known to those of skill in the art.

Certain examples of antibody conjugates are those conjugates in which the antibody is linked to a detectable label. "Detectable labels" are compounds or elements that can be detected due to their specific functional properties, or chemical characteristics, the use of which allows the antibody to which they are attached to be detected, and further quantified if desired. Another such example is the formation of a conjugate comprising an antibody linked to a cytotoxic or anti-cellular agent, as may be termed "immunotoxins" (described in U.S. Pat. Nos. 5,686,072, 5,578,706, 4,792,447, 5,045,451, 4,664,911 and 5,767,072, each incorporated herein by reference).

Antibody conjugates are thus preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Again, antibody-directed imaging is less preferred for use with this invention.

Many appropriate imaging agents are known in the art, as are methods for their attachment to antibodies (see, i.e., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention $^{211}$astatine, $^{14}$carbon, $^{51}$chromium, $^{36}$chlorine, $^{57}$cobalt, $^{58}$cobalt, $^{67}$copper, $^{152}$Eu, $^{67}$gallium, $^{3}$hydrogen, $^{123}$iodine, $^{125}$iodine, $^{131}$iodine, $^{111}$indium, 59iron, $^{32}$phosphorus, $^{186}$rhenium, $^{188}$rhenium, $^{75}$selenium, $^{35}$sulphur, and $^{99m}$technicium. $^{125}$I is often being preferred for use in certain embodiments, and $^{99m}$techniciumand $^{111}$indium are also often preferred due to their low energy and suitability for long range detection.

Radioactively labeled monoclonal antibodies of the present invention may be produced according to well-known methods in the art. For instance, monoclonal antibodies can be iodinated by contact with sodium or potassium iodide and a chemical oxidizing agent such as sodium hypochlorite, or an enzymatic oxidizing agent, such as lactoperoxidase. Monoclonal antibodies according to the invention may be labeled with $^{99m}$technetium by ligand exchange process, for example, by reducing pertechnate with stannous solution, chelating the reduced technetium onto a Sephadex column and applying the antibody to this column or by direct labeling techniques, i.e., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) and ethylene diaminetetracetic acid (EDTA). Also contemplated for use are fluorescent labels, including rhodamine, fluorescein isothiocyanate and renographin.

The much preferred antibody conjugates of the present invention are those intended primarily for use in vitro, where the antibody is linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

II. Oasl Nucleic Acids

Important aspects of the present invention concern isolated DNA segments and recombinant vectors encoding OASL proteins, polypeptides or peptides, and the creation and use of recombinant host cells through the application of DNA technology, that express a wild-type, polymorphic or mutant OASL, using the sequence of SEQ. ID. NO.1, SEQ. ID. NO.3, SEQ. ID. NO.5, SEQ. ID. NO.7, SEQ. ID. NO.9, or SEQ. ID. NO.11, and biologically functional equivalents thereof.

It is also contemplated that other OAS and/or OASL nucleic acid sequences can be used in the present invention, for example, but not limited to OAS1a: SEQ. ID. NO.18; OAS1b: SEQ. ID. NO.19, OAS1c: SEQ. ID. NO.20, OASL4: SEQ. ID. NO.21 AND OASL5: SEQ. ID. NO.22; OAS1: SEQ. ID. NO.23; OAS2: SEQ. ID. NO.25; and OAS3: SEQ. ID. NO.27.

The present invention concerns DNA segments, isolatable from mammalian cells, such as mouse, rat or human cells, that are free from total genomic DNA and that are capable of expressing a protein, polypeptide or peptide. Therefore, a DNA segment encoding Oasl refers to a DNA segment that contains wild-type, polymorphic or mutant Oasl coding sequences yet is isolated away from, or purified free from, total mammalian genomic DNA.

Similarly, a DNA segment comprising an isolated or purified Oasl gene refers to a DNA segment encoding OASL protein, polypeptide or peptide coding sequences and, in certain aspects, regulatory sequences, isolated substantially away from other naturally-occurring genes or protein encoding sequences. As will be understood by those in the art, this functional term gene includes both genomic sequences, cDNA sequences and engineered segments that express, or may be adapted to express, proteins, polypeptides, domains, peptides, fusion proteins and mutants of Oasl encoded sequences.

Isolated substantially away from other coding sequences means that the gene of interest, in this case the Oasl gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

A. Variants

In particular embodiments, the invention concerns isolated DNA segments and recombinant vectors incorporating DNA sequences that encode an OASL protein, polypeptide or peptide that includes within its amino acid sequence a contiguous amino acid sequence in accordance with, or essentially as set forth in, SEQ. ID. NO:2, SEQ. ID. NO.4, SEQ. ID. NO.6, SEQ. ID. NO.8, SEQ. ID. NO.10 or SEQ. ID. NO.12, such the sequence substantially corresponds to a portion of SEQ. ID. NO:2, SEQ. ID. NO.4, SEQ. ID. NO.6, SEQ. ID. NO.8, SEQ. ID. NO.10 or SEQ. ID. NO.12 and has relatively few amino acids that are not identical to, or a biologically functional equivalent of, the amino acids of SEQ. ID. NO:2, SEQ. ID. NO.4, SEQ. ID. NO.6, SEQ. ID. NO.8, SEQ. ID. NO.10 or SEQ. ID. NO.12.

Thus, in particular embodiments, the biological activity of an OASL protein, polypeptide or peptide, or a biologically functional equivalent, for example, is involved in MRNA degradation. Yet further, it is envisioned that OASL lacks 2–5A synthesizing capabilities.

In certain other embodiments, the invention concerns isolated DNA segments and recombinant vectors that include within their sequence a nucleic acid sequences essentially as set forth in SEQ. ID. NO.1, SEQ. ID. NO.3, SEQ. ID. NO.5, SEQ. ID. NO.7, SEQ. ID. NO.9, or SEQ. ID. NO.11. The term essentially as set forth in SEQ. ID. NO.1, SEQ. ID. NO.3, SEQ. ID. NO.5, SEQ. ID. NO.7, SEQ. ID. NO.9, or SEQ. ID. NO.11 is used in the same sense as described above and means that the nucleic acid sequence substantially corresponds to a portion of SEQ. ID. NO.1, SEQ. ID. NO.3, SEQ. ID. NO.5, SEQ. ID. NO.7, SEQ. ID. NO.9, or SEQ. ID. NO.11 and has relatively few codons that are not identical, or functionally equivalent, to the codons of SEQ. ID. NO.1, SEQ. ID. NO.3, SEQ. ID. NO.5, SEQ. ID. NO.7, SEQ. ID. NO.9, or SEQ. ID. NO.11.

Functionally equivalent codons are codons that encode the same amino acid, such as the six codons for arginine and serine, and it also refers to codons that encode biologically equivalent amino acids. Codon usage for various organisms and organelles is well known in the art, thus allowing one of skill in the art to optimize codon usage for expression in various organisms using the disclosures herein. It is contemplated that codon usage may be optimized for the desired animals, as well as other organisms such as a prokaryote (i.e., an eubacteria, an archaea), an eukaryote (i.e., a protist, a plant, a fungi, an animal), a virus and the like, as well as organelles that contain nucleic acids, such as mitochondria or chloroplasts, based on the preferred codon usage as would be known to those of ordinary skill in the art.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein, polypeptide or peptide activity where an amino acid sequence expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

Equally, the same considerations may be employed to create a protein, polypeptide or peptide with countervailing, i.e., antagonistic properties. This is relevant to the present invention in which OASL mutants or analogues may be generated using non-conservative substitutions, insertions and/or deletions. OASL mutants may be used as antagonists to inhibit or enhance fertility. Thus, OASL mutants may be used as potential contraceptive compositions and/or fertility enhancement compositions.

A. Complentary Nucleic Acids

The present invention also encompasses a nucleic acid that is complementary to an OASL and/or OAS nucleic acid. In particular embodiments the invention encompasses a nucleic acid or a nucleic acid segment complementary to the sequence set forth in SEQ. ID. NO.1, SEQ. ID. NO.3, SEQ. ID. NO.5, SEQ. ID. NO.7, SEQ. ID. NO.9, or SEQ. ID. NO.11. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g, one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

B. Nucleic Acid Hybridization

The nucleic acid sequences disclosed herein also have a variety of uses, such as for example, utility as probes or primers in nucleic acid hybridization embodiments.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. For example, a medium stringency condition could be provided by about 0.1 to 0.25 M NaCl at temperatures of about 37° C. to about 55° C. Under these conditions, hybridization may occur even though the sequences of probe and target strand are not perfectly complementary, but are mismatched at one or more positions. In another example, a low stringency condition could be provided by about 0.15 M to about 0.9 M salt, at temperatures ranging from about 20° C. to about 55° C. Of course, it is within the skill of one in the art to further modify the low or high stringency conditions to suite a particular application. For example, in other embodiments, hybridization may be achieved under conditions of, 50 mM Tris-HCl (pH 8.3), 75 mM KCl, 3 mM MgCl2, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C.

Accordingly, the nucleotide sequences of the disclosure may be used for their ability to selectively form duplex molecules with complementary stretches of genes or RNAs or to provide primers for amplification of DNA or RNA from tissues. Depending on the application envisioned, it is preferred to employ varying conditions of hybridization to achieve varying degrees of selectivity of probe towards target sequence.

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

The use of a hybridization probe of between 17 and 100 nucleotides in length, or in some aspect of the invention even up to 1–2 Kb or more in length, allows the formation of a duplex molecule that is both stable and selective. Molecules having complementary sequences over stretches greater than 20 bases in length are generally preferred, in order to increase stability and selectivity of the hybrid, and thereby improve the quality and degree of particular hybrid molecules obtained. One will generally prefer to design nucleic acid molecules having stretches of 20 to 30 nucleotides, or even longer where desired. Such fragments may be readily prepared by, for example, directly synthesizing the fragment by chemical means or by introducing selected sequences into recombinant vectors for recombinant production.

In general, it is envisioned that the hybridization probes described herein will be useful both as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The selected conditions will depend on the particular circumstances based on the particular criteria required (depending, for example, on the "G+C" content, type of target nucleic acid, source of nucleic acid, size of hybridization probe, etc.). Following washing of the hybridized surface to remove non-specifically bound probe molecules, hybridization is detected, or even quantified, by means of the label.

C. Nucleic Acid Amplification

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to Oasl genes are contacted with the isolated nucleic acid under conditions that permit selective hybridization. The term "primer," as defined herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals.

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, i.e., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al, 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'[alpha-thio]-triphosphates in one strand of a restriction site may also be useful in the amplification of nucleic acids in the present invention.

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (i.e., biotin) and/or a detector moiety (i.e., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Gingeras et al., PCT Application WO 88/10315, incorporated herein by reference). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EP 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990, incorporated herein by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

D. Nucleic Acid Detection

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means visible to the human eye or spectrophotometrically, to identify specific hybridization with complementary nucleic acid-containing samples.

In embodiments wherein nucleic acids are amplified, it is desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blot and hybridization analysis with a labeled probe. The techniques involved in Southern blot analysis are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and noncovalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

III. Engineering Expression Constructs

In certain embodiments, the present invention involves the manipulation of genetic material to produce expression constructs that encode an Oasl gene. Such methods involve the generation of expression constructs containing, for example, a heterologous DNA encoding a gene of interest and a means for its expression, replicating the vector in an appropriate helper cell, obtaining viral particles produced therefrom, and infecting cells with the recombinant virus particles.

The gene will be a normal Oasl gene discussed herein above. In the context of gene therapy, the gene will be a heterologous DNA, meant to include DNA derived from a source other than the viral genome which provides the backbone of the vector. The gene may be derived from a prokaryotic or eukaryotic source such as a bacterium, a virus, a yeast, a parasite, a plant, or even an animal. The heterologous DNA also may be derived from more than one source, i.e., a multigene construct or a fusion protein. The heterologous DNA also may include a regulatory sequence which may be derived from one source and the gene from a different source.

Yet further, the present invention can involve constructing chimeric polynucleotide sequences. Such sequences can be used to overexpress proteins in cells. The chimeric transgenes or chimeric constructs are generated by using a promoter capable of directing expression of a polynucleotide sequence in the desired tissues at the desired stage of development. These chimeric constructs can comprise promoter sequences and translation leader sequences derived from the same polynucleotide sequences. Also, 3' non-coding polynucleotide sequences encoding transcription termination signals can also be included. It is also envisioned that the chimeric construct can also comprise one or more introns in order to facilitate expression of the polynucleotide sequence.

A. Selectable Markers

In certain embodiments of the invention, the therapeutic expression and/or prophylactic constructs of the present invention contain nucleic acid constructs whose expression is identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin and histidinol are useful selectable markers. Alternatively, enzymes such as herpes simplex virus thymidine kinase (tk) are employed. Immunologic markers also can be employed. The selectable marker employed is not believed to be important, so long as it is capable of being expressed simultaneously with the nucleic acid encoding a gene product. Further examples of selectable markers are well known to one of skill in the art and include reporters such as EGFP, βgal or chloramphenicol acetyltransferase (CAT).

B. Control Regions

1. Promoters

The particular promoter employed to control the expression of a polynucleotide sequence of interest is not believed to be important, so long as it is capable of directing the expression of the polynucleotide in the targeted cell. Thus, where a human cell is targeted, it is preferable to position the polynucleotide sequence coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product. For example in the case where expression of a transgene, or transgenes when a multicistronic vector is utilized, is toxic to the cells in which the vector is produced in, it is desirable to prohibit or reduce expression of one or more of the transgenes. Examples of transgenes that are toxic to the producer cell line are pro-apoptotic and cytokine genes. Several inducible promoter systems are available for production of viral vectors where the transgene product are toxic.

The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of *E. coli*. The tetracycline operator sequence to which the tetracycline repressor binds, and the tetracycline, repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tertracycline repressor. Thus in the absence of doxycycline, transcription is constitutively on. In the Tet-On™ system, the tetracycline repressor is not wild type and in the presence of doxycycline activates transcription. For gene therapy vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

Yet further, another regulable system is RU486 (Pierson et al., 2000). This system is a ligand-inducible system. In the presence of RU486 or mifepristone, transcription is activated. The GeneSwitch system comprises a chimeric regulator (GLVP), which is composed of mutated progesterone receptor ligand-binding domain that binds and is activated by RU486.

In some circumstances, it is desirable to regulate expression of a transgene in a gene therapy vector. For example, different viral promoters with varying strengths of activity are utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoetic cells is desired, retroviral promoters such as the LTRs from MLV or MMTV are often used. Other viral promoters that are used depending on the desired effect include SV40, RSV LTR, HIV-1 and HIV-2 LTR, adenovirus promoters such as from the E1A, E2A, or MLP region, AAV LTR, HSV-TK, and avian sarcoma virus.

Similarly tissue specific promoters are used to effect transcription in specific tissues or cells so as to reduce potential toxicity or undesirable effects to non-targeted tissues. For example, promoters such as an female germ cell specific promoter include, but are not limited to: ZP3 (zonal pellucida protein 3) (Lira et al., 1990), ZP2 (zonal pellucida protein 2), ZP1 (zonal pellucida protein 1), kit, GDF-9, Oct-4, Fig-alpha promoter, and germ cell specific. Male germ cell promoters include, but are not limited to PGK2 promoter (Zhang et al., 1999); Protamine promoter (Peschon et al., 1987), fig-alpha, cystatin T and INSL6.

In certain indications, it is desirable to activate transcription at specific times after administration of the gene therapy vector. This is done with such promoters as those that are hormone or cytokine regulatable. Cytokine and inflammatory protein responsive promoters that can be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-i acid glycoprotein (Prowse and Baumann, 1988), alpha-1 antitrypsin, lipoprotein lipase (Zechner et al., 1988), angiotensinogen (Ron et al., 1991), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin.

It is envisioned that any of the above promoters alone or in combination with another can be useful according to the present invention depending on the action desired. In addition, this list of promoters should not be construed to be exhaustive or limiting, those of skill in the art will know of other promoters that are used in conjunction with the promoters and methods disclosed herein.

2. Enhancers

Enhancers are genetic elements that increase transcription from a promoter located at a distant position on the same molecule of DNA. Enhancers are organized much like promoters. That is, they are composed of many individual elements, each of which binds to one or more transcriptional proteins. The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Any promoter/enhancer combination (as per the Eukaryotic Promoter Data Base EPDB) can be used to drive expression of the gene. Eukaryotic cells can support cytoplasmic transcription from certain bacterial promoters if the appropriate bacterial polymerase is provided, either as part of the delivery complex or as an additional genetic expression construct.

3. Polyadenylation Signals

Where a cDNA insert is employed, one will typically desire to include a polyadenylation signal to effect proper polyadenylation of the gene transcript. The nature of the polyadenylation signal is not believed to be crucial to the successful practice of the invention, and any such sequence is employed such as human or bovine growth hormone and SV40 polyadenylation signals. Also contemplated as an element of the expression cassette is a terminator. These elements can serve to enhance message levels and to minimize read through from the cassette into other sequences.

4. Integration sequences

In instances wherein it is beneficial that the expression vector replicate in a cell, the vector may integrate into the genome of the cell by way of integration sequences, i.e., retrovirus long terminal repeat sequences (LTRs), the adeno-associated virus ITR sequences, which are present in the vector, or alternatively, the vector may itself comprise an origin of DNA replication and other sequence which facilitate replication of the vector in the cell while the vector maintains an episomal form. For example, the expression vector may optionally comprise an Epstein-Barr virus (EBV) origin of DNA replication and sequences which encode the EBV EBNA-1 protein in order that episomal replication of the vector is facilitated in a cell into which the vector is introduced. For example, DNA constructs having the EBV origin and the nuclear antigen EBNA-1 coding are capable of replication to high copy number in mammalian cells and are commercially available from, for example, Invitrogen (San Diego, Calif.).

It is important to note that in the present invention it is not necessary for the expression vector to be integrated into the genome of the cell for proper protein expression. Rather, the expression vector may also be present in a desired cell in the form of an episomal molecule. For example, there are certain cell types in which it is not necessary that the expression vector replicate in order to express the desired protein. These cells are those which do not normally replicate and yet are fully capable of gene expression. An expression vector is introduced into non-dividing cells and express the protein encoded thereby in the absence of replication of the expression vector.

IV. Methods of Gene Transfer

In order to mediate the effect of the transgene expression in a cell, it will be necessary to transfer the expression constructs of the present invention into a cell. Such transfer may employ viral or non-viral methods of gene transfer. This section provides a discussion of methods and compositions of gene transfer.

A. Non-viral Transfer

Several non-viral methods for the transfer of expression constructs into cells are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu and Wu, 1987; Wu and Wu, 1988).

In a specific embodiment of the present invention, the expression construct is complexed to a cationic polymer. Cationic polymers, which are water-soluble complexes, are well known in the art and have been utilized as a delivery system for DNA plasmids. This strategy employs the use of a soluble system, which will convey the DNA into the cells via a receptor-mediated endocytosis (Wu & Wu 1988). One skilled in the art realizes that the complexing nucleic acids with a cationic polymer will help neutralize the negative charge of the nucleic acid allowing increased endocytic uptake.

In a particular embodiment of the invention, the expression construct is entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). The addition of DNA to cationic liposomes causes a topological transition from liposomes to optically birefringent liquid-crystalline condensed globules (Radler et al., 1997). These DNA-lipid complexes are potential non-viral vectors for use in gene therapy.

Liposome-mediated nucleic acid delivery and expression of foreign DNA in vitro has been very successful. Using the β-lactamase gene, Wong et al., (1980) demonstrated the feasibility of liposome-mediated delivery and expression of foreign DNA in cultured chick embryo, HeLa, and hepatoma cells. Nicolau et al., (1987) accomplished successful liposome-mediated gene transfer in rats after intravenous injection. Also included are various commercial approaches involving "lipofection" technology.

In certain embodiments of the invention, the liposome is complexed with a hemagglutinating virus (HVJ). This has been shown to facilitate fusion with the cell membrane and promote cell entry of liposome-encapsulated DNA (Kaneda et al., 1989). In other embodiments, the liposome is complexed or employed in conjunction with nuclear nonhistone chromosomal proteins (HMG-1) (Kato et al., 1991). In yet further embodiments, the liposome is complexed or employed in conjunction with both HVJ and HMG-1. In that such expression constructs have been successfully employed in transfer and expression of nucleic acid in vitro and in vivo, then they are applicable for the present invention.

In other embodiments, the delivery vehicle may comprise a ligand and a liposome. For example, Nicolau et al., (1987) employed lactosyl-ceramide, a galactose-terminal asialgangliosoide, incorporated into liposomes and observed an increase in the uptake of the insulin gene by hepatocytes. Thus, it is feasible that a nucleic acid encoding a therapeutic gene also is specifically delivered into a cell type such as prostate, epithelial or tumor cells, by any number of receptor-ligand systems with or without liposomes. For example, the human prostate-specific antigen (Watt et al., 1986) is used as the receptor for mediated delivery of a nucleic acid in prostate tissue.

In another embodiment of the invention, the expression construct may simply consist of naked recombinant DNA or plasmids. Transfer of the construct is performed by any of the methods mentioned above which physically or chemically permeabilize the cell membrane. This is applicable particularly for transfer in vitro, however, it is applied for in vivo use as well. Dubensky et al., (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a CAM also is transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

B. Viral Vector-Mediated Transfer

In certain embodiments, transgene is incorporated into a viral particle to mediate gene transfer to a cell. Typically, the virus simply will be exposed to the appropriate host cell under physiologic conditions, permitting uptake of the virus. The present methods are advantageously employed using a variety of viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. The two goals are, to an extent, coterminous in that elimination of adenoviral genes serves both ends. By practice of the present invention, it is possible achieve both these goals while retaining the ability to manipulate the therapeutic constructs with relative ease.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, i.e., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194–358 bp) region of the genome grew poorly even in a cell line that complemented the early (E1A) function (Hearing and Shenk, 1983). When a compensating adenoviral DNA (0–353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

2. Retrovirus

The retroviruses are a group of single-stranded RNA viruses characterized by an ability to convert their RNA viruses into double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Ψ components is constructed (Mann et al., 1983). When a recombinant plasmid containing a human CDNA, together with the retroviral LTR and T sequences is introduced into this cell line (by calcium phosphate precipitation for example), the Ψ sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., 1975).

An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

3. Adeno-associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, 1995; Chatterjee et al., 1995; Ferrari et al., 1996; Fisher et al., 1996; Flotte et al., 1993; Goodman et al., 1994; Kaplitt et al., 1994; 1996; Koeberl et al., 1997).

AAV-mediated efficient gene transfer and expression in the lung has led to clinical trials for the treatment of cystic fibrosis (Carter and Flotte, 1995; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996). 4. Other Viral Vectors Other viral vectors are employed as expression constructs in the present invention. Vectors derived from viruses such as vaccinia virus (Ridgeway, 1988; Baichwal and Sugden, 1986; Coupar et al., 1988) canary pox virus, and herpes viruses are employed. These viruses offer several features for use in gene transfer into various mammalian cells.

Once the construct has been delivered into the cell, the nucleic acid encoding the transgene are positioned and expressed at different sites. In certain embodiments, the nucleic acid encoding the transgene is stably integrated into the genome of the cell. This integration is in the cognate location and orientation via homologous recombination (gene replacement) or it is integrated in a random, non-specific location (gene augmentation). In yet further embodiments, the nucleic acid is stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

V. Mutagenesis, Peptidomimetics and Rational Drug Design

It will also be understood that this invention is not limited to the particular nucleic acid and amino acid sequences of the present invention. Recombinant vectors and isolated DNA segments may therefore variously include these coding regions themselves, coding regions bearing selected alterations or modifications in the basic coding region, or they may encode larger polypeptides that nevertheless include such coding regions or may encode biologically functional equivalent proteins, polypeptides or peptides that have variant amino acids sequences. These proteins, polypeptides or peptides with variant amino acid sequences may also include analogues or mutants that function as antagonistic proteins, polypeptides or peptides.

The DNA segments of the present invention encompass biologically functional equivalent OASL proteins, polypeptides, and peptides. Such sequences may arise as a consequence of codon redundancy and functional equivalency that are known to occur naturally within nucleic acid sequences and the proteinaceous compositions thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes may be introduced, for example, through the application of site-directed mutagenesis techniques as discussed herein below, i.e., to introduce improvements to the antigenicity of the proteinaceous composition or to test mutants in order to examine OASL6 activity at the molecular level.

Alternatively, DNA segments that encompass antagonistic OASL proteins, polypeptides, and peptides may be generated using non-conservative insertions, deletions and/or substitutions. These non-conservative changes in the DNA segments result in a protein, polypeptide, and peptide that exhibits antagonistic properties, such as inhibiting the function of OASL.

Site-specific mutagenesis is a technique useful in the preparation of individual peptides, antagonists, or biologically functional equivalent proteins, polypeptides or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double-stranded plasmids are also routinely employed in site directed mutagenesis, which eliminates the step of transferring the gene of interest from a phage to a plasmid.

Site-directed mutagenesis is performed by first obtaining a single-stranded vector, or melting of two strands of a double stranded vector, which includes within its sequence a DNA sequence encoding the desired proteinaceous molecule. An oligonucleotide primer bearing the desired mutated sequence is synthetically prepared. This primer is then annealed with the single-stranded DNA preparation, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

In addition to the OASL peptidyl compounds described herein, it is contemplated that other sterically similar compounds may be formulated to mimic the key portions of the peptide structure. Such compounds, which may be termed peptidomimetics, may be used in the same manner as the peptides of the invention and hence are also functional equivalents.

Certain mimetics that mimic elements of proteinaceous molecule's secondary structure are described in Johnson et al. (1993). The underlying rationale behind the use of peptide mimetics is that the peptide backbone of proteinaceous molecules exists chiefly to orientate amino acid side chains in such a way as to facilitate molecular interactions, such as those of antibody and antigen. A peptide mimetic is thus designed to permit molecular interactions similar to the natural molecule.

Some successful applications of the peptide mimetic concept have focused on mimetics of β-turns within proteinaceous molecules, which are known to be highly antigenic. Likely β-turn structure within a polypeptide can be predicted by computer-based algorithms, as discussed herein. Once the component amino acids of the turn are determined, mimetics can be constructed to achieve a similar spatial orientation of the essential elements of the amino acid side chains.

The generation of further structural equivalents or mimetics may be achieved by the techniques of modeling and chemical design known to those of skill in the art. The art of receptor modeling is now well known, and by such methods a chemical that binds OASL can be designed and then synthesized. It will be understood that all such sterically designed constructs fall within the scope of the present invention.

In one aspect, a compound may be designed by rational drug design to function as a modulator of 2', 5' oligoadenylate synthetase activity. These modulators may be agonists or antagonists. The goal of rational drug design is to produce structural analogs of biologically active compounds. By creating such analogs, it is possible to fashion drugs, which are more active or stable than the natural molecules, which have different susceptibility to alteration or which may affect the function of various other molecules. In one approach, one would generate a three-dimensional structure for the OASL protein of the invention or a fragment thereof. This could be accomplished by X-ray crystallography, computer modeling or by a combination of both approaches. An alternative approach, involves the random replacement of functional groups throughout the OASL protein, polypeptides or peptides, and the resulting affect on function determined.

It also is possible to isolate an OASL protein, polypeptide or peptide specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have enhanced and improved biological activity, for example, 2', 5' oligoadenylate synthetase activity, contraception, enhanced fertility, cell proliferative activity relative to a starting OASL protein sequences. Yet further, one may design drugs which do not have 2', 5' oligoadenylate synthetase activity or 2', 5' oligoadenylate synthetase activity can be modulated by chemical means. By virtue of the ability to recombinatly produce sufficient amounts of the OASL proteins, polypeptides or peptides, crystallographic studies may be preformed to determine the most likely sites for mutagenesis and chemical mimicry. In addition, knowledge of the chemical characteristics of these compounds permits computer employed predictions of structure-function relationships. Computer models of various polypeptide and peptide structures are also available in the literature or computer databases. In a non-limiting example, the Entrez database may be used by one of ordinary skill in the art to identify target sequences and regions for mutagenesis.

VI. Methods for Screening Modulators

The present invention also contemplates the use of OASL and active fragments, and nucleic acids coding thereof, in the screening of compounds for activity in either stimulating OASL activity, overcoming the lack of OASL or blocking or inhibiting the effect of an OASL molecule. These assays may make use of a variety of different formats and may depend on the kind of "activity" for which the screen is being conducted.

A. In vitro Assays

In one embodiment, the invention is to be applied for the screening of compounds that bind to the OASL polypeptide or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of OASL to a natural or artificial substrate or binding partner. Competitive binding assays can be performed in which one of the agents (OASL, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with OASL and washed. Bound polypeptide is detected by various methods.

Purified OASL can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the OASL active region to a solid phase.

Various cell lines containing wild-type or natural or engineered mutations in Oasl gene can be used to study various functional attributes of OASL and how a candidate compound affects these attributes. Methods for engineering mutations are described elsewhere in this document, as are naturally-occurring mutations in Oasl that lead to, contribute to and/or otherwise cause infertility. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of OASL, or related pathways, may be explored.

In a specific embodiment, yeast two-hybrid analysis is performed by standard means in the art with the polypeptides of the present invention, i.e., OASL. Two hybrid screen is used to elucidate or characterize the function of a protein by identifying other proteins with which it interacts. The protein of unknown function, herein referred to as the "bait" is produced as a chimeric protein additionally containing the DNA binding domain of GAL4. Plasmids containing nucleotide sequences which express this chimeric protein are transformed into yeast cells, which also contain a representative plasmid from a library containing the GAL4 activation domain fused to different nucleotide sequences encoding different potential target proteins. If the bait protein physically interacts with a target protein, the GAL4 activation domain and GAL4 DNA binding domain are tethered and are thereby able to act conjunctively to promote transcription of a reporter gene. If no interaction occurs between the bait protein and the potential target protein in a particular cell, the GAL4 components remain separate and unable to promote reporter gene transcription on their own. One skilled in the art is aware that different reporter genes can be utilized, including β-galactosidase, HIS3, ADE2, or URA3. Furthermore, multiple reporter sequences, each under the control of a different inducible promoter, can be utilized within the same cell to indicate interaction of the GAL4 components (and thus a specific bait and target protein). A skilled artisan is aware that use of multiple reporter sequences decreases the chances of obtaining false positive candidates. Also, alternative DNA-binding domain/activation domain components may be used, such as LexA. One skilled in the art is aware that any activation domain may be paired with any DNA binding domain so long as they are able to generate transactivation of a reporter gene. Furthermore, a skilled artisan is aware that either of the two components may be of prokaryotic origin, as long as the other component is present and they jointly allow transactivation of the reporter gene, as with the LexA system.

Two hybrid experimental reagents and design are well known to those skilled in the art (see The Yeast Two-Hybrid System by P. L. Bartel and S. Fields (eds.) (Oxford University Press, 1997), including the most updated improvements of the system (Fashena et al., 2000). A skilled artisan is aware of commercially available vectors, such as the Matchmaker™ Systems from Clontech (Palo Alto, Calif.) or the HybriZAP® 2.1 Two Hybrid System (Stratagene; La Jolla, Calif.), or vectors available through the research community (Yang et al., 1995; James et al., 1996). In alternative embodiments, organisms other than yeast are used for two hybrid analysis, such as mammals (Mammalian Two Hybrid Assay Kit from Stratagene (La Jolla, Calif.)) or *E. coli* (Hu et al., 2000).

In an alternative embodiment, a two hybrid system is utilized wherein protein-protein interactions are detected in a cytoplasmic-based assay. In this embodiment, proteins are expressed in the cytoplasm, which allows posttranslational modifications to occur and permits transcriptional activators and inhibitors to be used as bait in the screen. An example of such a system is the CytoTrap® Two-Hybrid System from Stratagene (La Jolla, Calif.), in which a target protein becomes anchored to a cell membrane of a yeast which contains a temperature sensitive mutation in the cdc25 gene, the yeast homologue for hSos (a guanyl nucleotide exchange factor). Upon binding of a bait protein to the target, hSos is localized to the membrane, which allows activation of RAS by promoting GDP/GTP exchange. RAS then activates a signaling cascade which allows growth at 37° C. of a mutant yeast cdc25H. Vectors (such as pMyr and psos) and other experimental details are available for this system to a skilled artisan through Stratagene (La Jolla, Calif.). (See also, for example, U.S. Pat. No. 5,776,689, herein incorporated by reference).

Thus, in accordance with an embodiment of the present invention, there is a method of screening for a peptide which interacts with OASL comprising introducing into a cell a first nucleic acid comprising a DNA segment encoding a test peptide, wherein the test peptide is fused to a DNA binding domain, and a second nucleic acid comprising a DNA segment encoding at least part of OASL6, respectively, wherein the at least part of OASL respectively, is fused to a DNA activation domain. Subsequently, there is an assay for interaction between the test peptide and the OASL polypeptide or fragment thereof by assaying for interaction between the DNA binding domain and the DNA activation domain. For example, the assay for interaction between the DNA binding and activation domains may be activation of expression of β-galactosidase.

An alternative method is screening of λgt11, λLZAP (Stratagene) or equivalent cDNA expression libraries with recombinant Oasl. Recombinant Oasl or fragments thereof are fused to small peptide tags such as FLAG, HSV or GST. The peptide tags can possess convenient phosphorylation sites for a kinase such as heart muscle creatine kinase or they can be biotinylated. Recombinant Oasl can be phosphorylated with $^{32}$[P] or used unlabeled and detected with streptavidin or antibodies against the tags λgt11cDNA expression libraries are made from cells of interest and are incubated with the recombinant Oasl, washed and cDNA clones which interact with Oasl isolated. Such methods are routinely used by skilled artisans. See, i.e., Sambrook (supra).

Another method is the screening of a mammalian expression library in which the cDNAs are cloned into a vector between a mammalian promoter and polyadenylation site and transiently transfected in cells. Forty-eight hours later the binding protein is detected by incubation of fixed and washed cells with a labeled Oasl. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing the Oasl bound to the plate. Cells which attach after washing are lysed and the plasmid DNA isolated, amplified in bacteria, and the cycle of transfection and panning repeated until a single CDNA clone is obtained. See Seed et al., 1987 and Aruffo et al., 1987 which are herein incorporated by reference. If the binding protein is secreted, its cDNA can be obtained by a similar pooling strategy once a binding or neutralizing assay has been established for assaying supernatants from transiently transfected cells. General methods for screening supernatants are disclosed in Wong et al., (1985).

Another alternative method is isolation of proteins interacting with the OASL directly from cells. Fusion proteins of OASL with GST or small peptide tags are made and immobilized on beads. Biosynthetically labeled or unlabeled protein extracts from the cells of interest are prepared, incubated with the beads and washed with buffer. Proteins interacting with the OASL are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another alternative method is immunoaffinity purification. Recombinant OASL is incubated with labeled or unlabeled cell extracts and immunoprecipitated with anti-OASL antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method is screening of peptide libraries for binding partners. Recombinant tagged or labeled OASL is used to select peptides from a peptide or phosphopeptide library which interact with the OASL. Sequencing of the peptides leads to identification of consensus peptide sequences which might be found in interacting proteins. Also, peptides may be selected that block OASL function.

B. In vivo Assays

The present invention also encompasses the use of various animal models. Thus, any identity seen between human and other animal OASL provides an excellent opportunity to examine the function of OASL in a whole animal system where it is normally expressed. By developing or isolating mutant cells lines that fail to express normal OASL, one can generate models in mice that enable one to study the mechanism of OASL and its role in oogenesis and embryonic development.

Treatment of animals with test compounds will involve the administration of the compound, in an appropriate form, to the animal. Administration will be by any route that could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous, intraovarian bursal, or intratesticular injection. Specifically contemplated are systemic intravenous injection, regional administration via blood or lymph supply and intratumoral injection.

Determining the effectiveness of a compound in vivo may involve a variety of different criteria. Such criteria include, but are not limited to, increased fertility, decreased fertility or contraception.

In one embodiment of the invention, transgenic animals are produced which contain a functional transgene encoding a functional OASL polypeptide or variants thereof. Transgenic animals expressing OASL transgenes, recombinant cell lines derived from such animals and transgenic embryos may be useful in methods for screening for and identifying agents that induce or repress function of OASL. Transgenic animals of the present invention also can be used as models for studying disease states.

In one embodiment of the invention, an Oasl transgene is introduced into a non-human host to produce a transgenic animal expressing OASL. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous Oasl gene or portion of the gene by homologous recombination between the transgene and the endogenous gene; or the endogenous gene may be eliminated by deletion as in the preparation of "knock-out" animals. Typically, targeting vectors that contain a portion of the gene of interest and a selection marker are generated and transfected into embryonic stem (ES) cells. These targeting vectors are electroporated into the hprt-negative ES cell line and selected in HAT and FIAU. ES cells can be selected in HAT, G418 or any other selection method depending on the selectable marker gene that is used. ES cells with the correct mutation are injected into blastocysts to generate chimeras and eventually heterozygotes and homozygotes for the mutant Oasl genes. Thus, the absence of Oasl in "knock-out" mice permits the study of the effects that loss of OASL protein has on a cell in vivo.

As noted above, transgenic animals and tissues, cells and cell lines derived from such animals may find use in certain testing experiments. In this regard, transgenic animals and cell lines capable of expressing wild-type or mutant Oasl or lacking a functional OASL gene may be exposed to test substances. These test substances can be screened for the ability to enhance wild-type Oasl expression and or function or impair the expression or function of mutant Oasl.

VII. Modulators of OASL

In certain embodiments, modulators of OASL are administered to an animal to either enhance or suppress the activity and/or expression of OASL. It is envisioned that OASL plays a role in mRNA degradation pathways important for gametogenesis or early embryonic development or cell proliferation.

The modulators of the present invention include, but are not limited to polynucleotides, polypeptides, antibodies, small molecules or other compositions that are capable of modulating either the activity and/or the expression of OASL.

A. Transcription Factors and Nuclear Binding Sites

Transcription factors are regulatory proteins that binds to a specific DNA sequence (i.e., promoters and enhancers) and regulate transcription of an encoding DNA region. Typically, a transcription factor comprises a binding domain that binds to DNA (a DNA binding domain) and a regulatory domain that controls transcription. Where a regulatory domain activates transcription, that regulatory domain is designated an activation domain. Where that regulatory domain inhibits transcription, that regulatory domain is designated a repression domain.

Activation domains, and more recently repression domains, have been demonstrated to function as independent, modular components of transcription factors. Activation domains are not typified by a single consensus sequence but instead fall into several discrete classes: for example, acidic domains in GAL4 (Ma, et al. 1987), GCN4 (Hope, et al., 1987), VP16 (Sadowski, et al. 1988), and GATA-1 (Martin, et al. 1990); glutamine-rich stretches in Sp1 (Courey, et al. 1988) and Oct-2/OTF2 (Muller-Immergluck, et al. 1990; Gerster, et al. 1990); proline-rich sequences in CTF/NF-1 (Mermod, et al. 1989); and serine/threonine-rich regions in Pit-1/GH-F-1 (Theill, et al. 1989) all function to activate transcription. The activation domains of fos and jun are rich in both acidic and proline residues (Abate, et al. 1991; Bohmann, et al. 1989); for other activators, like the CCAAT/enhancer-binding protein C/EBP (Friedman, et al. 1990), no evident sequence motif has emerged.

In the present invention, it is contemplated that transcription factors can be used to inhibit the expression of a Oasl gene. One such example is FIG alpha. FIG alpha (Soyal et al., 2000) is a germ cell-specific, basic helix-loop-helix factor. It has been suggested that FIG alpha plays a role in regulating ovarian development.

B. Antisense and Ribozymes

An antisense molecule that binds to a translational or transcriptional start site, or splice junctions, are ideal modulators. Antisense, ribozyme, and double-stranded RNA molecules target a particular sequence to achieve a reduction or elimination of a particular polypeptide, such as OASL or another protein that plays a role in modulating OASL. Thus, it is contemplated that antisense, ribozyme, and double-stranded RNA, and interference RNA molecules are constructed and used to modulate Oasl expression.

1. Antisense Molecules

Antisense methodology takes advantage of the fact that nucleic acids tend to pair with complementary sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, are employed to inhibit gene transcription or translation or both within a host cell, either in vitro or in vivo, such as within a host animal, including a human subject.

Antisense constructs are designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50–200 bases of an intron-exon splice junction are used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

It is advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

2. Ribozymes

Ribozymes are RNA-protein complexes that cleave nucleic acids in a site-specific fashion. Ribozymes have specific catalytic domains that possess endonuclease activity (Kim and Cech, 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al, 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression is particularly suited to therapeutic applications (Scanlon et al, 1991; Sarver et al., 1990; Sioud et al, 1992). Most of this work involved the modification of a target mRNA, based on a specific mutant codon that is cleaved by a specific ribozyme. In light of the information included herein and the knowledge of one of ordinary skill in the art, the preparation and use of additional ribozymes that are specifically targeted to a given gene will now be straightforward.

Other suitable ribozymes include sequences from RNase P with RNA cleavage activity (Yuan et al, 1992; Yuan and Altman, 1994), hairpin ribozyme structures (Berzal-Herranz et al, 1992; Chowrira et al, 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al, 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A,C or U; Perriman, et al., 1992; Thompson, et al., 1995). The frequency of this dinucleotide occurring in any given RNA is statistically 3 out of 16.

Designing and testing ribozymes for efficient cleavage of a target RNA is a process well known to those skilled in the art. Examples of scientific methods for designing and testing ribozymes are described by Chowrira et al. (1994) and Lieber and Strauss (1995), each incorporated by reference. The identification of operative and preferred sequences for use in OASL targeted ribozymes is simply a matter of preparing and testing a given sequence, and is a routinely practiced screening method known to those of skill in the art.

3. RNA Interference

It is also contemplated in the present invention that double-stranded RNA is used as an interference molecule, i.e., RNA interference (iRNA).

RNA interference is used to "knock out" or inhibit a particular gene of interest by simply injecting, bathing or feeding to the organism of interest a double-stranded RNA molecule. This technique selectively "knock outs" gene function without requiring transfection or recombinant techniques (Giet, 2001; Hammond, 2001).

Thus, in certain embodiments, double-stranded Oasl RNA is synthesized or produced using standard molecular techniques described herein. In further embodiments, double-stranded RNA molecules of other compositions that may inhibit Oasl are also considered and used herein, such as compositions that can enhance the activity of OASL.

VIII. Diagnosing Infertility

Oasl genes may be employed as a diagnostic or prognostic indicator of infertility in general. More specifically, point mutations, deletions, insertions or regulatory perturbations will be identified. The present invention contemplates further the diagnosis of infertility detecting changes in the levels of Oasl expression.

A. Genetic Diagnosis

One embodiment of the present invention comprises a method for detecting variation in the expression of Oasl. This may comprise determining the level of Oasl expressed, or determining specific alterations in the expressed product. In specific embodiments, alterations are detected in the expression of Oasl6.

The biological sample can be tissue or fluid. Various embodiments include cells from the testes and ovaries. Other embodiments include fluid samples such as vaginal fluid or seminal fluid.

Nucleic acids used are isolated from cells contained in the biological sample, according to standard methodologies (Sambrook et al, 1989). The nucleic acid may be genomic DNA or fractionated or whole cell RNA. Where RNA is used, it may be desired to convert the RNA to a complementary DNA (cDNA). In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (i.e., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have been diagnosed with infertility.

It is contemplated that other mutations in the Oasl gene may be identified in accordance with the present invention by detecting a nucleotide change in particular nucleic acids (U.S. Pat. No. 4,988,617, incorporated herein by reference). A variety of different assays are contemplated in this regard, including but not limited to, fluorescent in situ hybridization (FISH; U.S. Pat. No. 5,633,365 and U.S. Pat. No. 5,665,549, each incorporated herein by reference), direct DNA sequencing, PFGE analysis, Southern or Northern blotting, single-stranded conformation analysis (SSCA), RNAse protection assay, allele-specific oligonucleotide (ASO, i.e., U.S. Pat. No. 5,639,611), dot blot analysis, denaturing gradient gel electrophoresis (i.e., U.S. Pat. No. 5,190,856 incorporated herein by reference), RFLP (i.e., U.S. Pat. No. 5,324,631 incorporated herein by reference) and PCR™-SSCP. Methods for detecting and quantitating gene sequences, such as mutated genes and oncogenes, in for example biological fluids are described in U.S. Pat. No. 5,496,699, incorporated herein by reference.

Yet further, it is contemplated by that chip-based DNA technologies such as those described by Hacia et al. (1996) and Shoemaker et al. (1996) can be used for diagnosis of infertility. Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al., (1994); Fodor et al., (1991).

B. Immunodiagnosis

Antibodies can be used in characterizing the OASL content through techniques such as ELISAs and Western blotting. This may provide a prenatal screen or in counseling for those individuals seeking to have children.

The steps of various other useful immunodetection methods have been described in the scientific literature, such as, i.e., Nakamura et al., (1987). Immunoassays, in their most simple and direct sense, are binding assays. Certain preferred immunoassays are the various types of radioimmunoassays (RIA) and immunobead capture assay. Immunohistochemical detection using tissue sections also is particularly useful. However, it will be readily appreciated that detection is not limited to such techniques, and Western blotting, dot blotting, FACS analyses, and the like also may be used in connection with the present invention.

The antibody compositions of the present invention will find great use in immunoblot or Western blot analysis. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art.

IX. Methods for Treating

A. Fertility and Contraception

The present invention contemplates the use of a modulator of OASL to either enhance contraception or fertility of an animal. Animals that are treated include, but are not limited to mammals or avian, for example, mice, rats, or monkeys are used as experimental animal models. In specific embodiments, the present invention is used to treat humans. It is also envisioned that companion animals can be treated for infertility or the prophylactic compositions can be used as a contraceptive. Companion animals include, but are not limited to, dogs, cats, horses, or birds.

The present invention involves the method of administering a composition to animal in an amount to result in contraception or fertility. Thus, contraception involves the administration of a compound in an effective amount such that the amount decreases conception. In the present invention, any modulation or decrease in conception is considered contraception. Yet further, an amount of a compound that results in an increase in fertility is considered the effective amount.

In certain embodiments of the present invention, an effective amount of a modulator of OASL is administered to an animal to enhance contraception by decreasing mRNA degradation. It is envisioned that inhibition of MRNA degradation of specific transcripts results in infertility. It is contemplated that a decrease in mRNA degradation during oocyte maturation results in an increase in transcripts, such as Mos and Plat. An increase in transcripts that are normally degraded during maturation results in an increase in mutations in the mature egg.

In certain embodiments of the present invention, an effective amount of a modulator of OASL is administered to an animal to enhance contraception. It is envisioned that OASL can play a role in the OAS pathway. It is contemplated that an increase in OASL may inhibit OAS activity or my enhance OAS activity. In an alternative, a decrease in OASL may inhibit or enhance OAS activity.

In additional embodiments, an effective amount of a modulator of OASL is administered to an animal to enhance fertility. It is envisioned that either an increase or a decrease in OASL can result in enhancement in fertility. Fertility is the opposite of infertility or contraception. If OASL is responsible for mRNA degradation of specific transcripts, then an increase in OASL can result in an increase in fertility.

In specific embodiments it is envisioned that an OASL polynucleotide, polypeptide or fragment thereof may interact with a polynucleotide or polypeptide of OAS. It is envisioned that the OASL polynucleotide is an antagonist of the OAS. For example, an OASL polynucleotide selected from the group consisting of SEQ. ID. NO.1, SEQ. ID. NO.3, SEQ. ID. NO.5, SEQ. ID. NO.7, SEQ. ID. NO.9, and SEQ. ID. NO.11 is an antagonist of SEQ. ID. NO.23, SEQ. ID. NO.25 or SEQ. ID. NO.27. Yet further, an OASL polynucleotide can be an antagonist of SEQ. ID. NO.24, SEQ. ID. NO.26 or SEQ. ID. NO.28. Thus, OASL polynucleotide, polypeptide, variant or fragment thereof may bind to an OAS polypeptide or polynucleotide and modulate OAS activity, such as block transcription, block translation, block interactions with other polynucleotides and/or polypeptides, etc. Yet further, OASL can modulate OAS activity by increasing or enhancing OAS transcription, translation, etc.

1. Genetic Based Therapies

Specifically, the present inventors intend to provide, to a cell, an expression construct capable of enhancing or decreasing OASL to that cell. Because the sequence homology between the human and other OASL related proteins, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpes virus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

2. Protein Therapy

Another therapy approach is the provision, to a subject, of OASL polypeptide, active fragments, synthetic peptides, mimetics or other analogs thereof. The protein may be produced by recombinant expression means. Formulations would be selected based on the route of administration and purpose including, but not limited to, liposomal formulations and classic pharmaceutical preparations.

A further protein therapy comprises, immunocontraceptive methods. Immunocontracetives comprise administering either antibodies to the reproductive antigen of interest or by developing a natural immune response to the administered reproductive antigen.

B. Hyperproliferative Diseases

In certain embodiments, a hyperproliferative disease may be treated by administering to a subject an effective amount of a modulator of OASL activity. The subject is preferably a mammal and more preferably a human.

In the present invention, a hyperproliferative disease is further defined as cancer. In still further embodiments, the cancer is melanoma, non-small cell lung, small-cell lung, lung, leukemia, hepatocarcinoma, retinoblastoma, astrocytoma, glioblastoma, gum, tongue, neuroblastoma, head, neck, breast, pancreatic, prostate, renal, bone, testicular, ovarian, mesothelioma, cervical, gastrointestinal, lymphoma, brain, colon, sarcoma or bladder.

The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell.

In other embodiments, the hyperproliferative disease is benign prostatic hypertrophy, neurofibromatosis, rheumatoid arthritis, Waginer's granulomatosis, Kawasaki's disease, lupus erathematosis, midline granuloma, inflammatory bowel disease, osteoarthritis, leiomyomas, adenomas, lipomas, hemangiomas, fibromas, vascular occlusion, restenosis, atherosclerosis, pre-neoplastic lesions, carcinoma in situ, oral hairy leukoplakia, psoriasis, pre-leukemias, anemia with excess blasts, and mylodysplastic syndrome.

In order to increase the effectiveness of the composition of the present invention, it may be desirable to combine the composition of the present invention with other agents effective in the treatment of hyperproliferative disease, such as anti-cancer agents, or with surgery. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the OASL modulator and the agent(s) or multiple factor(s) at the same time. This may be achieved by contacting the cell with a single composition or pharmacological formulation that includes both agents, or by contacting the cell with two distinct compositions or formulations, at the same time, wherein one composition includes OASL modulator and the other includes the second agent(s).

Alternatively, the OASL modulator of the present invention may precede or follow the other anti-cancer agent treatment by intervals ranging from minutes to weeks. In embodiments where the other anti-cancer agent and OASL modulator are applied separately to the cell, one would generally ensure that a significant period of time did not expire between the time of each delivery, such that the agent and OASL modulator would still be able to exert an advantageously combined effect on the cell. In such instances, it is contemplated that one may contact the cell with both modalities within about 12–24 hours of each other and, more preferably, within about 6–12 hours of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

X. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580).

Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

XI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Subtractive Hybridization

Using a physical subtractive hybridization approach, novel proteins that share homology with a 2', 5'-oligoadenylate synthetases (OAS), which induces RNA degradation, were cloned. These proteins include OASL6 (SEQ. ID. NO.2), OASL7 (SEQ. ID. NO.4), OASL8 (SEQ. ID. NO.6), OASL9 (SEQ. ID. NO.8), OASL10 (SEQ. ID. NO.10), and OASL11 (SEQ. ID. NO.12).

Briefly, a subtractive hybridization library was created. The library was enriched in sequences from the ovaries of growth differentiation factor-9 (Gdf9) knockout mice compared to ovaries from wild-type mice. Because the Gdf9 knockout ovaries have a block at the one-layer primary follicle stage, there was a relative increase in the number of fully-grown oocytes in these ovaries compared to controls. Sequences were analyzed to determine if they were in the public database and if they were ovary specific.

Example 2

Sequence Analysis

Figure 1A:
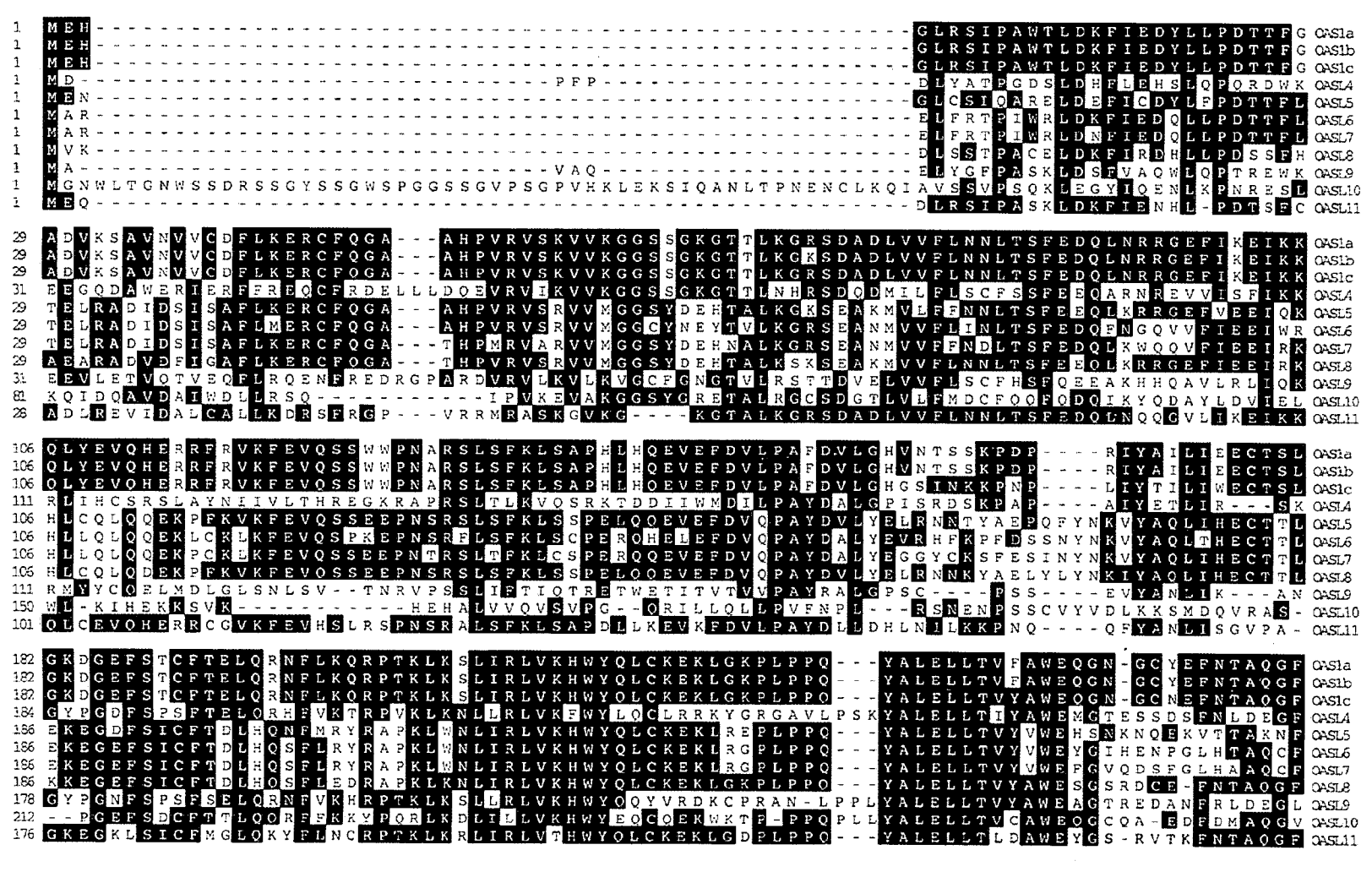
Figure 1C:
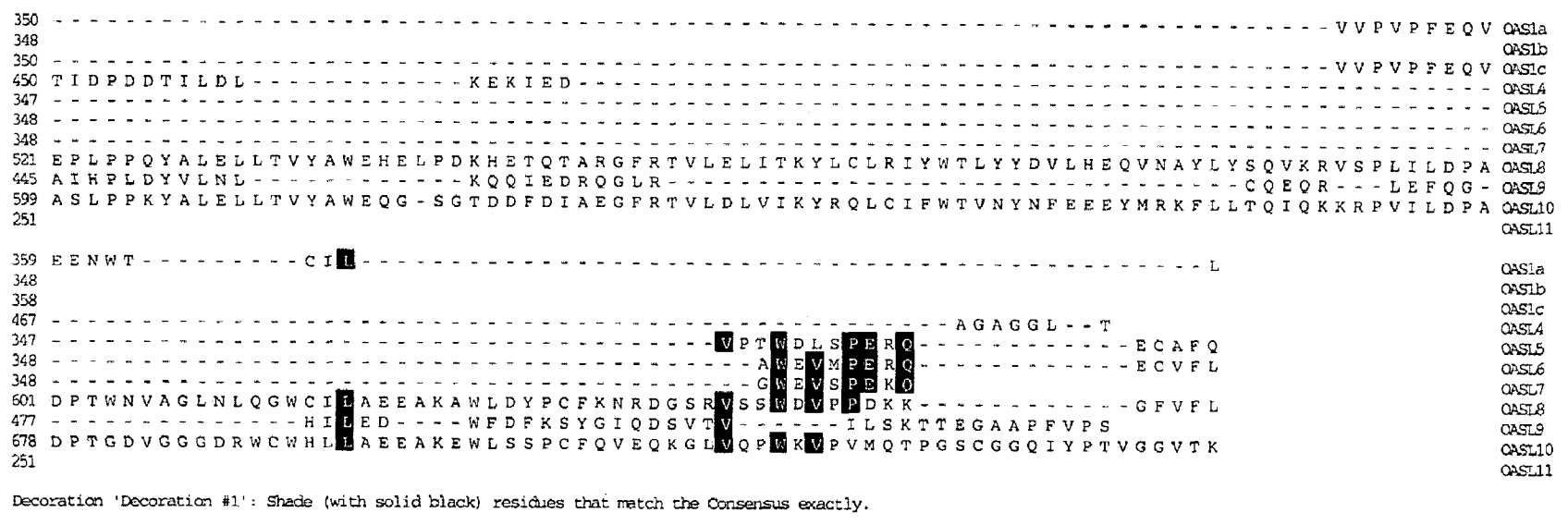
Figure 2A:
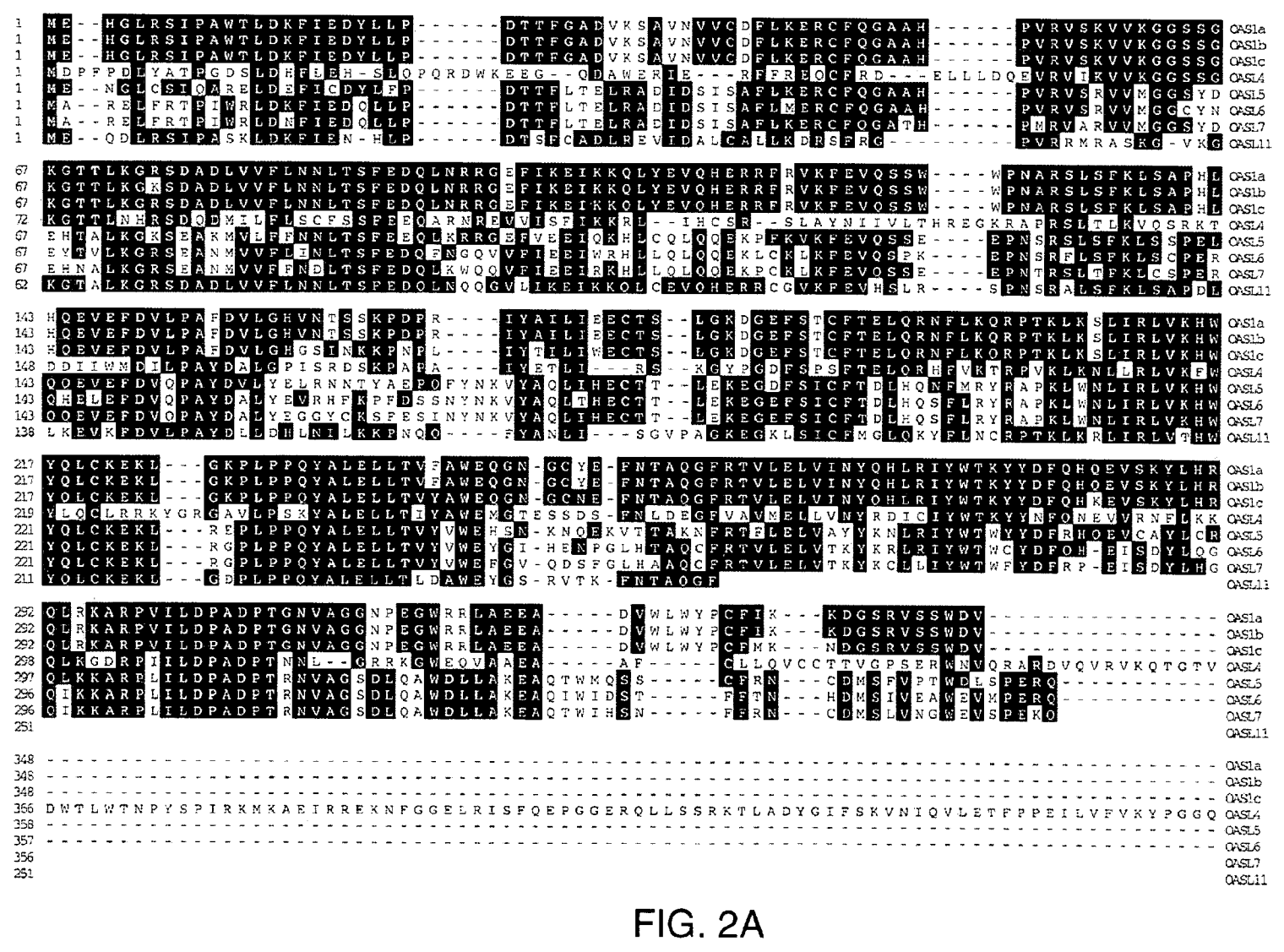
Figure 3A:
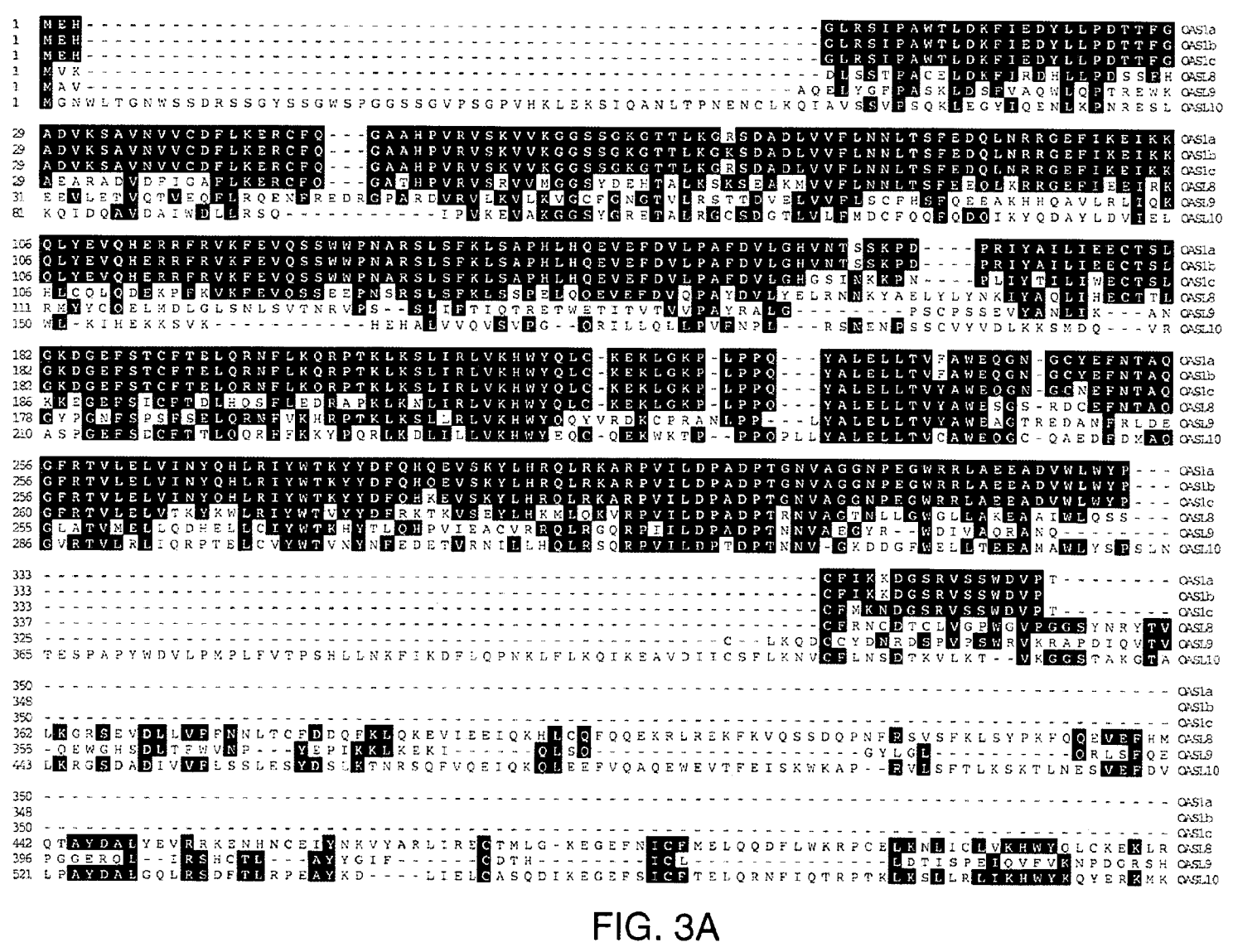
Figure 3B:
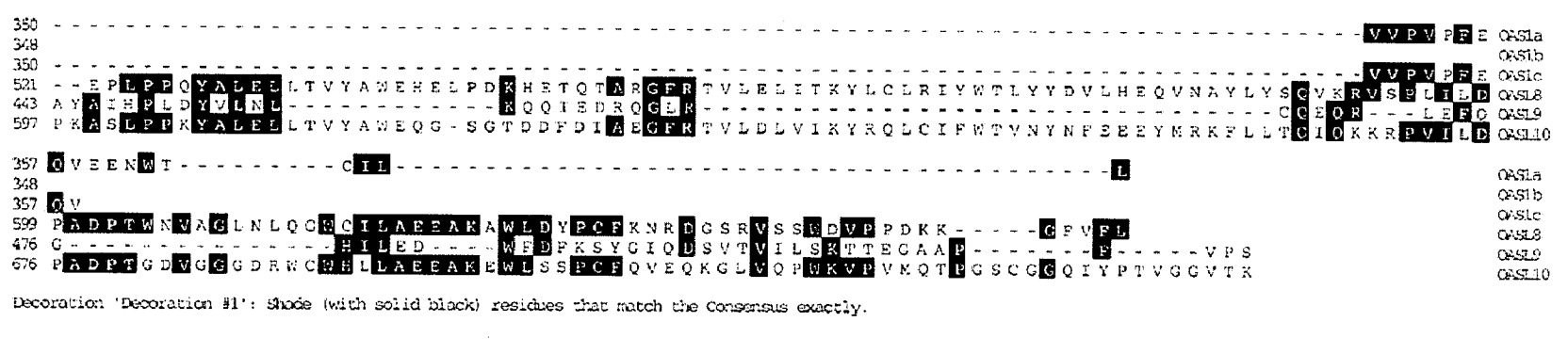
Figure 5:
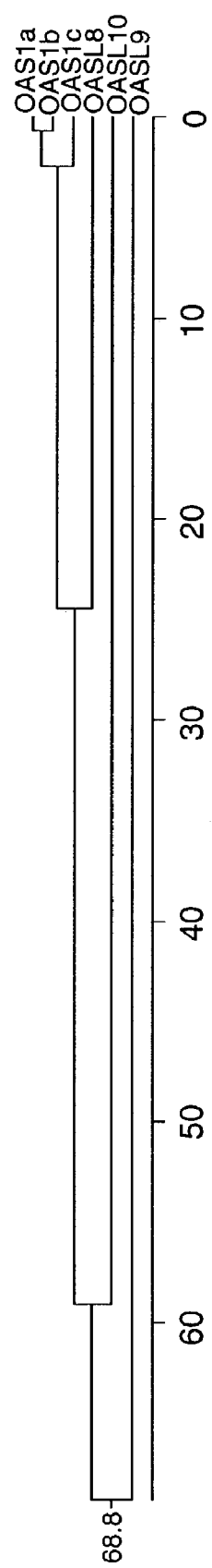
FIG. 5 shows a phylogenetic analysis of murine OAS1a–c, and OASL8–10 proteins.

Mouse Oasl6 (SEQ. ID. NO.1), Oasl7 (SEQ. ID. NO.3), Oasl8 (SEQ. ID. NO.5), Oasl9 (SEQ. ID. NO.7), Oasl10 (SEQ. ID. NO.9), and Oasl11 (SEQ. ID. NO.11) sequences were analyzed using several databases. The sequences were characterized using Clustal method with PAM250 residue weight table to compare the sequences to known protein sequences and to predict functional domains. FIG. 1 shows a multiple alignment analysis of OAS and OASL proteins. FIG. 2 shows a multiple alignment analysis of OAS1a–c, OASL4–7 and OASL11 proteins. FIG. 3 shows a multiple alignment analysis of OAS1a–c and OASL8–10 proteins. The conserved residues are shaded. FIG. 4 shows a phylogenetic analysis of OAS1a–c, OASL4–7 and OASL11 proteins. FIG. 5 shows a phylogenetic analysis of OAS1a–c and OASL8–10 proteins.

Figure 6:
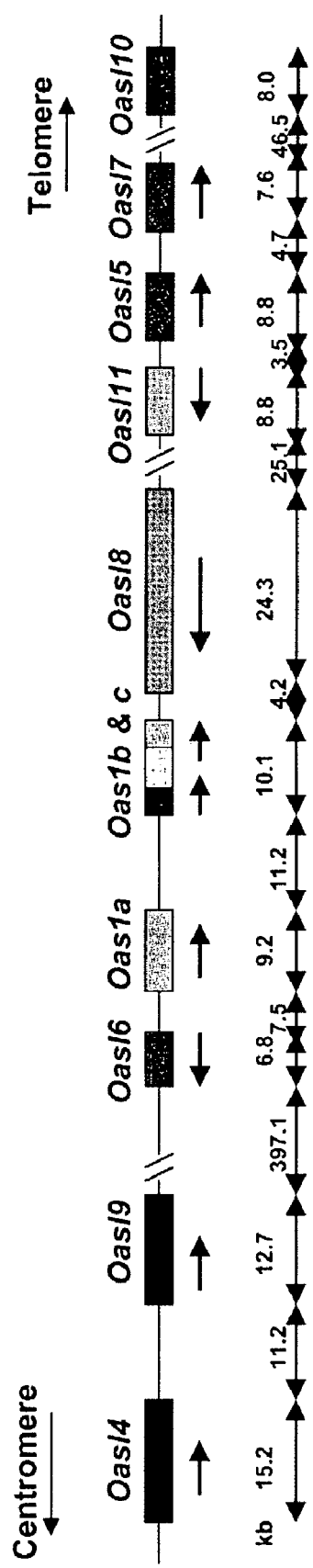
FIG. 6 shows a schematic presentation of chromosomal localization of 11 2',5'-oligoadenylate synthetase-like genes on mouse chromosome 5. Arrows indicate the transcriptional orientation of genes. Numbers in the lower panel present the distances between Oas1 genes.

FIG. 6 shows a schematic presentation of chromosomal localization of 11 2', 5'-oligoadenylate synthetase-like genes on the mouse chromosome. From the sequence analysis, the data showed that the full-length Oasl6 cDNA was shown to encode a 362 amino acid protein with 59% identity with mouse 2', 5'-oligoadenylate synthetase (OAS1) and 72% identity with the OAS-like protein OASL5. Oasl6 gene has 6 exons and was localized on chromosome 5, which is syntenic with human chromosome 12, a region that contains the human OAS family gene cluster. Thus, the data suggested that the genes encoding OASL5 and OASL6 in mouse and human are physically linked.

Example 3 mRNA Tissue Expression

Figure 7:
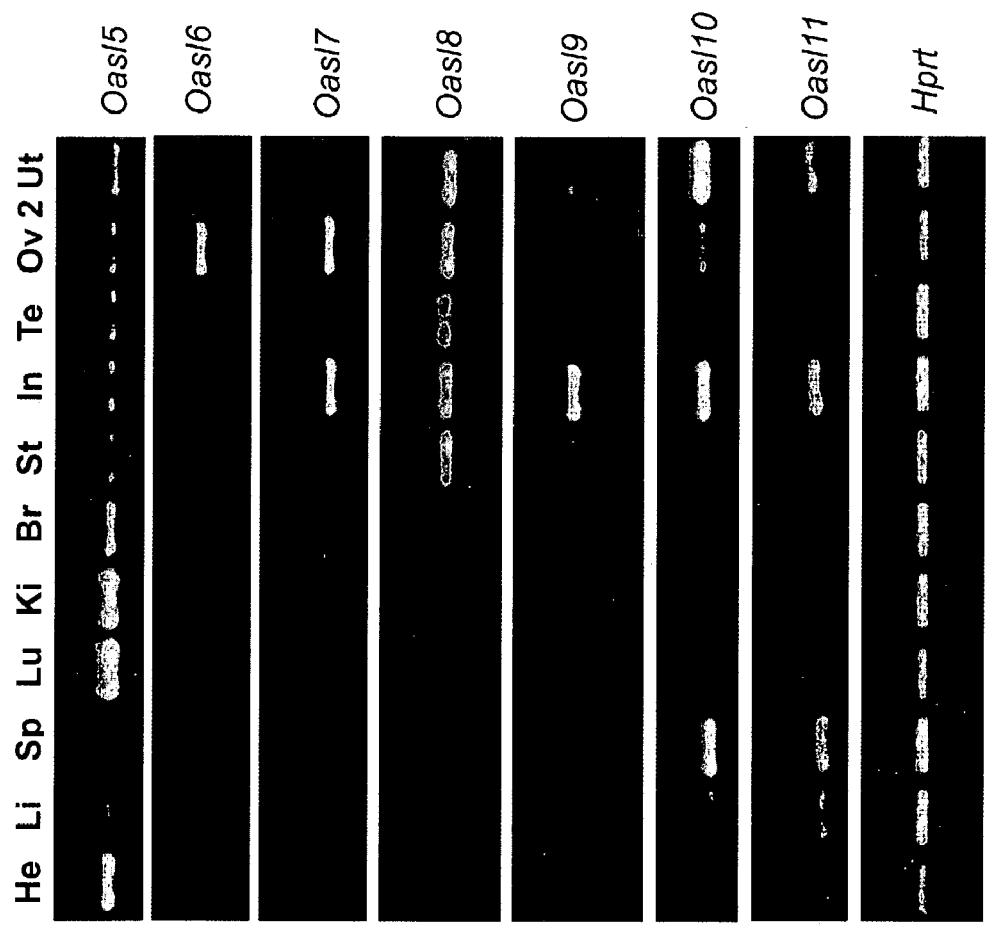
FIG. 7 shows a semi-quantitative RT-PCR analysis of mRNA expression of Oasl5–11 in multiple mouse tissues. Tissues include heart (He), liver (Li), spleen (Sp), kidney (Ki), brain (Br), stomach (St), small intestine (In), testis (Te), ovary (OV), and uterus (Ut).

Semi-quantitative RT-PCR analysis of mRNA expression of Oasl5–11 was performed using multiple mouse tissues. Primers were designed so that they all encompassed at least one intron and had no cross amplification among the Oasl homologs. Mouse Hprt was used as a control for monitoring equal input of cDNAs. To reveal the expression of these Oasl transcripts to the maximum extend, 40 cycles of PCR were performed. Mouse Hprt were amplified for 20 cycles to ensure the PCR was in exponential phase. FIG. 7 shows the analysis of mRNA expression in multiple tissues, which included heart (He), liver (Li), spleen (Sp), kidney (Ki), brain (Br), stomach (St), small intestine (In), testis (Te), ovary (OV), and uterus (Ut). As shown in FIG. 7, Oasl6, Oasl7 and Oasl8 were expressed in the ovaries and Oasl5 and Oasl10 were slightly expressed in the ovaries.

Example 4 mRNA Expression of Oasl6

Northern blot analysis was performed using standard techniques well known and used in the art. RNA was isolated from the following tissues: ovaries, brain, lung, heart, stomach, spleen, liver, small intestine, kidney, testes, and uterus. RNA was prepared using RNA STAT-60 (Leedo Medical Laboratories, Inc., Houston, Tex.) according to the manufacturer's instructions. Agarose gel electrophoresis of RNA, transfer to nylon membranes, and subsequent hybridization were performed by standard methods (Sambrook et al., 1989). RNA was also isolated from Ovaries of GDF9-/- mice.

Figure 8:
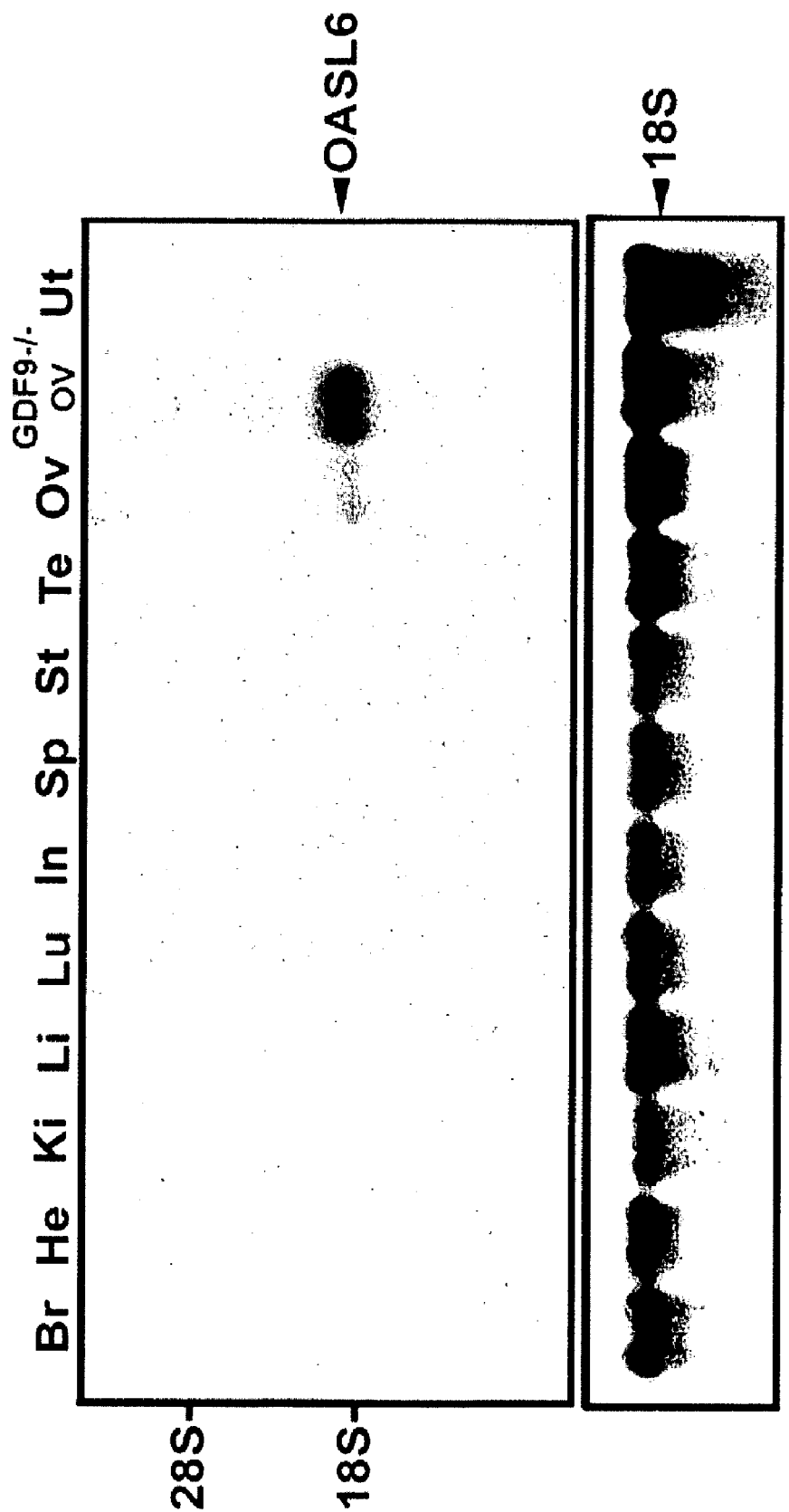
FIG. 8 shows mRNA expression of Oasl6 in multiple mouse tissues measured by Northern Blot analysis. Tissues include heart (He), liver (Li), spleen (Sp), kidney (Ki), brain (Br), stomach (St), small intestine (In), testis (Te), ovary (OV), and uterus (Ut).

As shown in FIG. 8, Oasl6 was exclusively expressed in the ovary. Thus, Oasl6 is an ovary-specific gene.

Example 5 mRNA Tissue Expression of Oas1 and Oasl6

To confirm that Oasl6 is exclusively expressed in the ovary, semi-quantitative RT-PCR analysis of mRNA expression of Oas1 and Oasl6 was performed. Reverse transcription and PCR reactions were performed as described by (Yan W. et. al., 2002). The primers used for amplifying Oasl6 are: (SEQ. ID. NO.29 5'-CTTTTCAGCAGTGCATGTGG-3'; SEQ. ID. NO.30 5'-TTCAATGCGTTTTGCTTTAATTT-3'. Primers for Oas1 are: SEQ. ID. NO.31 5'-CGTCTTG-GAACTGGTCATCA-3'; SEQ. ID. NO.32 5'-GGCACCT-GCTGTGGTTTATT-3'. Mouse Hprt was used as a control for monitoring equal input of cDNAs. To reveal the expression of these Oasl transcripts to the maximum extend, thirty-five cycles for Oasl6, 30 cycles for Oas1, and 20 cycles for Hprt (94 C denaturation for 15 min followed by cycling at 94 C, 30 sec, 59 C, 30 sec, and 72 C, 1 min; the last extension at 72 C for 10 min).

Figure 9:
FIG. 9 shows RT-PCR analysis of Oasl6 and Oas1 mRNA expression in multiple tissues. Tissues include heart (He), liver (Li), spleen (Sp), kidney (Ki), brain (Br), stomach (St), small intestine (In), testis (Te), ovary (OV), and uterus (Ut).

As shown in FIG. 9, Oas1 was ubiquitously expressed in multiple mouse tissues, whereas Oasl6 was exclusively expressed in the ovary. Thus, Oasl6 is an ovary-specific gene.

Example 6

Inducibility of Oasl

Inducibility of Oasl mRNA expressions was determined in multiple mouse tissues by Poly [I:C] treatment. Poly [I:C] is a synthetic dsRNA that is known to act as an interferon inducer.

Figure 10A:
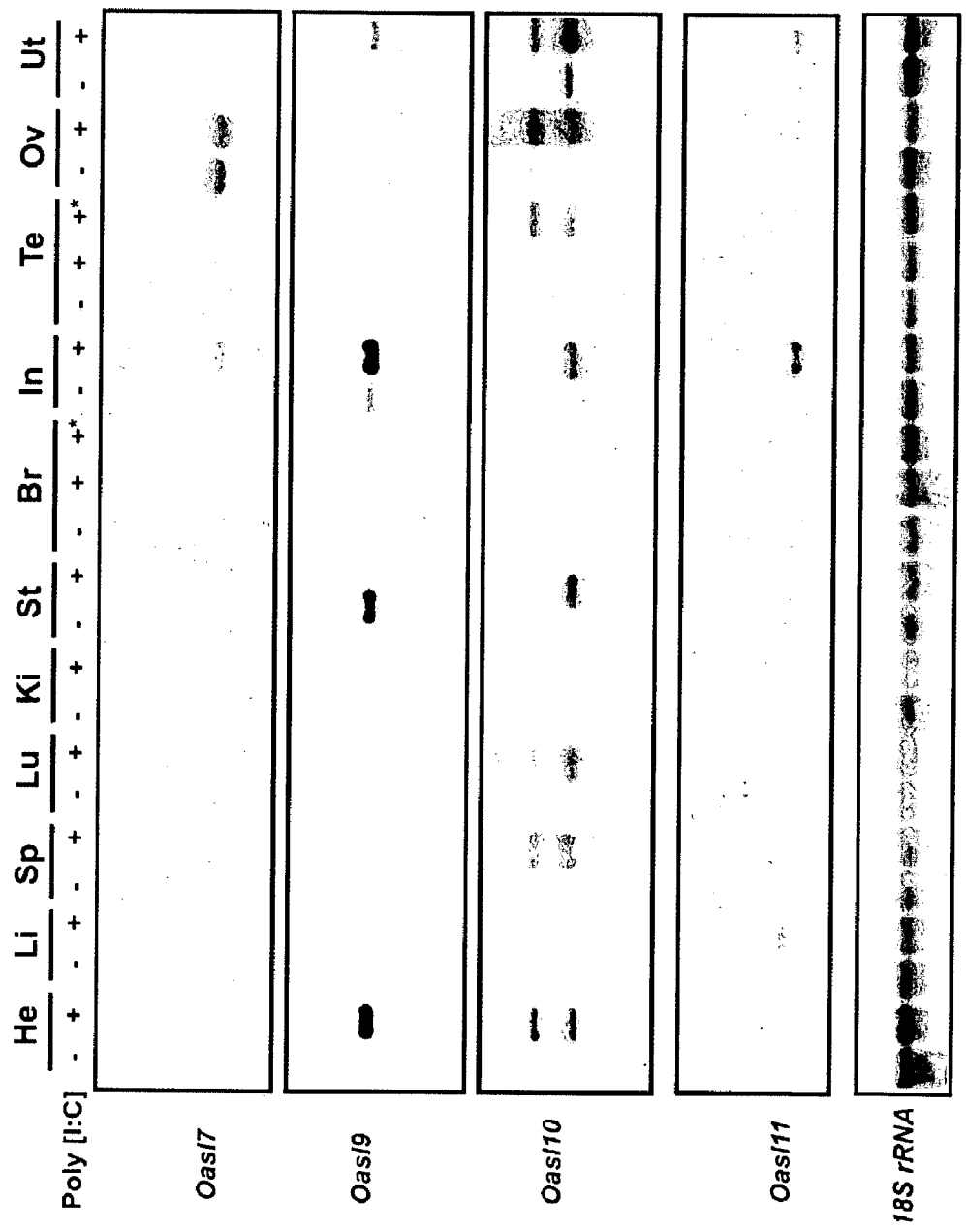
FIG. 10A and FIG. 10B show the inducibility of Oasl mRNA expressions in multiple mouse tissues by Poly [I:C] treatment.

Briefly, mice were i.p. injected with 250 µg of poly [I:C]. Tissues were collected after 24 hours. Control mice were injected with vehicle (PBS). Northern Blot analysis of Oasl MRNA levels in multiple tissues of Poly [I:C]-treated (+) and control (−) mice (FIG. 10A). The data revealed that Oasl7 and Oasl10 was induced by the presence of dsRNA in the ovary.

Figure 10B:
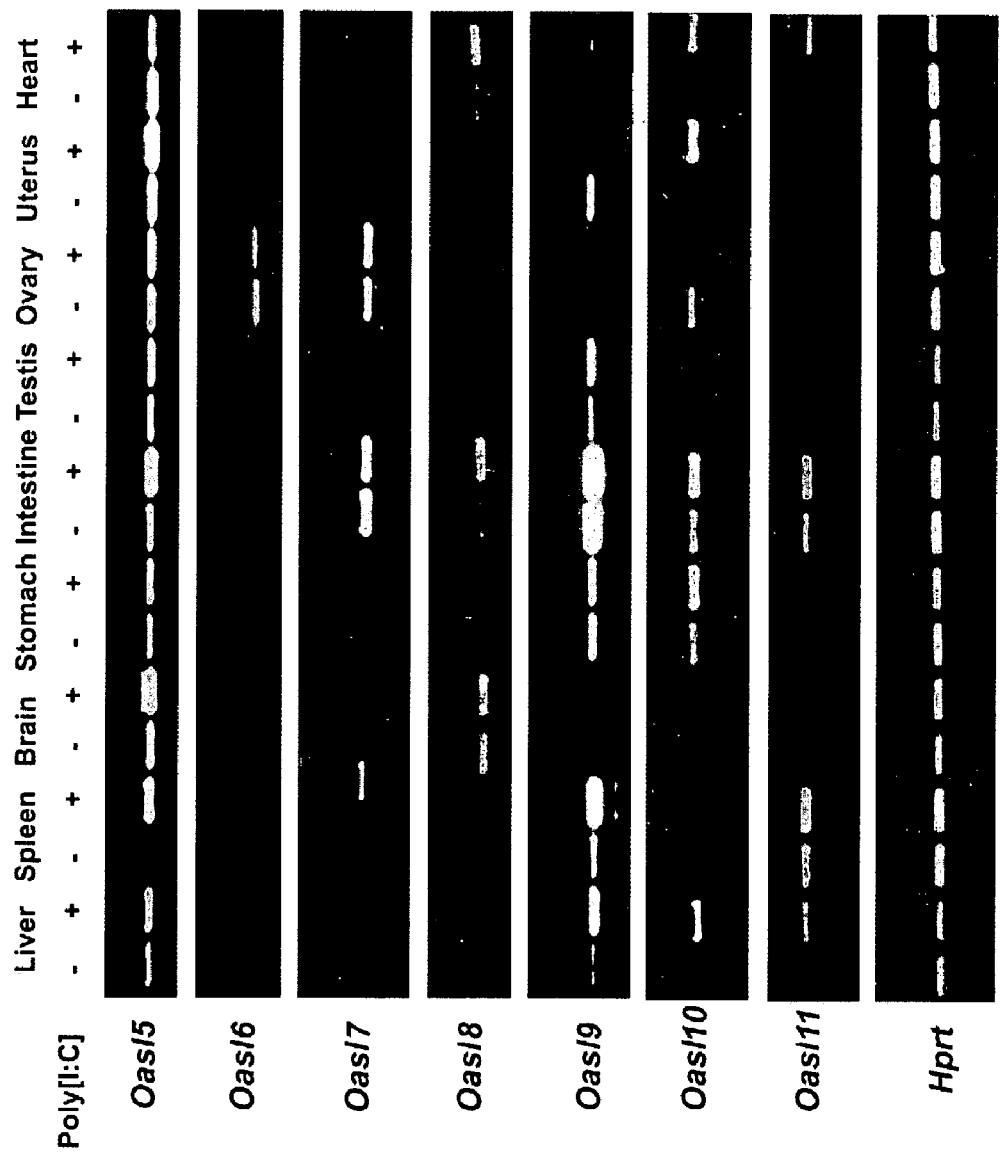

Next, semi-quantitative PCR analysis of Oasl mRNA expression was performed in multiple tissues of Poly [I:C]-treated and control mice (FIG. 10B). Mouse Hprt was used as control for monitoring equal input of cDNA. Primers were designed so that they all encompassed at least one intron and have no cross amplification among the Oasl homologs. To reveal the expression of these Oasl transcripts to the maximum extend, 40 cycles of PCR were performed. Mouse Hprt was amplified for 20 cycles to ensure the PCR was in exponential phase. The data revealed that Oasl5, Oasl7 was expressed in the ovaries in the presence and absence of poly [I:C] and Oasl10 expression was induced by the presence of dsRNA in the ovary.

Example 7 mRNA Expression in Prostate Tissue

Figure 11:
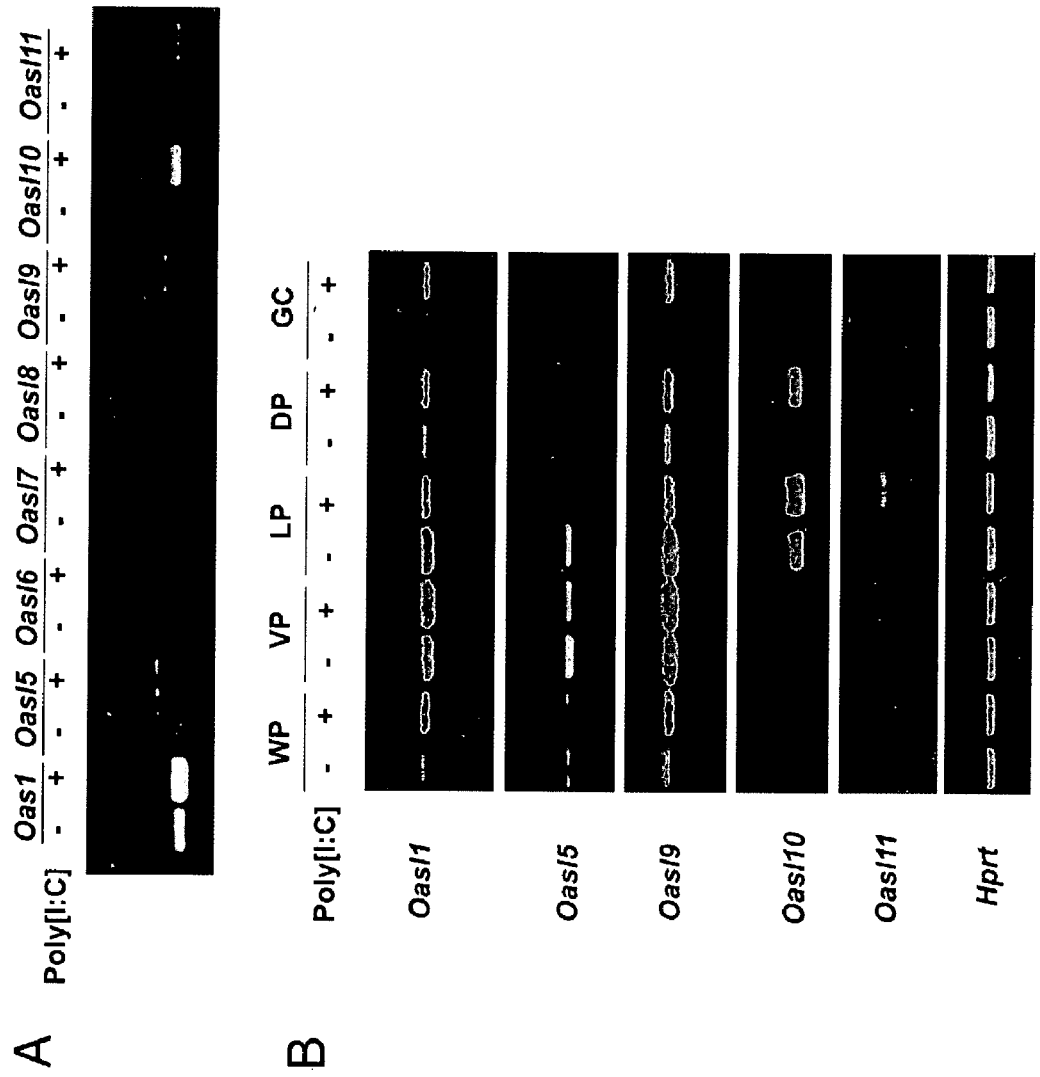
FIG. 11A and FIG. 11B show RT-PCR analysis of Oasl mRNAs in prostate.

RT-PCR analysis of Oasl mRNAs in prostate was performed. Mice were treated with 250 µg of poly [I:C] via i.p. injection. Prostates were collected after 24 hours. Control mice were injected with vehicle (PBS). Total RNA was isolated using an acid guanidinium thiocyanate-phenol-chloroform extraction (Leedo Medical Laboratories, Houston, Tex.). An aliquot of 2 µg of total RNA was reverse transcribed and then the resultant cDNAs were used for PCR amplification. Forty-five cycles of PCR were performed (FIG. 11A). FIG. 11A shows that Oasl1 was expressed in prostates in the presence and absence of poly [I:C] and Oasl10 expression was induced in the presence of poly [I:C].

FIG. 11B shows total RNAs isolated from whole prostate (WP), ventral prostate (VP), lateral prostate (LP), dorsal prostate (DP), and coagulating gland (GC) of Poly[I:C]-treated (+) or control (−) mice. Mouse Hprt was amplified to serve as a control for monitoring equal input of CDNA.

It is known that OAS proteins convert ATP into 2–5A oligomers which activate RNAse L resulting in a degradation of protein. It is also known that mutations, such as germline mutations, in RNAse L gene that result in a decrease in activity may be associated with prostate cancer (Carpten et al., 2002). Thus, the data suggested that the OASL proteins can act as negative regulators in the RNA degradation pathway.

Example 8

Regulation of Oas1 and Oasl6 mRNA by poly[I:C].

Northern blot analysis of Oas1 mRNA expression was performed in multiple tissues of Poly[I:C]-treated and control mice.

Adult (3–4 months) C57/S129SvEv (hybrid) mice (3 males and 3 females) received i.p. injection of 40 µg of Poly [I:C] dissolved in 0.9% NaCl (+). Control animals were given 0.9% NaCl only (−). Because of the blood-testis and blood-brain barrier, we also injected 10 µg directly into the testis (Te, +*) or brain (Br, +*). Control mice were injected with vehicle (PBS). Tissues (heart (He), liver (Li), spleen (Sp), kidney (Ki), brain (Br), stomach (St), small intestine (In), testis (Te), ovary (OV), and uterus (Ut)) were collected after 24 hours. RNA was prepared using RNA STAT-60 (Leedo Medical Laboratories, Inc., Houston, Tex.) according to the manufacturer's instructions. Total RNA (10 µg) was fractionated on 1.2% formaldehyde-agarose gels and transferred to Hybon-N nylon membrane (Amersham, Arlington Heights, Ill.). A 421 bp PCR fragment from the 3'-UTR of Oasl6 (corresponding to n.t. 1123-1543) was labeled with [α-$^{32}$P] dATP using a Strip-EZ kit (Ambion, Inc., Austin, Tex.). Blots were stripped and hybridized with an 18S rRNA cDNA for loading control.

Figure 12:
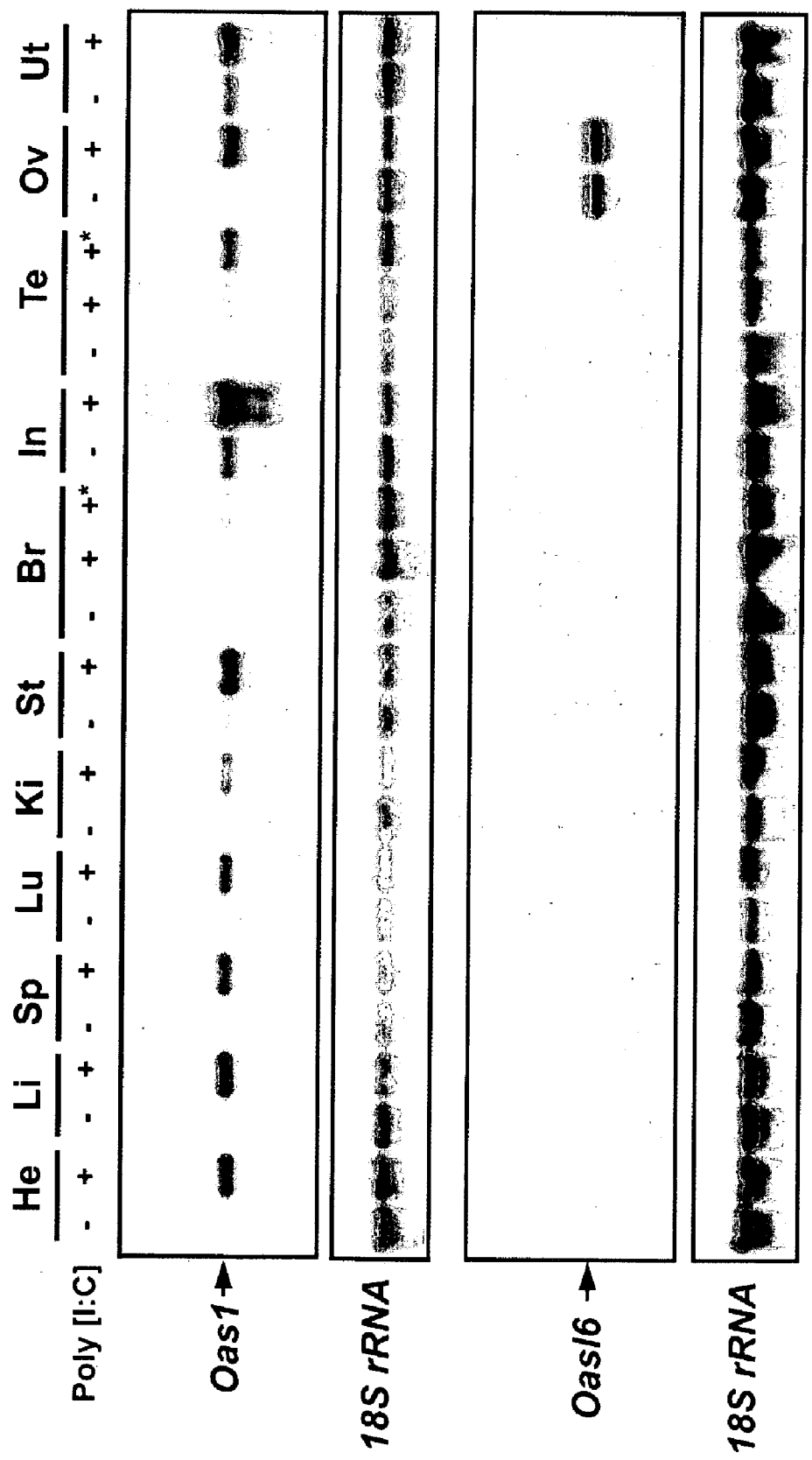
FIG. 12 shows a Northern blot analysis of Oas1 and Oasl6 mRNA expression in multiple tissues of Poly[I:C]-treated and control mice.

The results revealed that Oasl6 was expressed and was induced by Poly[I:C] in the ovary and Oas1 was induced by Poly[I:C] in all tissues examined. Unlike OAS1, which was inducible by poly[I:C], OASL6 does not respond to double-strand RNA stimulation. (FIG. 12).

Example 9

Western Blot Analysis

Recombinant proteins (10 ng) were loaded and detected with pre-immune sera (A) and specific anti-sera (B). Proteins are isolated from multiple tissues including intestine (In), spleen (Sp), lung (lu), uterus (Ut), stomatch (St), liver (Li), Ovary (Ov) were fractionated and transferred on a nylon membrane followed by detection using specific anti-OAS or anti-OASL antibodies.

Figure 13:
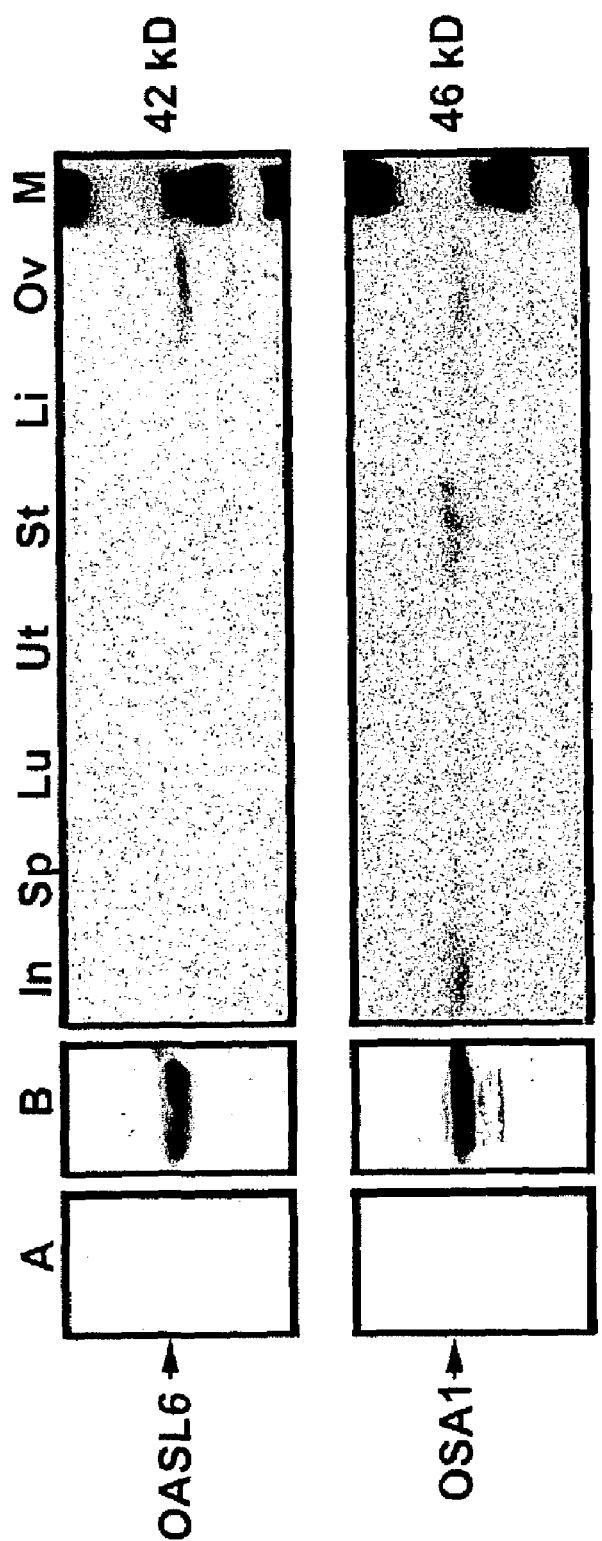
FIG. 13 shows a Western blot analysis of OAS1 and OASL6 proteins. Recombinant proteins were loaded and detected with pre-immune sera (A) and specific anti-sera (B). Proteins isolated from multiple tissues included intestine (In), spleen (Sp), lung (lu), uterus (Ut), stomatch (St), liver (Li), Ovary (Ov).

FIG. 13 shows a Western blot analysis of OAS1 and OASL6 proteins.

Example 10

In Situ Hybridization of Oasl6

In situ hybridization was performed (Yan W., et. al., 2001 Oncogene, 20:1343–1356). A 421 bp PCR fragment from the 3'-UTR of Oasl6 (corresponding to n.t. 1123–1543) was subcloned into pGEM-T vector (Promega, Madison, Wis.) and sense and antisense riboprobes (corresponding to n.t. 1123–1543) were prepared using a Riboprobe Labeling System (Promega).

Figure 14:
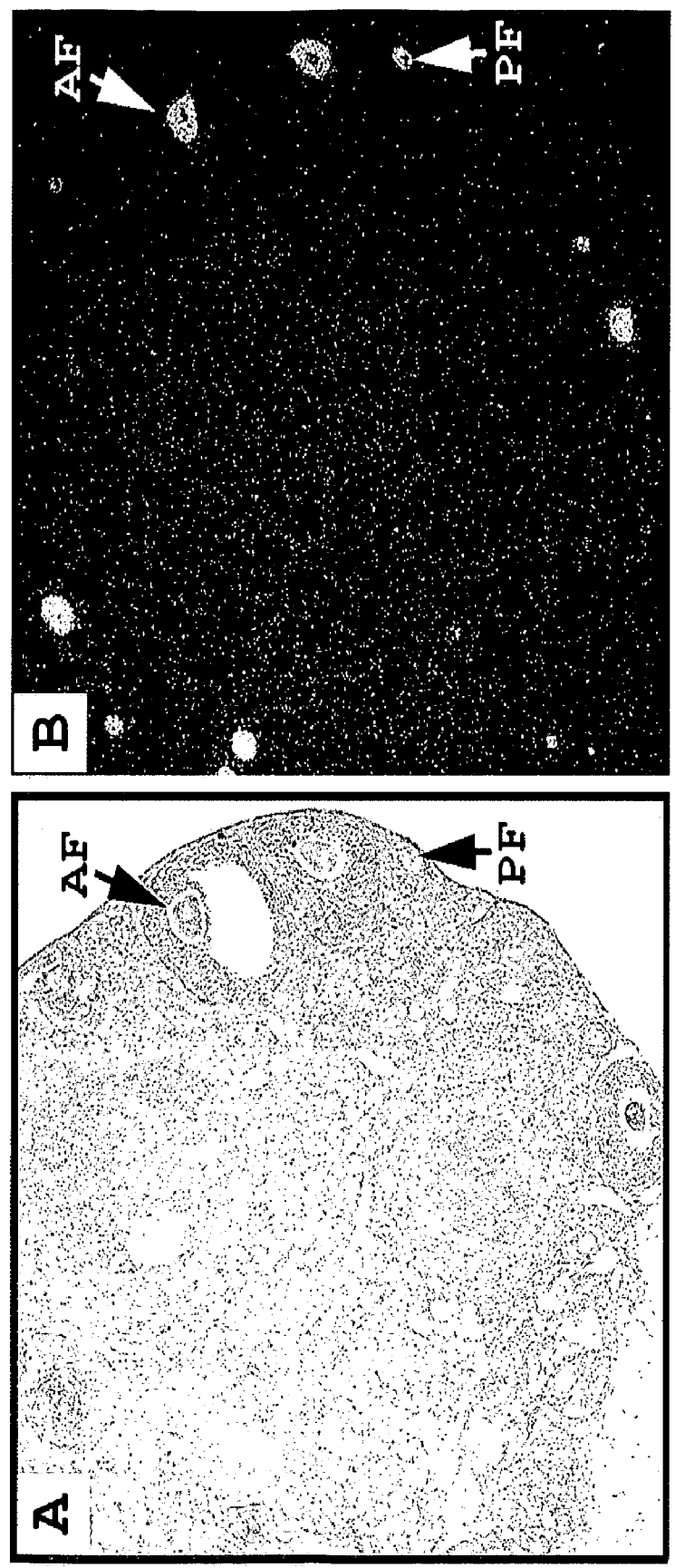
FIG. 14A and FIG. 14B show in situ hybridization analysis of Oasl6 mRNA localization in the ovary.

As shown in FIG. 14, Oasl6 was localized to oocytes in all growing follicles. Thus, Oasl6 is an oocyte-specific gene.

Example 11

Immunohistochemical Localization

The full-length mouse OASL and OAS genes were inserted into pET system vectors (Novagen) to generate recombinant proteins that contained both an N-terminal T7 tag and a C-terminal His tag. Antibodies to the T7 tag were used to identify the recombinant OAS and OAS; the His tag were used to purify the OAS to homogeneity on a Nickel affinity column. Recombinant OAS and OAS proteins were injected into goats to produce antibodies.

Ovaries were fixed in 4% paraformaldehyde in PBS for 2 h, processed, embedded in paraffin, and sectioned at 5 um thickness. Goat anti-OASL polyclonal antiserum was diluted 1:2000 in Common Antibody Dilute (BioGenex). The pre-immune goat serum from the same goat was used as a control. All sections were blocked for 10 min in Universal Blocking Reagent (BioGenex), and incubated with the primary antibody for 1 h at room temperature. OASL and OAS detection were accomplished using anti-goat biotinylated secondary antibody, streptavidin-conjugated alkaline phosphatase label and New Fuschin substrate (BioGenex Laboratories, Inc., San Ramon, Calif.).

One to eight-cell embryos and blastocysts are fixed in 4% paraformaldehyde in PBS for 2 h in 96-well round bottom plate, washed with 0.85% saline, and embedded in a few drops of 1.5% agarose. The agarose-containing embryos are dehydrated, embedded in paraffin, and analyzed as described above.

Figure 15:
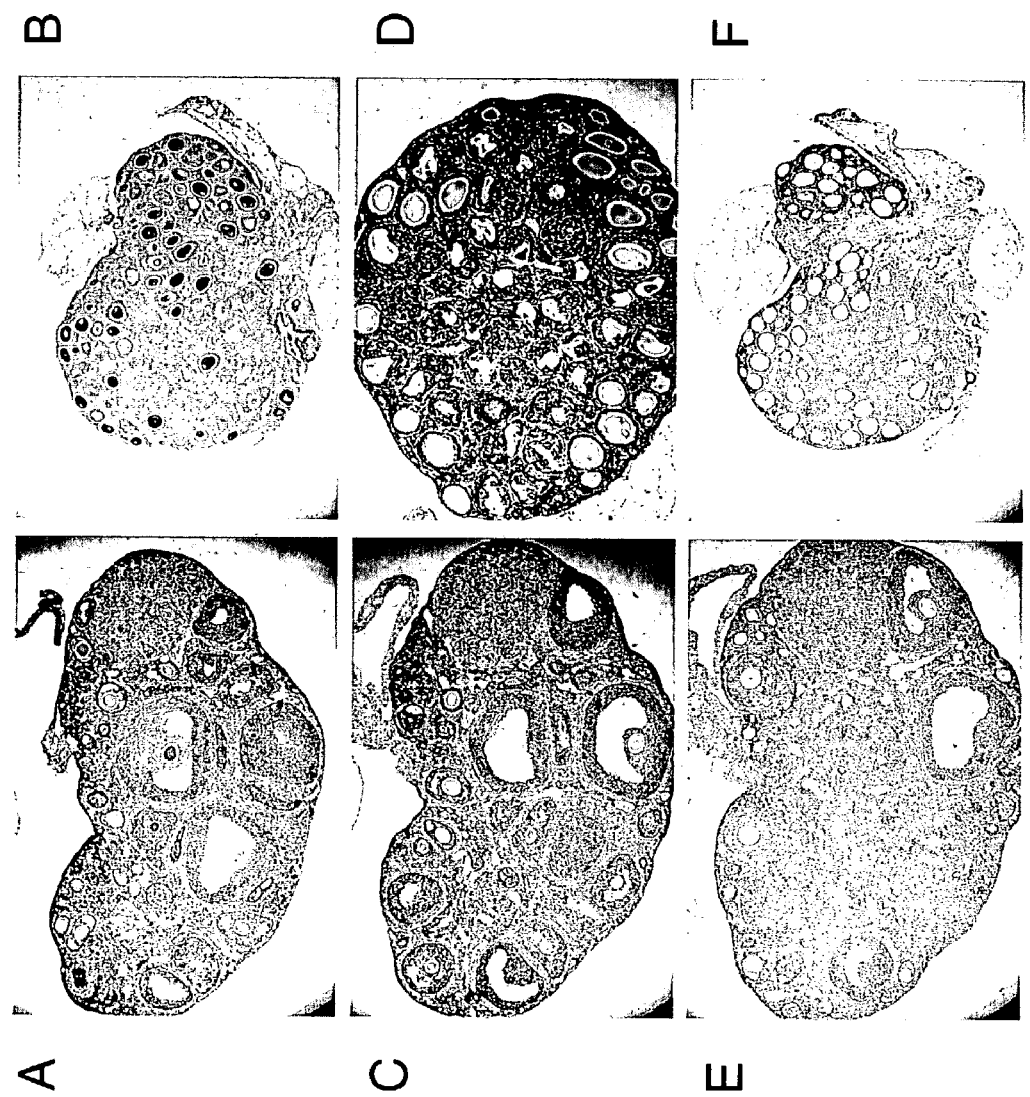
FIG. 15A, FIG. 15B, FIG. 15C, FIG. 15D, FIG. 15E show immunohistochemical localization of OASL and OASL6 proteins in the mouse ovary.

OASL6 immunoreactivity was detected exclusively in the cytoplasm of oocytes of all growing follicles in the adult ovary (FIG. 15A), and oocytes of primary follicles in the Gdf9−/− ovary (FIG. 15B). OAS1 immunoreactivity was present in the cytoplasm of both oocytes, granulosa cells, and luteal cells of the adult ovary (FIG. 15C) and Gdf9−/− ovary (FIG. 15D). Sections stained with pre-immune sera display no immunoreactivity. (FIG. 15E and FIG. 15F).

Example 12

Immunofluorescent Analysis of Oas16

Immuinofluorescent analysis was perforemd on oocytes and early embryos as described by (Yan W. et. al., 2002).

Figure 16:
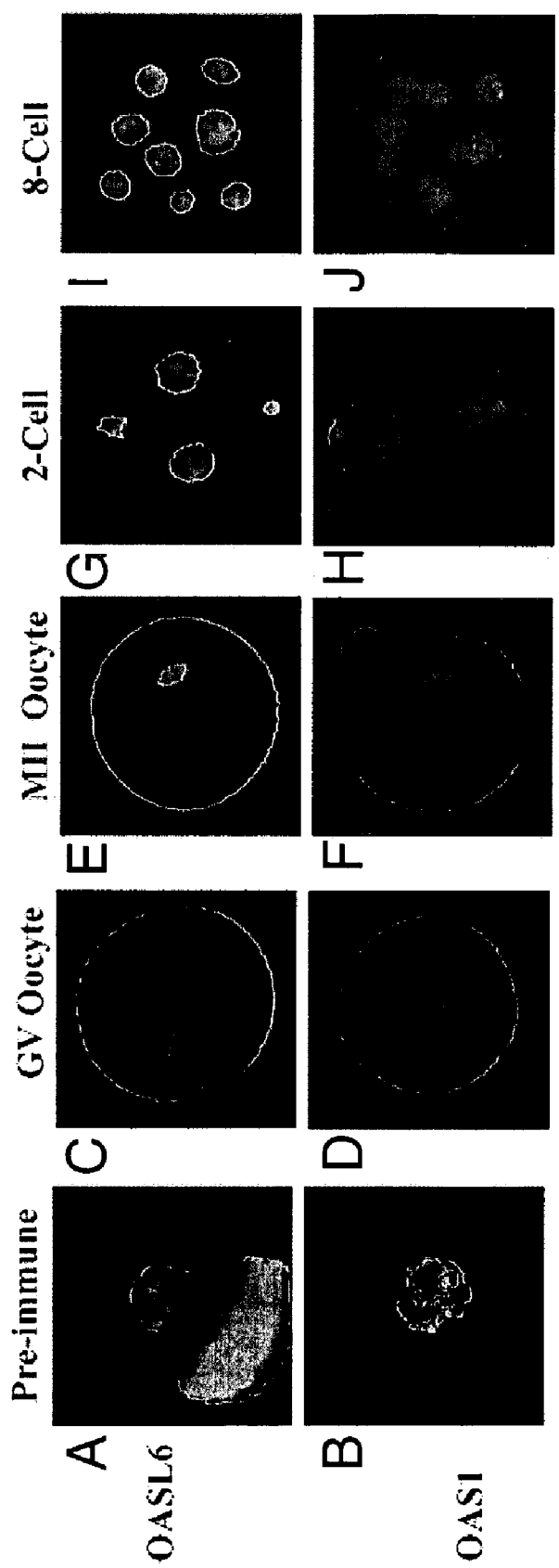
FIG. 16A, FIG. 16B, FIG. 16C, FIG. 16D, FIG. 16E, FIG. 16F, FIG. 16G, FIG. 16H, FIG. 16I and FIG. 16J show immunoflourescent analysis of OASL6 expression in oocytes and early embryos.

As shown in FIG. 16, OASL6 was expressed in oocytes at GV and metaphase II stages, as well as in early embryos at 2–8 cell stages. Thus, the data suggested that OASL6 may function at any of these stages during fertilization and/or early embryogenesis.

Example 13

Regulation of Oas1 and Oasl6 by Poly[I:C]

Aliquots of native (N1 and N2) or fully denatured (D) recombinant OAS1 or OASL6 were incubated with poly[I:C]-agarose, After incubation, the mixture was centrifuged and the agarose beads were washed. Next, the bound protein was applied onto a SDS-PAGE for immunoblotting and analysis by incubation with an anti-His antibody (Invitrogen, Carlsbad, Calif.). The same aliquot from each reaction was subjected to SDS-PAGE before incubating with poly[I:C]-agarose and used as a loading control. The binding assay was performed as previously described (Sarkar and Sen, 1998 Methods: A Companion to Methods in Enzymology 15:233–242).

Figure 17:
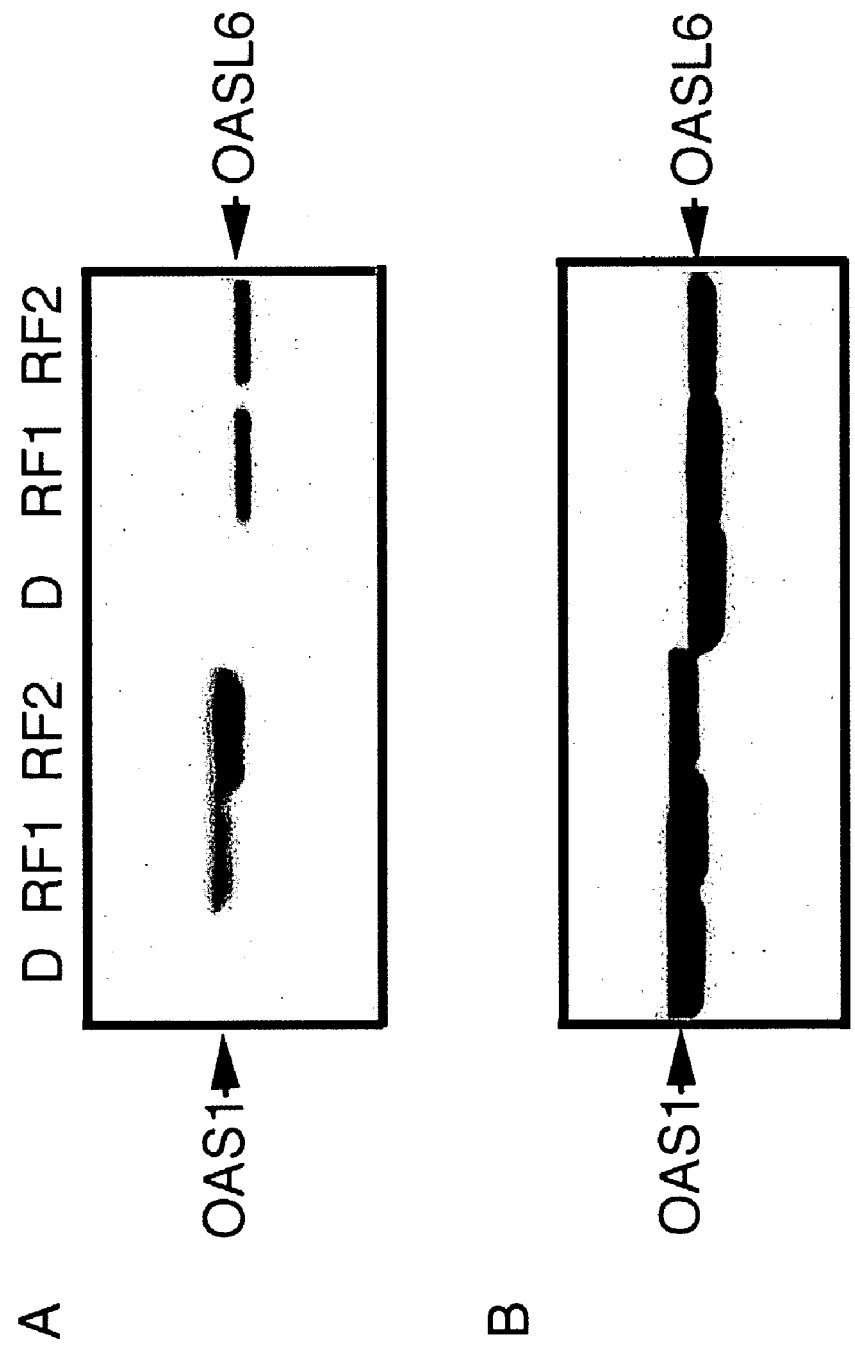
FIG. 17A and FIG. 17B show a Poly[I:C] binding assay.

As shown in FIG. 17A, Fully-denatured (D) OAS 1 and OASL6 failed to bind Poly[I:C]. The results indicated that like OAS1, OASL6 has the ability to bind double-strand RNA.

An aliquot of proteins (equal to the amount used in the binding assay) was blotted to monitor the equal input of proteins in the binding assay (FIG. 17B).

Example 14

2', 5'-Oligoadenylate Synthetase Activity assay

OASL5, which is "ubiquitously" expressed, does not have 2', 5'-oligoadenylate synthetase activity (Shibata et al, 2001). Structure-function studies have shown that the P-Loop, D-Box, and KR-Rich regions of OAS1 proteins are required for catalytic activity (Kon et al., 1996; Yamamoto et al., 2000). The P-Loop binds dsRNA, the D-Box binds Mg++, and KR-rich domain binds ATP for conversion to 2'5'-oligoadenylates. In particular, mutations of K67, D76, D78, and K200 in OAS1A abolish OAS enzymatic activity (Yamamoto et al., 2000). Analysis of mouse OASL5, mouse OASLs, and human OASLs demonstrate that these 4 residues are not conserved. This is the likely reason for the absence of OAS activity in mouse OASL5 and human OASL.

Briefly, 2', 5' oligoadenylate synthetase enzyme activity was assayed by incubating OAS1 or OASL6 (5 ug) with 20 mM Tris-HCl, Ph 7.4, 20 mM magnesium acetate, 2.5 mM DTT, 5 mM ATP, 5 uCi of [$\alpha$-$^{32}$p] ATP (800 Ci/mmol), and 50 μg/ml Poly[I:C] in a 20 μl reaction volume at 37 C for 12 hours. The reaction was stopped by heating at 95° C. The products are analyzed using thin-layer chromatography.

Figure 18:
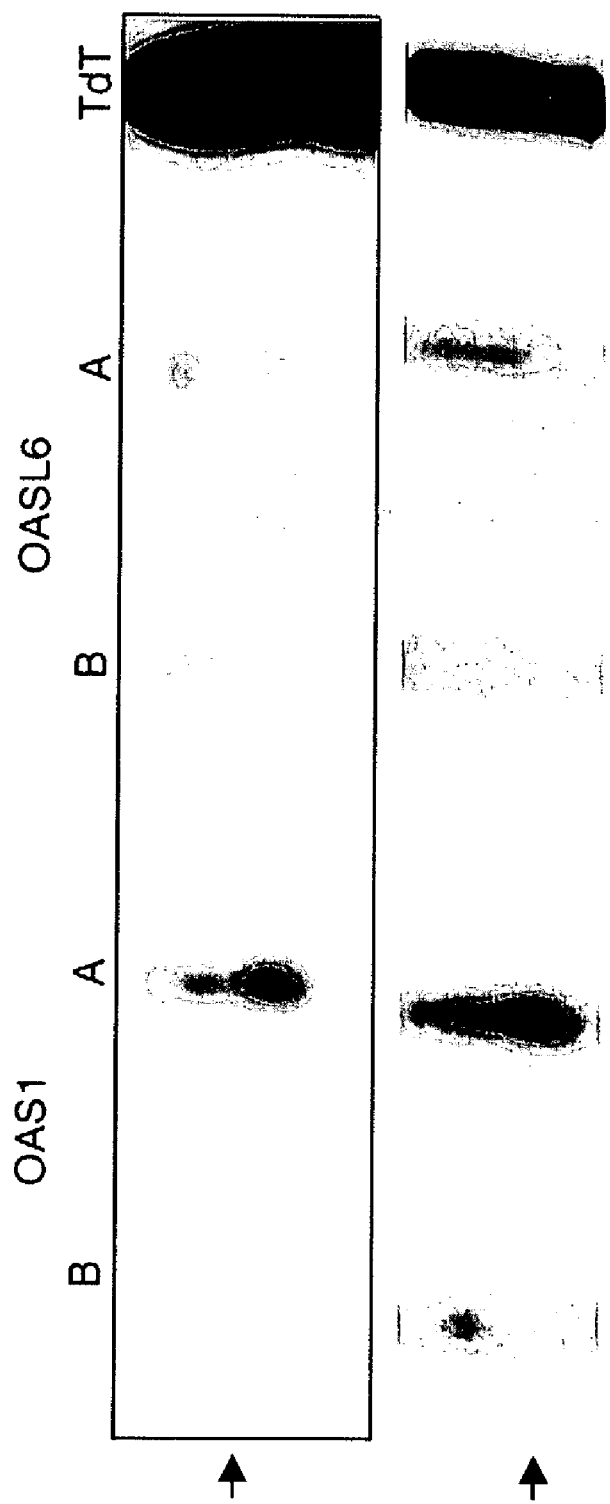
FIG. 18 shows a 2', 5'-oligoadenylate synthetase activity assay. Two independent experiments are shown (upper and lower panels). Before refolding (B), and after refolding (A).

FIG. 18 shows that before refolding (B), the fully-denatured OAS1 did not produce 2', 5'-oligo A, while after refolding (A), 2', 5'-oligo A was observed. No 2', 5'-oligoadenylate was detected in OSAL6 before and after refolding (FIG. 18). Thus, the recombinant OASL6 was folded correctly.

Example 15

2', 5'-Oligoadenylate Synthetase Activity Assay of OASL6

Recombinant mouse OAS and mouse OASL6 were examined for their abilities to convert [$\gamma$-$^{32}$P]ATP into radiolabeled pp[pA]n over several hours (Shibata et al., 2001).

The 2',5'-oligoadenylate synthetase activity assay was performed as described previously in Example 14 (Sarkar and Sen, 1998 Methods: A Companion to Methods in Enzymology 15:233–242). Briefly, poly[I:C]-agarose-bound recombinant proteins were incubated with [$\gamma$-32P]ATP (20 μCi) in reaction buffer containing 20 mM HEPES-KOH, 50 mM KCl, 25 mM Mg(Oac)2, 7 mM 2-mercaptoethanol, 5 mM ATP for indicated hours at 33 C. reaction mixture was centrifuged and the supernatants were fractionated on 20% polyacrylamide gel containing 7M urea. The gel was dried followed by autoradiography.

Figure 19:
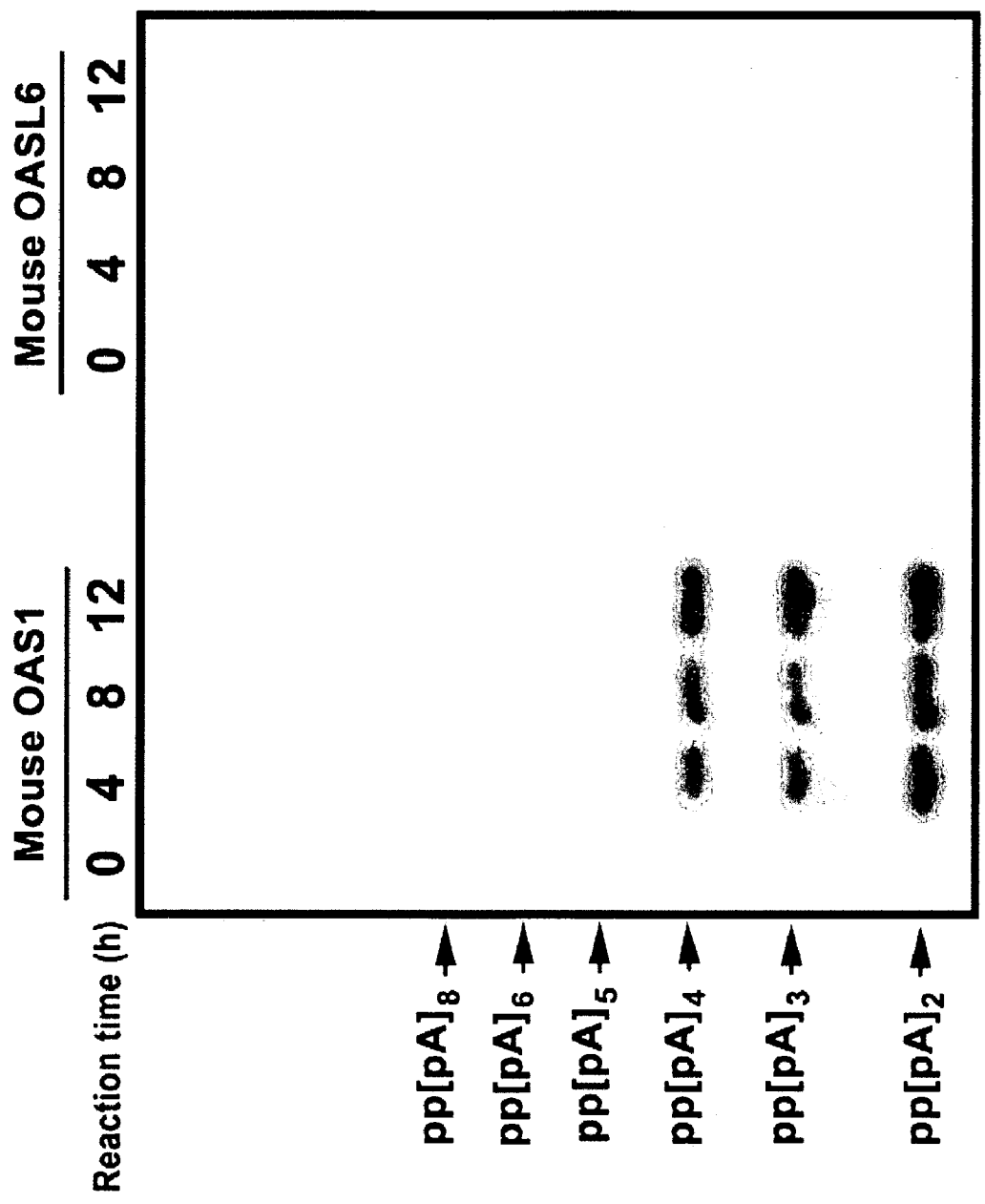
FIG. 19 shows 2', 5'-oligoadenylate synthetase activity assay for OAS1 and OASL6.

As shown in FIG. 19, OASL6 does not have 2', 5'-oligoadenylate synthetase activity.

Example 16

Generate an Oasl6 Null Allele and Produce Oasl6 Knockout Mice

Figure 20:
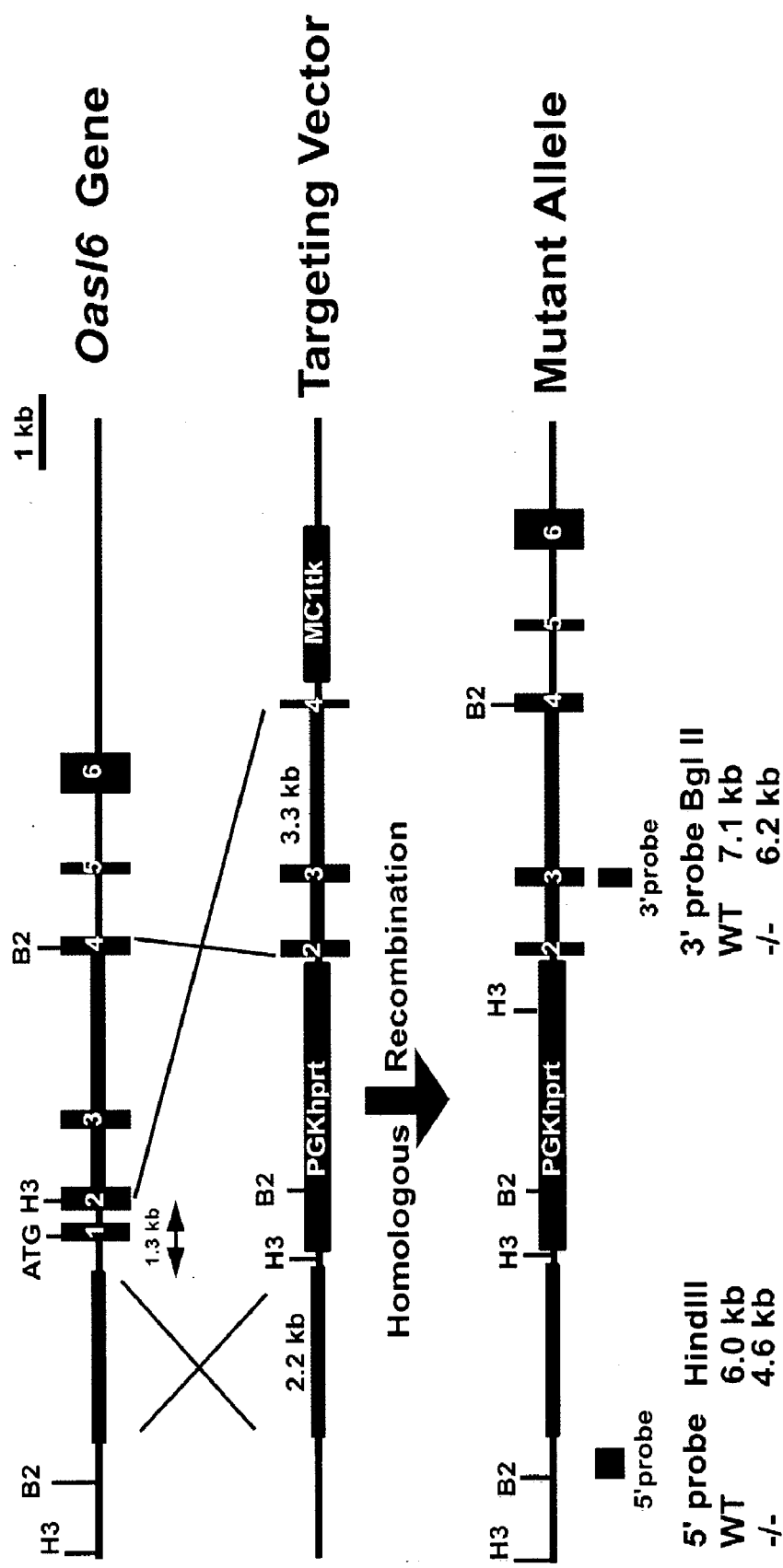
FIG. 20 shows Oasl6 genomic locus, targeting vector to generate an Oasl6 null allele.

Oasl6 disruption and inactivation was achieved by replacing exons 1 and 2 (include the start of transcription, the initiation ATG codon, and 157 codons of OASL6) with an Hprt minigene under control of a Pgk promoter (FIG. 20). HPRT was utilized as a positive selection marker. A negative selection marker, herpes simplex thymidine kinase (TK) mini gene, under the control of the MCI promoter was placed downstream of the 3' arm. Targeting was accomplished in an AB2.1 ES cell line that was Hprt-deficient. After both positive and negative selection the targeted ES cells were verified by Southern blot analysis using both 5' and 3' probes. Replacement of exons 1 and 2 by PgklHprt minigene via homologous recombination in mouse ES cells, resulted in complete absence of Oasl6 transcription.

The correctly targeted ES cells were then injected into C57BL/6 blastocysts and transferred to pseudopregnant recipients as described (Badley, A. 1987). Chimeras were crossed to C57BL/6 mice to produce F1 hybrid mutant mice for the studies.

Figure 21:
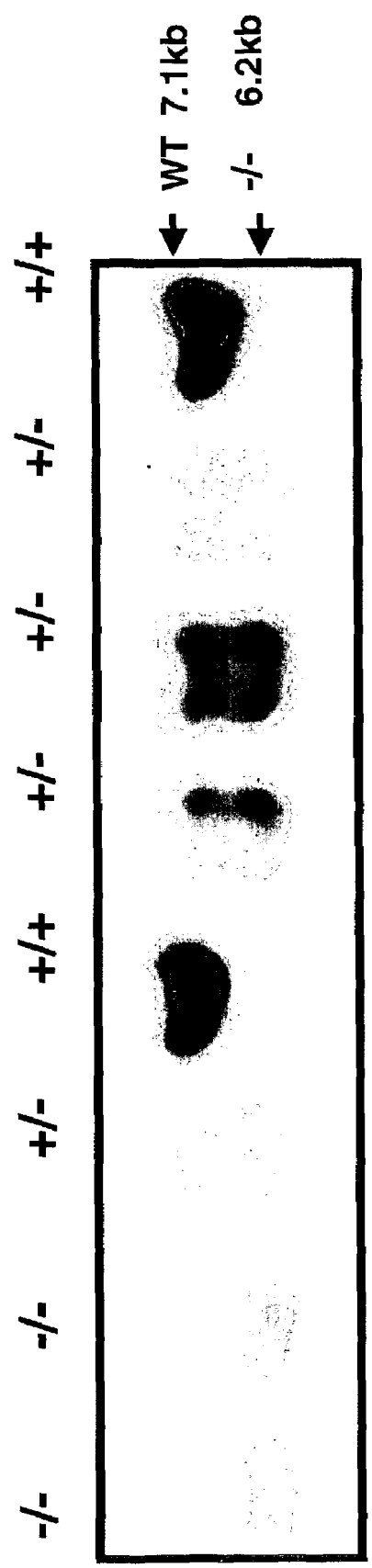
FIG. 21 shows a Southern blot analysis of a litter of mice from a heterozygous mating pair (Oasl6+/−X Oasl6+/−) using 3' probe.

Southern blot analysis of a litter of 8 mice from a heterozygous mating pair (Oasl6$^{+/-}$xOasl6$^{+/-}$) using 3' probe. Tail DNA was isolated and digested with BglII. The Digested DNA was then fractionated on 0.7% agarose gels followed by transfer to GeneScreen Plus membrane (PerkinElmer Life Sciences, Inc., Boston, Mass.). The membrane was UV cross-linked and hybridized using 3' probe labeled with [$\alpha$-$^{32}$P]-dCTP using Rediprime II Random Prime Labeling System (Amersham Biosciences UK limited, Little Chalfont Buckinghamshire, England). Autoradiography was performed using Kodak X-OMAT AR film (Eastman Kodak Company, Rochester, N.Y.). As shown in FIG. 21, Southern blot analysis accurately genotyped mutant and wild type animals.

Example 17

Analyze the Reproductive Performance of Oasl6 Knockout Mice

Heterozygous mice were intercrossed. The offspring from the heterozygous crosses were genotyped at 3 weeks of age and showed Medelian ratio of 1:2:1. Homozygous mutant mice were viable and indistinguishable from their control littermates. Table 1 shows that heterozygous mutant mice reproduced in the Medelian fashion and homozygous mutation of Oasl6 did not affect viability.

TABLE 1

Oasl6 –/– mice are viable
Offspring from +/– x +/– Matings
(n = 149)

| | | |
|---|---|---|
| WT | 32 | (21.5%) |
| +/– | 86 | (57.7%) |
| –/– | 31 | (20.8%) |

To test fertility status of Oasl6-null females, homozygous mutant females were bred with wild-type males (–/–×+/+) and heterozygous breeding pairs (+/–×+/–) were used as controls. Oasl6-null females seem to have reduced litter size (8.3 vs 5.1) (See Table 2). Thus, breeding homozygous females (Oasl6–/–) to wild-type males reveals that the litter size was reduced ~38.5% compared with heterozygote mating controls.

TABLE 2

Fertility of Oasl6 +/– and –/– Mice

| | |
|---|---|
| +/– (n = litters) | 7.25 +/– 0.42 pups/litter |
| –/– (n = 11 litters) | 5.27 +/– 0.73 pups/litter |

The nature/stage of the fertility block is determined by performing a histological analysis of the Oasl6–/– ovaries, examining the ability of the Oasl6−/− oocytes to be released upon pharmacological superovulation, determining the fertilization capacity of Oasl6−/− eggs, and studying the development of early embryos from these Oasl6−/− eggs in culture.

If Oasl6 is involved in unique RNA degradation pathways triggered by maturation, then persistence of maternal transcripts may result in defects in early embryonic cleavage. Under these circumstances, RNAse protection assays of early embryos are used to demonstrate the involvement of RNA degradation. Thus, the failure of the mRNA degradation system during oocyte maturation results in higher levels of transcripts which are normally degraded, like Mos and Plat, in mutant mature eggs than in controls.

REFERENCES

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

Arcone, et al., (1988) *Nucl. Acids Res.,* 16(8): 3195–3207.
Aruffo et al.(1987) *EMBO J.* 6: 3313.
Baichwal and Sugden, In: *Gene Transfer*, pp. 117–148, 1986.
Barany and Merrifield, (1979) *The Peptides*, pp. 1–284.
Bartel, P. L. and S. Fields In: THE YEAST TWO-HYBRID SYSTEM. Oxford University Press, 1997.
Benvenisty and Neshif, (1986) *Proc. Nat'l Acad. Sci. USA,* 83:9551–9555.
Berzal-Herranz et al, (1992) *Genes Dev.* 6(1):129–34.
Bohmann et al., (1989) *Cell.* November 17; 59(4):709–17.
Bradley, A. (1987) in Production and analysis of chimeric mice, ed. Robinson, E. J. (Oxford: IRL, London), pp. 113–151
Brinster et al., (1985) *Proc. Nat'l Acad. Sci. USA,* 82: 4438–4442.
Capecchi et al., *Sci Am* (1994) 270:52–9.
Campbell, In: Monoclonal Antibody Technology, Laboratory Techniques in Biochemistry and Molecular Biology, Vol. 13, Burden and Von Knippenberg, Eds. pp. 75–83, Amsterdam, Elseview, 1984.
Carpten et al., (2002), *Nature Genetics* 30:181–184.
Carter and Flotte, (1995) *Ann. N.Y. Acad. Sci.,* 770:79–90.
Cech et al., (1981) *Cell.* December; 27(3 Pt 2):487–96.
Chatterjee, et al., (1995) *Ann. N.Y. Acad. Sci.,* 770:79–90.
Chen and Okayama (1987) *Mol. Cell Biol.,* 7:2745–2752.
Chowrira et al, (1994) *J Biol Chem.* 269(41):25856–64.
Chowrira et al., (1993) *J Biol Chem.* 268(26):19458–62.
Coffin, (1990) In: *Virology*, ed., New York: Raven Press, pp. 1437–1500.
Coupar et al., (1988) *Gene,* 68:1–10.
Courey et al., (1988) *Cell.* 55(5):887–98.
Davey et al., EPO No. 329 822.
Dubensky et al., (1984) *Proc. Nat'l Acad. Sci. USA,* 81:7529–7533.
Fashena et al., (2000) *Methods Enzymol.* 328:14–26.
Fechheimer et al., (1987) *Proc. Natl Acad. Sci. USA,* 84:8463–8467.
Ferrari et al., (1996) *J. Virol.,* 70:3227–3234.
Fisher et al., (1996) *J. Virol.,* 70:520–532.
Flotte et al., (1993) *PROC. Nat'l Acad. Sci. USA,* 90:10613–10617.
Fodor et al., (1991) *Science,* 251:767–773.
Forster and Symons, (1987) *Cell,* 49:211–220.
Fraley et al., (1979) *Proc. Nat'l Acad. Sci. USA,* 76:3348–3352.
Friedman et al., (1990) *Genes Dev.* August; 4(8):1416–26.
Gefter et al., (1977) *Somatic Cell Genet.* 3:231–236.
Gerster et al., (1990) *EMBO J.* (5):1635–43.
Ghosh and Bachhawat, (1991) In: *Liver Diseases, Targeted Diagnosis and Therapy Using Specific Receptors and Ligands.* Wu et al., pp. 87–104.
Giet et al., (2001) *J Cell Biol.* 152(4):669–82.
Gingeras et al., PCT Application WO 88/10315.
Goding, (1986) In: *Monoclonal Antibodies: Principles and Practice,* 71–74.
Goodman et al., (1994) *Blood,* 84:1492–1500.
Gopal, (1985) *Mol. Cell Biol.,* 5:1188–1190.
Gossen et al., (1995) *Science,* 268:1766–1769.
Gossen and Bujard (1992) *Proc. Nat'l Acad. Sci. USA,* 89:5547–5551.
Graham and van der Eb, (1973) *Virology,* 52:456–467.
Hacia et al., (1996) *Nature Genetics,* 14:441–447.
Hammond et al., (2001) *Nat Rev Genet.* 2(2):110–9.
Harland and Weintraub, (1985) *J. Cell Biol.,* 101:1094–1099.
Haseloff and Gerlach (1988) *Nature.* 334(6183):585–91.
Hay (1984) *J. Mol. Biol.,* 175:493–510.
Hearing and Shenk, (1983) *J. Mol. Biol.* 167:809–822.
Hearing et al., (1987) *J. Virol.,* 67:2555–2558.
Hope et al., (1987) *EMBO J.* September; 6(9):2781–4.
Hu et al., (2000) *Methods.* 20(1):80–94.
James et al., (1996) *Genetics.* 144(4):1425–36.
Johnson et al., (1993) Peptide Turn Mimetics" In: *Biotechnology And Pharmacy.*
Joyce *Nature,* (1989) 338:217–244.
Kageyama et al., (1987) *J. Biol. Chem.,* 262(5):2345–2351.
Kaneda et al., (1989) *Science,* 243:375–378.
Kaplitt et al., (1994) *Nat'l Genet.,* 8:148–153.
Kato et al, (1991) *J. Biol. Chem.,* 266:3361–3364.
Kim and Cook, (1987) *Proc. Nat'l Acad. Sci. USA,* 84:8788–8792.
Klein et al., (1987) *Nature,* 327:70–73.
Koeberl et al., (1997) *Proc. Nat'l Acad. Sci. USA,* 94:1426–1431.
Kohler and Milstein, (1976) *Eur. J. Immunol.,* 6:511–519.
Kon, N. et al., (1996) *J. Biol Chem* 271, 19983–90.
Legrain, P. et al., (2001) *Trends Genet.* 17, 346–52.
Levrero et al., (1991) *Gene,* 101:195–202.
Lieber et al., (1995) *Mol Cell Biol.* 15(1):540–51.
Lira S A et al., *Proc. Nat'l Acad. Sci. USA* (1990) September; 87(18):7215–9.
Ma et al., (1987) 50:137–42.
Mann et al., (1983) *Cell,* 33:153–159.
Martin et al., (1990) *Genes Dev.* (11):1886–98.
McCown et al., (1996) *Brain Res.,* 713:99–107.
Mermod et al., (1989) *Cell.* 58(4):741–53.
Merrifield, (1986) *Science,* 232: 341–347.
Michel and Westhof (1990) *J. Mol. Biol,* 216:585–610.
Miller et al., PCT Application WO 89/06700.
Muller-Immergluck et al., (1990) *EMBO J.* 9(5):1625–34.
Nakamura et al., (1987) In: *Handbook of Experimental Immunology* (4th Ed.).
Nicolau and Sene (1982) *Biochim. Biophys. Acta,* 721: 185–190.
Nicolau et al., (1987) *Methods Enzymol.,* 149:157–176.
Oliviero (1987) et al., *EMBO J,* 6(7):1905–1912.
Paskind et al., (1975) *Virology,* 67:242–248.
Pease et al., (1994) *Proc. Nat'l Acad. Sci. USA,* 91:5022–5026.
Perriman et al., (1992) *Gene.* 113(2):157–63.

Perrotta and Been (1992) Biochemistry. 31(1):16–21.
Peschon J J et al., Proc. Nat'l Acad. Sci. USA (1987) August; 84(15):5316–9.
Pierson et al., (2000) Molecular Endocrinology 14:1075–1085.
Ping et al., (1996) Microcirculation, 3:225–228.
Poli and Cortese, (1989) Proc. Nat'l Acad. Sci. USA, 86:8202–8206.
Potter et al., (1984) Proc. Nat'l Acad. Sci. USA, 81:7161–7165.
Prowse and Baumann (1988) Mol Cell Biol, 8(1):42–51.
Radler et al., (1997) Science, 275:810–814.
Rebouillat, D. et al., (1999) J. Interferon Cytokine Res 19, 295–308.
Reinhold-Hurek and Shub, (1992) Nature, 357:173–176.
Renan (1990) Radiother. Oncol., 19:197–218.
Ridgeway, (1988) In: Vectors: A survey of molecular cloning vectors and their uses, pp. 467–492.
Rippe et al., (1990) Mol. Cell Biol., 10:689–695.
Ron, et al, (1991) Mol. Cell. Biol., 2887–2895.
Roux et al., (1989) Proc. Nat'l Acad. Sci. USA, 86:9079–9083.
Sadowski et al., (1988) Nature. 335(6190):563–4.
Sambrook et al., (1989) MOLECULAR CLONING: A LABORATORY MANUAL, 2nd Ed., Cold Spring Harbor Laboratory Press, Cold Spring Harbor, N.Y.
Samulski et al., (1987) J. Virol., 61(10):3096–3101.
Sarver et al., (1990) Science, 247:1222–1225.
Scanlon et al., (1991) Proc. Nat'l Acad. Sci. USA, 88:10591–10595.
Seed et al., (1987) Proc. Nat'l Acad. Sci. USA, 84: 3365.
Shibata, S. et al., (2001) Gene 271, 261–71.
Shoemaker et al., (1996) Nature Genetics 14:450–456.
Sioud et al., (1992) J Mol Biol. 223(4):831–5.
Soyal, et al., (2000) Development 127:4645–4654.
Stewart and Young, (1984) Solid Phase Peptide Synthesis, 2d. ed., Pierce Chemical Co.
Tam et al., (1983) J. Am. Chem. Soc., 105:6442.
Temin, (1986) In: Gene Transfer, Kucherlapati (ed.), New York: Plenum Press, pp. 149–188.
Thompson et al., (1995) Nucleic Acids Res. 23(12):2259–68.
Tibbetts (1977) Cell, 12:243–249.
Tur-Kaspa et al., (1986) Mol. Cell Biol., 6:716–718.
Watt et al., (1986) Proc. Nat'l Acad. Sci., 83(2): 3166–3170.
Wilson et al., (1990) Mol. Cell. Biol., 6181–6191.
Wong et al., (1980) Gene, 10:87–94.
Wong et al., (1985) Science, 228: 810–815.
Wu and Wu, (1987) J. Biol. Chem., 262:4429–4432.
Wu and Wu, (1988) Biochem., 27:887–892.
Wu, L. C., et al., (1996) Nat Genet 14, 430–40.
Xiao et al., (1996) J. Virol., 70:8098–8108.
Yamamoto, Y. et al., (2000) J. Interferon Cytokine Res 20, 337–44.
Yan W., et. al., 2002 Mol. Endo., 16:1168–1184
Yang et al., (1990) Proc. Nat'l Acad. Sci. USA, 87:9568–9572.
Yuan and Altman (1994) Science. 263(5151):1269–73.
Yuan et al., (1992) Proc. Natl Acad Sci. USA 89(17): 8006–10.
Zechner et al., (1988) Mol. Cell. Biol., 2394–2401.
Zhang L P et al., Biol Reprod. (1999) Jun; 60(6):1329–37.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An isolated polypeptide comprising the amino acid sequence of SEQ. ID. NO.2.

2. An isolated polypeptide encoded by the polynucleotide sequence of one of the following selected from the group consisting of:
   a) an isolated polynucleotide sequence comprising the nucleic acid sequence of SEQ. ID. NO.1; or
   b) an isolated polynucleotide sequence encoding a protein, wherein said protein is selected from the group consisting of:
   (1) a polynucleotide sequence encoding the sequence of SEQ. ID. NO.2;
   (2) a polynucleotide sequence which is 97% identical to the sequence of SEQ ID NO: 1 and encodes a polypeptide having oligoadenylate synthetase like (OASL) activity;
   (3) an isolated nucleic acid molecule that hybridizes with the polynucleotide sequence of (1) under stringent conditions of 0.02 M to about 0.15 M NaCl at a temperatures of about 65° C.; and encodes a polypeptide having OASL activity.
   (4) an isolated polynucleotide sequence that is a full complement to (1), (2) or (3).

3. An isolated polypeptide of claims 1 or 2, wherein the polypeptide has oligoadenylate synthetase like (OASL) activity.

4. A composition for modulating oligoadenylate synthetase like (OASL) activity comprising an effective amount of a polypeptide of claim 1 or 2.

* * * * *

SEQUENCE LISTING

```
<160> NUMBER OF SEQ ID NOS: 32

<210> SEQ ID NO 1
<211> LENGTH: 1730
<212> TYPE: DNA
<213> ORGANISM: Mouse

<400> SEQUENCE: 1
ggcacgagca aacactcctg gcctcaggat ggcgagggaa ctcttcagaa ccccaatctg      60
gaggctggat aagttcatag aggatcaact ccttcctgac accaccttcc ttactgagct     120
cagagcagac atcgactcca taagtgcttt cctgatggag agatgcttcc aaggtgccgc     180
ccatcctgtg agggtctcca gggttgtgat gggtggctgc tacaatgaat acactgtgct     240
caagggcagg tctgaggcca acatggtggt gttccttatc aatctcacaa gctttgagga     300
tcagttcaac ggacaggtag tgttcattga ggaaatttgg agacacctac tccagttgca     360
gcaagagaaa ctatgtaaac tcaagtttga ggtccagagc ccaaaggagc caactccag     420 gtttctgagc ttcaagctga gctgccccga gcgccagcat gagttggaat ttgatgtgca     480
```

-continued

```
gccagcctat gatgccctgt atgaagtaag acacttcaag cccttTgact ccagtaacta    540
caacaaagtc tacgcccaac tcacccatga gtgcaccaca ctggagaagg agggcgagtt    600
ctccatctgc ttcaccgacc tccatcagag cttcctgagg tatcgtgcgc ccaagctctg    660
gaacctcatc cgtttggtca agcactggta tcaactgtgt aaggagaagc tgaggggggcc   720 gctgcctcca cagtacgccc tggagctgct cacagtctac gtctgggaat acgggatcca    780
cgaaaaccct ggactccata cagcccagtg cttccgcact gtcttagaac ttgtcaccaa    840
gtacaaacgg cttcgaatct actggacatg gtgttatgac tttcaacacg agatctctga    900
ctacctgcag ggacagatca aaaaagccag gcctctgatc ctggatccag cagacccaac    960
aaggaatgtg gctggttcag acttacaggc atgggacctg ctggcaaagg aggctcagat   1020
ctggatagat tcgactttct ttacgaacca tgatatgtcc attgtggaag cctgggaagt   1080
gatgccagag agacaagaat gtgtcttcct gtgagcaccc ccagcatctg cctaggagac   1140
tccagagtca ggggcatgtc ctcctcttct gtaagacctt gacctagaga ggacagacag   1200
gatggcactc aaggctccag cgaggggcat ccaacctgtg atcagactcc aggcttctga   1260
tccctgcctg cccatggaca gccttcctca caggctgctt cgtctgcctt agcttccaac   1320
agtgttctct gggagtcaga ctgtgatgga cagagaagaa cgcaagctcg acttccatct   1380
gttcacctgt tgggaggtta tgtccaatag tggctgatca tcatcaacaa accacagcaa   1440
gccatgaggg ggggtgcact ctgagggagg agtcctcaga ccacacagaa acttttcagc   1500
agtgcatgtg gccctggagc cctgggaatc tggccagtgt tcatcaaggt gcactgtttc   1560
ttgcaacatg caggctgggt ttatggtagt gcaggaaaat aaaattgcat gcattttaaa   1620
atttatgatt ttaaaactta ggggtgtgtg gtgtatgaga tttgaagcac taaattaaag   1680
caaaacgcat tgaattaaac taaatgaatt aaaaaaaaaa aaaaaaaaa              1730
```

<210> SEQ ID NO 2
<211> LENGTH: 361
<212> TYPE: PRT
<213> ORGANISM: Mouse

<400> SEQUENCE: 2

```
Met Ala Arg Glu Leu Phe Arg Thr Pro Ile Trp Arg Leu Asp Lys Phe
 1               5                  10                  15

Ile Glu Asp Gln Leu Leu Pro Asp Thr Thr Phe Leu Thr Glu Leu Arg
                20                  25                  30

Ala Asp Ile Asp Ser Ile Ser Ala Phe Leu Met Glu Arg Cys Phe Gln
            35                  40                  45

Gly Ala Ala His Pro Val Arg Val Ser Arg Val Val Met Gly Gly Cys
        50                  55                  60

Tyr Asn Glu Tyr Thr Val Leu Lys Gly Arg Ser Glu Ala Asn Met Val
65                  70                  75                  80

Val Phe Leu Ile Asn Leu Thr Ser Phe Glu Asp Gln Phe Asn Gly Gln
                85                  90                  95

Val Val Phe Ile Glu Glu Ile Trp Arg His Leu Leu Gln Leu Gln Gln
            100                 105                 110

Glu Lys Leu Cys Lys Leu Lys Phe Glu Val Gln Ser Pro Lys Glu Pro
        115                 120                 125

Asn Ser Arg Phe Leu Ser Phe Lys Leu Ser Cys Pro Glu Arg Gln His
    130                 135                 140

Glu Leu Glu Phe Asp Val Gln Pro Ala Tyr Asp Ala Leu Tyr Glu Val
145                 150                 155                 160
```

-continued

```
Arg His Phe Lys Pro Phe Asp Ser Ser Asn Tyr Asn Lys Val Tyr Ala
            165                 170                 175

Gln Leu Thr His Glu Cys Thr Thr Leu Glu Lys Glu Gly Glu Phe Ser
        180                 185                 190

Ile Cys Phe Thr Asp Leu His Gln Ser Phe Leu Arg Tyr Arg Ala Pro
    195                 200                 205

Lys Leu Trp Asn Leu Ile Arg Leu Val Lys His Trp Tyr Gln Leu Cys
210                 215                 220

Lys Glu Lys Leu Arg Gly Pro Leu Pro Pro Gln Tyr Ala Leu Glu Leu
225                 230                 235                 240

Leu Thr Val Tyr Val Trp Glu Tyr Gly Ile His Glu Asn Pro Gly Leu
                245                 250                 255

His Thr Ala Gln Cys Phe Arg Thr Val Leu Glu Leu Val Thr Lys Tyr
            260                 265                 270

Lys Arg Leu Arg Ile Tyr Trp Thr Trp Cys Tyr Asp Phe Gln His Glu
        275                 280                 285

Ile Ser Asp Tyr Leu Gln Gly Gln Ile Lys Lys Ala Arg Pro Leu Ile
    290                 295                 300

Leu Asp Pro Ala Asp Pro Thr Arg Asn Val Ala Gly Ser Asp Leu Gln
305                 310                 315                 320

Ala Trp Asp Leu Leu Ala Lys Glu Ala Gln Ile Trp Ile Asp Ser Thr
                325                 330                 335

Phe Phe Thr Asn His Asp Met Ser Ile Val Glu Ala Trp Glu Val Met
            340                 345                 350

Pro Glu Arg Gln Glu Cys Val Phe Leu
        355                 360
```

<210> SEQ ID NO 3
<211> LENGTH: 1776
<212> TYPE: DNA
<213> ORGANISM: Mouse

<400> SEQUENCE: 3

| | | | | | |
|---|---|---|---|---|---|
| tgacgccagc | tctaatacga | ctcactatag | ggaaagctgg | tacgcctgca | ggtaccggtc | 60 |
| cggaattccc | gggtcgacta | tccctggcct | caggatggcg | agggaactct | tcagaacccc | 120 |
| aatctggagg | ctggataact | tcatagagga | tcaactcctt | cctgacacca | ccttccttac | 180 |
| tgagctcaga | gcagacatcg | actccataag | tgctttcctg | aaggagagat | gcttccaagg | 240 |
| tgccacccac | cctatgaggg | tcgccagggt | tgtgatggga | ggctcctatg | atgaacacaa | 300 |
| tgcactcaag | ggaaggtcag | aggccaacat | ggtggtgttc | tttaatgatc | tcaccagctt | 360 |
| tgaggaccag | ttaaagtggc | agcaagtgtt | cattgaagaa | attcggaaac | acctgctcca | 420 |
| gttgcagcaa | gagaagccat | gtaaactcaa | gtttgaggtg | cagagctcag | aggagcccaa | 480 |
| caccaggtct | ctgaccttca | agctgtgctc | cccagagcgc | cagcaggagg | tggaatttga | 540 |
| tgtgcagcca | gcctatgatg | ctctgtatga | aggggatac | tgcaagtcct | ttgaatccat | 600 |
| taactacaac | aaagtctacg | cccaactcat | ccatgagtgc | accaccctgg | agaaggaggg | 660 |
| cgagttctcc | atctgcttca | ccgaccttca | tcagagcttc | ctgaggtatc | gtgcgcccaa | 720 |
| gctctggaac | ctcatccgtc | tggtcaagca | ctggtatcaa | ctgtgtaagg | agaagctgag | 780 |
| gggaccgctg | cctccacagt | atgccctgga | gctgctcaca | gtctacgtct | gggaatttgg | 840 |
| ggtccaagac | agctttggac | tccatgcagc | ccagtgcttc | cgaacggtct | tagaactggt | 900 |
| caccaagtac | aaatgccttc | taatctactg | gacatggttt | tatgactttc | gacctgagat | 960 |

-continued

```
ctctgactac ctgcacggac agatcaaaaa agccaggcct ctgatcctgg atccggcaga    1020
cccaacaagg aacgtggctg gttcagactt acaggcatgg gacctgctgg caaaggaggc    1080
tcagacctgg atacattcaa atttttttag gaactgtgat atgtcccttg tgaatggctg    1140
ggaagtgtcg ccagagaaac aataatgtgt cttccagtga gcagtgtagc acttgcctag    1200
aaggctccag agtcaggatc atgtgctcct ccgctgtaag actttgacct agagaggaca    1260
ggatggtgct catgtctcca gcgaggggta tccaacctgt gattagactc caggcttctg    1320
atccctgcct gcccatggat agccttcctc acaggctgct tcatctgcct tagcttccaa    1380
cagtgttctc tgggagtcag gctgtgatgg acagagaaga acgcaagctc gacttccatc    1440
tgtccacctg ttgggaggtt ctgtccaata gtggctgatc gtcatcatca aatcacagca    1500
agccatgggg gagggtgcac tctgagggag tcctcagacc acacagaaac ttttcagcag    1560
tgcatgtggc cctggcaccc tgggaatctg ccagtgttc atcaaggtgc actgttttac    1620
aacatgcagg ccgggtttat ggcagttcgg gaaaataaaa ctgcggatac tttaaattta    1680
tgactttaaa atttaggtgt atgtgtgtgt gtgtgtatat atatatataa tttgaagcac    1740
tgaattaaat caaaatgcat taaaaaaaaa aaaaaa                              1776
```

<210> SEQ ID NO 4
<211> LENGTH: 356
<212> TYPE: PRT
<213> ORGANISM: Mouse

<400> SEQUENCE: 4

```
Met Ala Arg Glu Leu Phe Arg Thr Pro Ile Trp Arg Leu Asp Asn Phe
1               5                   10                  15

Ile Glu Asp Gln Leu Leu Pro Asp Thr Thr Phe Leu Thr Glu Leu Arg
            20                  25                  30

Ala Asp Ile Asp Ser Ile Ser Ala Phe Leu Lys Glu Arg Cys Phe Gln
        35                  40                  45

Gly Ala Thr His Pro Met Arg Val Ala Arg Val Val Met Gly Gly Ser
    50                  55                  60

Tyr Asp Glu His Asn Ala Leu Lys Gly Arg Ser Glu Ala Asn Met Val
65                  70                  75                  80

Val Phe Phe Asn Asp Leu Thr Ser Phe Glu Asp Gln Leu Lys Trp Gln
                85                  90                  95

Gln Val Phe Ile Glu Glu Ile Arg Lys His Leu Leu Gln Leu Gln Gln
            100                 105                 110

Glu Lys Pro Cys Lys Leu Lys Phe Glu Val Gln Ser Ser Glu Glu Pro
        115                 120                 125

Asn Thr Arg Ser Leu Thr Phe Lys Leu Cys Ser Pro Glu Arg Gln Gln
    130                 135                 140

Glu Val Glu Phe Asp Val Gln Pro Ala Tyr Asp Ala Leu Tyr Glu Gly
145                 150                 155                 160

Gly Tyr Cys Lys Ser Phe Glu Ser Ile Asn Tyr Asn Lys Val Tyr Ala
                165                 170                 175

Gln Leu Ile His Glu Cys Thr Thr Leu Glu Lys Glu Gly Glu Phe Ser
            180                 185                 190

Ile Cys Phe Thr Asp Leu His Gln Ser Phe Leu Arg Tyr Arg Ala Pro
        195                 200                 205

Lys Leu Trp Asn Leu Ile Arg Leu Val Lys His Trp Tyr Gln Leu Cys
    210                 215                 220
```

-continued

```
Lys Glu Lys Leu Arg Gly Pro Leu Pro Pro Gln Tyr Ala Leu Glu Leu
225                 230                 235                 240

Leu Thr Val Tyr Val Trp Glu Phe Gly Val Gln Asp Ser Phe Gly Leu
            245                 250                 255

His Ala Ala Gln Cys Phe Arg Thr Val Leu Glu Leu Val Thr Lys Tyr
        260                 265                 270

Lys Cys Leu Leu Ile Tyr Trp Thr Trp Phe Tyr Asp Phe Arg Pro Glu
    275                 280                 285

Ile Ser Asp Tyr Leu His Gly Gln Ile Lys Lys Ala Arg Pro Leu Ile
290                 295                 300

Leu Asp Pro Ala Asp Pro Thr Arg Asn Val Ala Gly Ser Asp Leu Gln
305                 310                 315                 320

Ala Trp Asp Leu Leu Ala Lys Glu Ala Gln Thr Trp Ile His Ser Asn
                325                 330                 335

Phe Phe Arg Asn Cys Asp Met Ser Leu Val Asn Gly Trp Glu Val Ser
            340                 345                 350

Pro Glu Lys Gln
        355
```

<210> SEQ ID NO 5
<211> LENGTH: 2530
<212> TYPE: DNA
<213> ORGANISM: Mouse

<400> SEQUENCE: 5

| | | |
|---|---|---|
| atggtgaagg atcttagcag caccccagcc tgtgagctgg acaagttcat acgtgatcat | 60 |
| ctccttcccg attccagctt ccatgctgag gccagagcag acgtggactt cataggtgct | 120 |
| ttcctgaagg agagatgctt ccaaggtgcc acccaccctg tgagggtctc cagggttgtg | 180 |
| atgggcggct cctacgacga acacactgca ctcaagagca agtcagaggc taaaatggtg | 240 |
| gtgttcctta acaatctcac cagcttcgag gagcagttaa agcgacgggg agagttcatt | 300 |
| gaggaaattc ggaaacacct gtgtcagctg caggatgaga accatttaa agtgaagttt | 360 |
| gaggtgcaga gctcagagga gcccaactcc aggtctctga gcttcaagct gagctcccct | 420 |
| gagctccagc aggaggtgga atttgatgtg cagccagcct atgatgtcct gtatgaactg | 480 |
| agaaacaaca gtatgctga actctacttg tacaacaaaa tctacgccca actcatccat | 540 |
| gagtgcacca cactaaagaa ggagggcgag ttctccatct gcttcaccga cctccatcag | 600 |
| agcttcctgg aggatcgtgc acccaagctg aagaacctca tccgtttggt caagcactgg | 660 |
| tatcaactgt gtaaggagaa gctggggaag ccgctgcccc cacagtatgc cctggagctg | 720 |
| ctcacagtgt acgcctggga aagtgggagt agagactgcg aattcaacac agcccagggc | 780 |
| ttccgaactg tcttggaact ggtcaccaag tacaagtggc ttcgaatcta ctggacagtg | 840 |
| tattatgact ttagaaagac gaaggtctct gaatacctgc acaaaatgct ccaaaaagtc | 900 |
| aggcctgtga tcctggaccc tgctgaccca acaaggaacg tggctggtac caacctacta | 960 |
| ggctggggc tgttggcaaa agaagctgcc atctggctgc agtcctcctg ctttaggaac | 1020 |
| tgtgatacgt gcctcgtggg cccctggggt gtgccgggtg ttcctacaa tcgatacact | 1080 |
| gtgctcaagg gcaggtcaga ggtcgaccta ttggtattct ttaataatct cacctgcttt | 1140 |
| gacgatcagt tcaagctaca gaaagaggtc attgaggaaa ttcagaaaca cctgtgccag | 1200 |
| ttccagcaag aaaaacgact gagagagaag tttaaggtcc agagctcaga ccagcccaac | 1260 |
| tttaggtccg tgagcttcaa actgagctac cccaagtttc agcaggaggt ggaatttcat | 1320 |

```
atgcagacag cctatgatgc cctgtatgaa gtgagaagaa aagagaatca taactgtgaa    1380
atctacaaca aagtatacgc ccgactcatc cgtgagtgca ccatgctggg caaggagggc    1440
gagttcaaca tctgcttcat ggagcttcag caagactttc tgtggaaacg tccatgcgag    1500
ctgaagaacc tcatttgtct ggtcaagcac tggtatcaac tgtgtaagga aagctgagg     1560
gagccgctgc ctccacagta cgccctggag ctgctcactg tctatgcctg ggaacatgag    1620
cttccagaca acatgaaac acagacagct cggggtttcc ggaccgtctt agaactgatc     1680
actaagtacc tatgtcttcg aatctactgg acattgtatt atgacgttct acatgaacag    1740
gtcaatgcct acctgtactc acaggtcaaa gagtcagtc ctctgatctt ggacccagca     1800
gacccaacat ggaacgtggc tggtttaaac ttacagggct ggtgcatact ggcagaagag    1860
gcaaaagcct ggctggatta cccatgcttt aagaacaggg atggttcccg agtgagctcc    1920
tgggatgtgc cgccagacaa aaaggatt gtcttcctgt gagcacccaa agcatctgcc      1980
aaggagactc ccagagtcag ggtcatgtgc tcctctgctg taagactttg acctagagag    2040
gaccggatgg tgctcatgga gccagcgagg ggtatccaac ctgtgatcag actccaggct    2100
tctgatccct gcctgcccgc ccatggacag ccttcctcac agcctgcttc atctgcctaa    2160
gcctctaaca gtgttttctg ggagtcaggc tgtgatggac agagatttga cttccatctg    2220
tccacctgtt gggaggttct gtccaatagt ggctgatcat catcaacaaa ccacagcaag    2280
ccatgagatg ggtgtgtact ctgagggatc catcctcatc tcacatagaa actcttccac    2340
agctgcacat gtcccggagc catgggaatc tgtctagtga tcatcgaggt gcactgtttc    2400
tgcaacatgc aggctgggtt tctggcagtg caggagaata aaattgcatg gactttgaaa    2460
ttttgatgtg tttgtgagga tgaaatttga agcactgaat taaagcaaaa tgcatcaaat    2520
gaaaaaaaaa                                                          2530
```

<210> SEQ ID NO 6
<211> LENGTH: 653
<212> TYPE: PRT
<213> ORGANISM: Mouse

<400> SEQUENCE: 6

```
Met Val Lys Asp Leu Ser Ser Thr Pro Ala Cys Glu Leu Asp Lys Phe
1               5                  10                  15

Ile Arg Asp His Leu Leu Pro Asp Ser Ser Phe His Ala Glu Ala Arg
            20                  25                  30

Ala Asp Val Asp Phe Ile Gly Ala Phe Leu Lys Glu Arg Cys Phe Gln
        35                  40                  45

Gly Ala Thr His Pro Val Arg Val Ser Arg Val Met Gly Gly Ser
    50                  55                  60

Tyr Asp Glu His Thr Ala Leu Lys Ser Lys Ser Glu Ala Lys Met Val
65                  70                  75                  80

Val Phe Leu Asn Asn Leu Thr Ser Phe Glu Glu Leu Lys Arg Arg
                85                  90                  95

Gly Glu Phe Ile Glu Glu Ile Arg Lys His Leu Cys Gln Leu Gln Asp
            100                 105                 110

Glu Lys Pro Phe Lys Val Lys Phe Glu Val Gln Ser Ser Glu Glu Pro
        115                 120                 125

Asn Ser Arg Ser Leu Ser Phe Lys Leu Ser Ser Pro Glu Leu Gln Gln
    130                 135                 140

Glu Val Glu Phe Asp Val Gln Pro Ala Tyr Asp Val Leu Tyr Glu Leu
145                 150                 155                 160
```

```
Arg Asn Asn Lys Tyr Ala Glu Leu Tyr Leu Tyr Asn Lys Ile Tyr Ala
                165                 170                 175

Gln Leu Ile His Glu Cys Thr Thr Leu Lys Lys Glu Gly Glu Phe Ser
            180                 185                 190

Ile Cys Phe Thr Asp Leu His Gln Ser Phe Leu Glu Asp Arg Ala Pro
        195                 200                 205

Lys Leu Lys Asn Leu Ile Arg Leu Val Lys His Trp Tyr Gln Leu Cys
    210                 215                 220

Lys Glu Lys Leu Gly Lys Pro Leu Pro Pro Gln Tyr Ala Leu Glu Leu
225                 230                 235                 240

Leu Thr Val Tyr Ala Trp Glu Ser Gly Ser Arg Asp Cys Glu Phe Asn
                245                 250                 255

Thr Ala Gln Gly Phe Arg Thr Val Leu Glu Leu Val Thr Lys Tyr Lys
            260                 265                 270

Trp Leu Arg Ile Tyr Trp Thr Val Tyr Asp Phe Arg Lys Thr Lys
        275                 280                 285

Val Ser Glu Tyr Leu His Lys Met Leu Gln Lys Val Arg Pro Val Ile
    290                 295                 300

Leu Asp Pro Ala Asp Pro Thr Arg Asn Val Ala Gly Thr Asn Leu Leu
305                 310                 315                 320

Gly Trp Gly Leu Leu Ala Lys Glu Ala Ala Ile Trp Leu Gln Ser Ser
                325                 330                 335

Cys Phe Arg Asn Cys Asp Thr Cys Leu Val Gly Pro Trp Gly Val Pro
            340                 345                 350

Gly Gly Ser Tyr Asn Arg Tyr Thr Val Leu Lys Gly Arg Ser Glu Val
        355                 360                 365

Asp Leu Leu Val Phe Phe Asn Asn Leu Thr Cys Phe Asp Asp Gln Phe
    370                 375                 380

Lys Leu Gln Lys Glu Val Ile Glu Glu Ile Gln Lys His Leu Cys Gln
385                 390                 395                 400

Phe Gln Gln Glu Lys Arg Leu Arg Glu Lys Phe Lys Val Gln Ser Ser
                405                 410                 415

Asp Gln Pro Asn Phe Arg Ser Val Ser Phe Lys Leu Ser Tyr Pro Lys
            420                 425                 430

Phe Gln Gln Glu Val Glu Phe His Met Gln Thr Ala Tyr Asp Ala Leu
        435                 440                 445

Tyr Glu Val Arg Arg Lys Glu Asn His Asn Cys Glu Ile Tyr Asn Lys
    450                 455                 460

Val Tyr Ala Arg Leu Ile Arg Glu Cys Thr Met Leu Gly Lys Glu Gly
465                 470                 475                 480

Glu Phe Asn Ile Cys Phe Met Glu Leu Gln Gln Asp Phe Leu Trp Lys
                485                 490                 495

Arg Pro Cys Glu Leu Lys Asn Leu Ile Cys Leu Val Lys His Trp Tyr
            500                 505                 510

Gln Leu Cys Lys Glu Lys Leu Arg Glu Pro Leu Pro Pro Gln Tyr Ala
        515                 520                 525

Leu Glu Leu Leu Thr Val Tyr Ala Trp Glu His Glu Leu Pro Asp Lys
    530                 535                 540

His Glu Thr Gln Thr Ala Arg Gly Phe Arg Thr Val Leu Glu Leu Ile
545                 550                 555                 560

Thr Lys Tyr Leu Cys Leu Arg Ile Tyr Trp Thr Leu Tyr Tyr Asp Val
                565                 570                 575
```

Leu His Glu Gln Val Asn Ala Tyr Leu Tyr Ser Gln Val Lys Arg Val
            580                 585                 590

Ser Pro Leu Ile Leu Asp Pro Ala Asp Pro Thr Trp Asn Val Ala Gly
            595                 600                 605

Leu Asn Leu Gln Gly Trp Cys Ile Leu Ala Glu Ala Lys Ala Trp
        610                 615                 620

Leu Asp Tyr Pro Cys Phe Lys Asn Arg Asp Gly Ser Arg Val Ser Ser
625                 630                 635                 640

Trp Asp Val Pro Pro Asp Lys Lys Gly Phe Val Phe Leu
            645                 650

<210> SEQ ID NO 7
<211> LENGTH: 2054
<212> TYPE: DNA
<213> ORGANISM: Mouse

<400> SEQUENCE: 7

```
aattcgtcga catcgtagcc atggcagtcg cccaggagct gtacggcttc ccggcctcca      60
agctggactc ctttgtggct cagtggctgc agccaaccag agagtggaaa gaagaggtcc     120
tggagaccgt gcagacagtg gagcagttcc tgaggcagga gaatttccgt gaagatcgtg     180
gcccggctcg ggatgtgcgc gtgctcaagg tactcaaggt aggctgcttt gggaatggca     240
ccgtgctcag gagcactaca gacgtggagc tggtcgtgtt cctgagctgt ttccacagct     300
tccaggaaga agccaagcac atcaggctg tcctgagact gatacagaaa aggatgtact     360
actgccagga gctgatggac cttgggctca gtaacctgag tgtgactaac agagtaccca     420
gtagtctcat cttcacgatc cagaccaggg agacctggga gaccatcact gtcaccgttg     480
tgcccgccta cagagccctg ggccttcct gtcccagctc cgaggtctac gcaaatctga     540
tcaaggctaa tgggtaccca ggaaatttct ctccatcctt cagcgagctg cagcgaaact     600
tcgtgaagca tcgccgacg aagctgaaga gcctccttcg gttggtcaaa cactggtacc     660
agcagtatgt gagagacaag tgccccccggg ccaacctgcc ccctctctat gccctggagc     720
tgctcactgt ctatgcctgg gaagcgggca cccgggagga tgccaacttc aggctggatg     780
aaggcctcgc cacggtgatg gagctgctcc aggatcatga gctcctctgt atctactgga     840
ccaagcacta cacgctgcag cacccggtca tcgaggcctg tgtcaggaga cagctcaggg     900
gacaaaggcc tatcatcctg acccagcag accccaccaa caatgtggca gaaggctaca     960
gatgggacat agtggctcag cgggccaacc agtgtctgaa acaggactgt tgctatgaca    1020
acagggacag ccccgtcccc agctggaggg tgaagagagc acccgatatc caggtgaccg    1080
tgcaggagtg ggggcactcg gatttaacct tctgggtgaa cccttatgaa cccataaaga    1140
aactgaaaga gaaaatccaa ctgagccagg gctacttggg cctgcagcgt ctgtcctttc    1200
aggagcccgg cggagaacgt cagctcatca gaagccattg cacgctcgcc tactacggaa    1260
tcttctgcga cacccacatc tgcctgctgg acaccatctc ccctgagatc caggtctttg    1320
tgaaaaaccc ggatggcagg agccacgcct atgcgatcca cccgcttgat tacgtcctga    1380
acctgaagca gcagatagaa gacaggcagg gccttcgatg ccaggagcag cgcctggagt    1440
ccagggccca catcctggag gactggtttg actttaaatc ctatggcatc caagacagtg    1500
tcacagtcat cctgtccaag acgacggagg gggcagctcc atttgtgccc agctagcttc    1560
ctctgtcggt ggctctgcct gttttattgt ctcatcctag actcagccta gttgcctctc    1620
cttcccgtcc tctgcccgga tggtccacgt cttcagtacc ttgccagcag ggagtcagag    1680
```

```
ggggtgtgag aagtcgtgta cagccagaca ctcttgtgtg acaatggaat tctgcagtcc    1740
cctgggaagt catgccagga cctctgcctt cctcgtggcc tcactgtcaa gactgtgtca    1800
gtgaatagct ggcctcacag actattctca catgttcaga gaaagccaaa ccatcttcct    1860
aaccaatcac agggaccctg cttgaggttg tcccacctcc aaattcttcc cagtgacctc    1920
catcagggcg gctctgaagc cttcccctgt gcccccaaac acttctgcct gccttcgact    1980
atccaaggca aggtaggagg ggatcaagtt cctttcaaat ggagaataaa aaagccattg    2040
tttcttccca aaaa                                                      2054
```

<210> SEQ ID NO 8
<211> LENGTH: 511
<212> TYPE: PRT
<213> ORGANISM: Mouse

<400> SEQUENCE: 8

```
Met Ala Val Ala Gln Glu Leu Tyr Gly Phe Pro Ala Ser Lys Leu Asp
1               5                  10                  15

Ser Phe Val Ala Gln Trp Leu Gln Pro Thr Arg Glu Trp Lys Glu Glu
            20                  25                  30

Val Leu Glu Thr Val Gln Thr Val Glu Gln Phe Leu Arg Gln Glu Asn
        35                  40                  45

Phe Arg Glu Asp Arg Gly Pro Ala Arg Asp Val Arg Val Leu Lys Val
    50                  55                  60

Leu Lys Val Gly Cys Phe Gly Asn Gly Thr Val Leu Arg Ser Thr Thr
65                  70                  75                  80

Asp Val Glu Leu Val Val Phe Leu Ser Cys Phe His Ser Phe Gln Glu
                85                  90                  95

Glu Ala Lys His His Gln Ala Val Leu Arg Leu Ile Gln Lys Arg Met
            100                 105                 110

Tyr Tyr Cys Gln Glu Leu Met Asp Leu Gly Leu Ser Asn Leu Ser Val
        115                 120                 125

Thr Asn Arg Val Pro Ser Ser Leu Ile Phe Thr Ile Gln Thr Arg Glu
    130                 135                 140

Thr Trp Glu Thr Ile Thr Val Thr Val Val Pro Ala Tyr Arg Ala Leu
145                 150                 155                 160

Gly Pro Ser Cys Pro Ser Ser Glu Val Tyr Ala Asn Leu Ile Lys Ala
                165                 170                 175

Asn Gly Tyr Pro Gly Asn Phe Ser Pro Ser Phe Ser Glu Leu Gln Arg
            180                 185                 190

Asn Phe Val Lys His Arg Pro Thr Lys Leu Lys Ser Leu Leu Arg Leu
        195                 200                 205

Val Lys His Trp Tyr Gln Gln Tyr Val Arg Asp Lys Cys Pro Arg Ala
    210                 215                 220

Asn Leu Pro Pro Leu Tyr Ala Leu Glu Leu Leu Thr Val Tyr Ala Trp
225                 230                 235                 240

Glu Ala Gly Thr Arg Glu Asp Ala Asn Phe Arg Leu Asp Glu Gly Leu
                245                 250                 255

Ala Thr Val Met Glu Leu Leu Gln Asp His Glu Leu Leu Cys Ile Tyr
            260                 265                 270

Trp Thr Lys His Tyr Thr Leu His Pro Val Ile Glu Ala Cys Val
        275                 280                 285

Arg Arg Gln Leu Arg Gly Gln Arg Pro Ile Ile Leu Asp Pro Ala Asp
    290                 295                 300
```

| | | | | | | | | | | | | |
|---|---|---|---|---|---|---|---|---|---|---|---|---|
| Pro | Thr | Asn | Asn | Val | Ala | Glu | Gly | Tyr | Arg | Trp | Asp | Ile | Val | Ala | Gln |
| 305 | | | | 310 | | | | | 315 | | | | 320 |

Pro Thr Asn Asn Val Ala Glu Gly Tyr Arg Trp Asp Ile Val Ala Gln
305                 310                 315                 320

Arg Ala Asn Gln Cys Leu Lys Gln Asp Cys Cys Tyr Asp Asn Arg Asp
                325                 330                 335

Ser Pro Val Pro Ser Trp Arg Val Lys Arg Ala Pro Asp Ile Gln Val
            340                 345                 350

Thr Val Gln Glu Trp Gly His Ser Asp Leu Thr Phe Trp Val Asn Pro
        355                 360                 365

Tyr Glu Pro Ile Lys Lys Leu Lys Glu Lys Ile Gln Leu Ser Gln Gly
    370                 375                 380

Tyr Leu Gly Leu Gln Arg Leu Ser Phe Gln Glu Pro Gly Gly Glu Arg
385                 390                 395                 400

Gln Leu Ile Arg Ser His Cys Thr Leu Ala Tyr Tyr Gly Ile Phe Cys
                405                 410                 415

Asp Thr His Ile Cys Leu Leu Asp Thr Ile Ser Pro Glu Ile Gln Val
            420                 425                 430

Phe Val Lys Asn Pro Asp Gly Arg Ser His Ala Tyr Ala Ile His Pro
        435                 440                 445

Leu Asp Tyr Val Leu Asn Lys Gln Gln Ile Glu Asp Arg Gln Gly
    450                 455                 460

Leu Arg Cys Gln Glu Gln Arg Leu Glu Phe Gln Gly His Ile Leu Glu
465                 470                 475                 480

Asp Trp Phe Asp Phe Lys Ser Tyr Gly Ile Gln Asp Ser Val Thr Val
                485                 490                 495

Ile Leu Ser Lys Thr Thr Glu Gly Ala Ala Pro Phe Val Pro Ser
            500                 505                 510

```
<210> SEQ ID NO 9
<211> LENGTH: 3884
<212> TYPE: DNA
<213> ORGANISM: Mouse

<400> SEQUENCE: 9
aaacccgggt gcacggcaga aggcccagga cttgagctac agtgctctgc ctcgacaatt    60
gacaagacca gctagcaacg atgggaaact ggctgactgg aaactggtca tctgacaggt   120
catctggcta ttcatctggc tggtcaccct gtgggtcttc agggggtgccc tccgggccag   180
tgcacaagtt agaaaagtct atccaggcaa acctcacacc caacgaaaac tgtctgaagc   240
agattgcggt gtcctcggtg ccatcgcaga agctagaagg gtatatccag gaaaacctca   300
aacctaacag agaatctctg aagcagatag accaggccgt ggatgccatc tgggacctgc   360
tgcgcagtca gatccctgtg aaggaagtgg ctaaggtggg ctcctatggc cgggaaacag   420
ccctaagagg ctgctccgat ggtacccttg ttctcttcat ggactgcttc aacagttcc    480
aggatcagat aaaataccaa gatgcatacc ttgacgtcat tgaactgtgg ctgaaaatcc   540
atgagaagaa gtcagtaaag catgaacatg cccttgtagt acaagtgtct gtaccagggc   600
agagaatact cctgcaatta cttccagtct tcaatcctct acgctccaat gagaatccca   660
gctcctgtgt ctatgtggat ctcaaaaaat ccatggatca agtaagagcc tcaccagggg   720
agttctcaga ctgcttcacc acactgcagc agcggttttt caagaaatat ccccaaagac   780
tgaaggattt gatcctattg gtcaagcact ggtatgaaca gtgccaggag aagtggaaaa   840
cacccccacc tcagccattg ctgtacgcac tggaactgct cactgtgtgt gcctgggaac   900
agggctgcca agctgaagac ttcgacatgg cacaaggcgt caggaccgtg ctgcgactta   960
```

-continued

```
tccagcggcc gacagagctg tgtgtctact ggacagtcaa ttacaacttt gaggatgaga      1020
cagtccggaa catccttctg caccagctca ggtcccaaag accagtcatc ttggatccaa      1080
ctgacccaac caataatgtg ggcaaagatg atgggttctg ggagctactg acagaggaag      1140
ctatggcctg gctgtactct cccagcctga atactgagtc acctgcacca tattgggatg      1200
ttctgcccat gccactttc gtcactccaa gccacttact gaacaagttc atcaaggact       1260
ttctccagcc caacaagctc ttcctaaagc agatcaagga agctgttgac attatatgtt      1320
ccttccttaa aaatgtctgc ttcttgaatt ctgacaccaa agtcctgaag accgtcaagg      1380
gaggatccac tgccaaaggc acagctctga agcgggatc agatgctgac attgttgtgt       1440
tcctctcctc gctggagagt tacgactctc taaaaaccaa ccgctcccag ttcgtccagg      1500
agatccagaa gcagttagaa gaattcgtgc aggcgcagga gtgggaggtg acgtttgaga      1560
tttcaaaatg gaaggctccc agagtgctga gttttacctt gaaatccaag actctcaatg     1620
aaagtgtcga gttcgatgtc cttcccgcct atgatgcact aggtcaactg cggtctgact      1680
tcaccctcag gcccgaagcc tacaaggatc tcattgagct gtgtgcatca caggacatca      1740
aagaaggaga gttttctatc tgttttactg agctgcagag aaacttcatt caaacccggc      1800
ccaccaaact gaagagtcta ctccgcctga tcaagcactg gtacaaacag tatgaaagga      1860
agatgaagcc aaaagcatct ttaccccaa agtacgccct ggagctgctc accgtgtatg       1920
cctgggagca gggcagtggc acagatgact ttgacattgc tgaaggcttc cggaccgtcc      1980
tggacctggt tataaaatac cggcagctct gcatcttctg gacagtcaat tacaactttg      2040
aagaggaata catgcggaag ttcctactga cccagatcca gaaaagagg cctgtaatcc       2100 tggatccagc agatcccaca ggcgatgtgg gaggaggtga ccgctggtgc tggcatcttc      2160
tagctgaaga agcgaaggag tggctgtcct cccccttgttt ccaagtggag caaaaggcc     2220 tggtacagcc ttggaaagtg ccagtaatgc agaccccgg aagctgtgga ggtcagatct       2280
accccactgt gggtggagtt actaagtagg agtccattca gctctggaag acgcttctgg      2340
agtgatctgg caaagactca gactgtgtta gaaaagggag cctggttcag tcctctctgg      2400
caggctcgca cctctattct tccttcttgg aatcaagaca tgggattatc cttcctcctc      2460
ccccagggtc tcacagcaca ggccctgctc tgtgtgagtg acctccttca gagacacttg      2520
ccccatgcag ctcgatgggt tctggttttg tctgtattct gtgcagttat tttcctgcct      2580
cctgctctgt tagtctctag tcagcagctc cagactcacc ctgtgtcact aaggttaagg      2640
ccctccctag cccttcagca ttgtcaatcc caactagccc tcggagtctt ccattgtgcg      2700
tctttgcctg tctcttccc tgtccctgtg gatacagaga tgtaccatcc atccagcagc       2760
tagccaactc ccctccctcc acctctgctg ttaaaaccct ttctcttggg gaaatgtaaa      2820
caatatctac ctctcttaat gtcccaggac aaactaagct gcatttctcc cttccctgag      2880
aagccaaagc ttccctgatt gagcttagct gctcacagga gaggggttac aggcctttga      2940
agctgccaca ctagaagatc tgcacccagc tagatgggtg cagatggctt ccctggggct      3000
gcataaagag aaccctccc ctcatctttc ctcctgtatc ctctagcccc tctcagagat       3060
cctgtgcaat cagggcagaa tagcatgcag ctggttgaaa ccacttgcta ataactcag       3120 gtgagggtcc cataaccttc ccagcccacc tcccttccaa gagtgaagat aacagtcaac      3180
aagcccagct gtgatgttca ttgataagca ggctctggtg gactcctaaa gatggtgcca      3240
gtgtggctca gtgaatagcc ctgcataaca ttttacacac accaaatgct ggttgatatc      3300
tcttgctggc tgcccaggga gccttcaccc cagggcttta actgcacaga gacatgaggt      3360
```

-continued

```
ctaagccctt cgcatcccca agtaaggctg agccttttt  ctgcctgtgc ttgctctgat   3420
gcattgagga tcatgcctgg ccactgtgca acttttaagc agagccgtgc aacatcccag   3480
ggagttgact tctatgtaaa caccttcatc catttctgat gtatgctttg aggtggctca   3540
ggctgggcta gcccagccca gacagaaatc ctaggcatgt gattagagga tcagaaccct   3600
tctggccctt cttcagggga gagatggggc tgaaggtggg gttcaaatct catgccgagt   3660
gatggaaccc gacatcccta ggtgctaagg ccccaccaaa ttctctggat aaggaagttc   3720
caggaatctt tactgataaa catcccaatg tatcaacaag gtagactctg acctccatgg   3780
gacagaagga tcctgggtca gtcccctccc tggggactct gcagttggct gttcatttat   3840
atgcttcata taaatggtt  tctttgtgta aaaaaaaaaa aaaa               3884
```

<210> SEQ ID NO 10
<211> LENGTH: 742
<212> TYPE: PRT
<213> ORGANISM: Mouse

<400> SEQUENCE: 10

```
Met Gly Asn Trp Leu Thr Gly Asn Trp Ser Ser Asp Arg Ser Ser Gly
1               5                   10                  15

Tyr Ser Ser Gly Trp Ser Pro Gly Gly Ser Ser Gly Val Pro Ser Gly
            20                  25                  30

Pro Val His Lys Leu Glu Lys Ser Ile Gln Ala Asn Leu Thr Pro Asn
        35                  40                  45

Glu Asn Cys Leu Lys Gln Ile Ala Val Ser Val Pro Ser Gln Lys
    50                  55                  60

Leu Glu Gly Tyr Ile Gln Glu Asn Leu Lys Pro Asn Arg Glu Ser Leu
65                  70                  75                  80

Lys Gln Ile Asp Gln Ala Val Asp Ala Ile Trp Asp Leu Leu Arg Ser
                85                  90                  95

Gln Ile Pro Val Lys Glu Val Ala Lys Gly Ser Tyr Gly Arg Glu
            100                 105                 110

Thr Ala Leu Arg Gly Cys Ser Asp Gly Thr Leu Val Leu Phe Met Asp
        115                 120                 125

Cys Phe Gln Gln Phe Gln Asp Gln Ile Lys Tyr Gln Asp Ala Tyr Leu
    130                 135                 140

Asp Val Ile Glu Leu Trp Leu Lys Ile His Glu Lys Lys Ser Val Lys
145                 150                 155                 160

His Glu His Ala Leu Val Val Gln Val Ser Val Pro Gly Gln Arg Ile
                165                 170                 175

Leu Leu Gln Leu Leu Pro Val Phe Asn Pro Leu Arg Ser Asn Glu Asn
            180                 185                 190

Pro Ser Ser Cys Val Tyr Val Asp Leu Lys Lys Ser Met Asp Gln Val
        195                 200                 205

Arg Ala Ser Pro Gly Glu Phe Ser Asp Cys Phe Thr Thr Leu Gln Gln
    210                 215                 220

Arg Phe Phe Lys Lys Tyr Pro Gln Arg Leu Lys Asp Leu Ile Leu Leu
225                 230                 235                 240

Val Lys His Trp Tyr Glu Gln Cys Gln Glu Lys Trp Lys Thr Pro Pro
                245                 250                 255

Pro Gln Pro Leu Leu Tyr Ala Leu Glu Leu Leu Thr Val Cys Ala Trp
            260                 265                 270

Glu Gln Gly Cys Gln Ala Glu Asp Phe Asp Met Ala Gln Gly Val Arg
```

-continued

```
            275                 280                 285
Thr Val Leu Arg Leu Ile Gln Arg Pro Thr Glu Leu Cys Val Tyr Trp
290                 295                 300
Thr Val Asn Tyr Asn Phe Glu Asp Glu Thr Val Arg Asn Ile Leu Leu
305                 310                 315                 320
His Gln Leu Arg Ser Gln Arg Pro Val Ile Leu Asp Pro Thr Asp Pro
                325                 330                 335
Thr Asn Asn Val Gly Lys Asp Asp Gly Phe Trp Glu Leu Leu Thr Glu
                340                 345                 350
Glu Ala Met Ala Trp Leu Tyr Ser Pro Ser Leu Asn Thr Glu Ser Pro
                355                 360                 365
Ala Pro Tyr Trp Asp Val Leu Pro Met Pro Leu Phe Val Thr Pro Ser
370                 375                 380
His Leu Leu Asn Lys Phe Ile Lys Asp Phe Leu Gln Pro Asn Lys Leu
385                 390                 395                 400
Phe Leu Lys Gln Ile Lys Glu Ala Val Asp Ile Ile Cys Ser Phe Leu
                405                 410                 415
Lys Asn Val Cys Phe Leu Asn Ser Asp Thr Lys Val Leu Lys Thr Val
                420                 425                 430
Lys Gly Gly Ser Thr Ala Lys Gly Thr Ala Leu Lys Arg Gly Ser Asp
                435                 440                 445
Ala Asp Ile Val Val Phe Leu Ser Ser Leu Glu Ser Tyr Asp Ser Leu
                450                 455                 460
Lys Thr Asn Arg Ser Gln Phe Val Gln Glu Ile Gln Lys Gln Leu Glu
465                 470                 475                 480
Glu Phe Val Gln Ala Gln Glu Trp Glu Val Thr Phe Glu Ile Ser Lys
                485                 490                 495
Trp Lys Ala Pro Arg Val Leu Ser Phe Thr Leu Lys Ser Lys Thr Leu
                500                 505                 510
Asn Glu Ser Val Glu Phe Asp Val Leu Pro Ala Tyr Asp Ala Leu Gly
                515                 520                 525
Gln Leu Arg Ser Asp Phe Thr Leu Arg Pro Glu Ala Tyr Lys Asp Leu
530                 535                 540
Ile Glu Leu Cys Ala Ser Gln Asp Ile Lys Glu Gly Glu Phe Ser Ile
545                 550                 555                 560
Cys Phe Thr Glu Leu Gln Arg Asn Phe Ile Gln Thr Arg Pro Thr Lys
                565                 570                 575
Leu Lys Ser Leu Leu Arg Leu Ile Lys His Trp Tyr Lys Gln Tyr Glu
                580                 585                 590
Arg Lys Met Lys Pro Lys Ala Ser Leu Pro Pro Lys Tyr Ala Leu Glu
                595                 600                 605
Leu Leu Thr Val Tyr Ala Trp Glu Gln Gly Ser Gly Thr Asp Asp Phe
610                 615                 620
Asp Ile Ala Glu Gly Phe Arg Thr Val Leu Asp Leu Val Ile Lys Tyr
625                 630                 635                 640
Arg Gln Leu Cys Ile Phe Trp Thr Val Asn Tyr Asn Phe Glu Glu Glu
                645                 650                 655
Tyr Met Arg Lys Phe Leu Leu Thr Gln Ile Gln Lys Lys Arg Pro Val
                660                 665                 670
Ile Leu Asp Pro Ala Asp Pro Thr Gly Asp Val Gly Gly Gly Asp Arg
                675                 680                 685
Trp Cys Trp His Leu Leu Ala Glu Glu Ala Lys Glu Trp Leu Ser Ser
690                 695                 700
```

```
Pro Cys Phe Gln Val Glu Gln Lys Gly Leu Val Gln Pro Trp Lys Val
705                 710                 715                 720

Pro Val Met Gln Thr Pro Gly Ser Cys Gly Gly Gln Ile Tyr Pro Thr
                725                 730                 735

Val Gly Gly Val Thr Lys
            740
```

<210> SEQ ID NO 11
<211> LENGTH: 1831
<212> TYPE: DNA
<213> ORGANISM: Mouse

<400> SEQUENCE: 11

```
tttctagttc agccagccta ggagacacag gacctgctgg ctgcagaggt aaaagctgga     60
cctaggatgg agcaggatct gaggagcatc ccggcctcga agcttgataa gttcatagag    120
aaccatctcc cggacaccag cttctgtgct gacctcagag aagtcataga tgccctgtgt    180
gctctcctga aggacagatc cttccggggc cccgtccgcc gaatgagggc ctctaaaggg    240
gtcaagggca aggcaccgc gctcaagggc aggtcagacg ctgacctggt ggtgttcctt     300
aacaatctca ccagctttga ggatcagtta accaacagg gagtgttgat taggaaaatt     360
aagaaacagc tgtgcgaggt tcagcatgag agacgttgtg gagtgaagtt tgaggtccac    420
agtttaagga gtcccaactc ccgggctctg agcttcaagc tgagcgcccc cgacctgctg    480
aaggaggtga agtttgatgt gctgccagcc tatgatttac tggatcatct taacatcctc    540
aagaagccta accaacaatt ctacgccaat ctcatcagtg gcgtaccgc cgggaaggag     600
ggcaagttat cgatctgctt tatggggctt cagaagtact tcctgaactg tcgcccaacc    660
aagctgaagc gcctcatccg cctggtcacg cactggtacc aactgtgtaa ggagaagctg    720
ggggaccccg ctgcccccaca gtatgccctg gagctgctca cactcgatgc ctgggagtat    780
gggagtcgag taactaaatt caacacagcc cagggcttct gaaccgtctt ggaactggtc    840
accaagtaca aacagcttca aatctactgg acagtgtatt atgactttcg acatcaagag    900
gtctctgaat acctgcacca acagctcaaa aaagacaggc ctgtgatctt ggaccccact    960
gacccaacaa ggaacatagc cggtttgaac ccaaaggact ggaggcgtct agcaggagag   1020
gctgccgcct ggctgcaata cccatgcttt aagtacaggg acggttcctc agtgtgctcc   1080
tgggaggtgc cgacggaggt tgcagtgcca acgaagtatc tcttttgtcg tattttctgg   1140
ttattgtttt ggtctttgtt tcatttcatc tttgggaaga cttcatctgg atagcccaga   1200
gtgtcttgga tattgccatc ctcctgcctt agcgctggca tgactgcagc gtaggcctgg   1260
tatgccctgc ctccttccat cctcaagtgg acaagaactg gcatgtgtt ttcctgtgag    1320
cccagtggga cctgtccagg atgctccaga gtcagacgca tgtcctgctc tgctgcaggg   1380
ccttgaccca gagaagacag gaaggtgccc aaagcccaag agagggaggg tccaacctgt   1440
gatcagactc caggcttctg tcccctgccc tcaacccctg cacagacagc ctttctcaca   1500
gcctgcttta tctgccttgt cccccaacag tgttctctgg gagacaagag attcagaagg   1560
agaatattat ggtttgtata tggttggccc agggaatggc actgttagga ggtgtggcca   1620
tgttggagtg ggtgtggcct tgtgggtgtg ggctttctct tgtcttagct gcctggaagt   1680
cagtattctg ctagcagcct tcagatgaag atgtagaact ctcagctcct cctgcaccat   1740
gcctgcctgg acgttgccat gctccttgcct tggtttataat ggactgaacg tctgaacctg   1800
taagccaacc ccaattaaat gttgtttttta t                                   1831
```

<210> SEQ ID NO 12
<211> LENGTH: 251
<212> TYPE: PRT
<213> ORGANISM: Mouse

<400> SEQUENCE: 12

Met Glu Gln Asp Leu Arg Ser Ile Pro Ala Ser Lys Leu Asp Lys Phe
1               5                   10                  15

Ile Glu Asn His Leu Pro Asp Thr Ser Phe Cys Ala Asp Leu Arg Glu
            20                  25                  30

Val Ile Asp Ala Leu Cys Ala Leu Leu Lys Asp Arg Ser Phe Arg Gly
        35                  40                  45

Pro Val Arg Arg Met Arg Ala Ser Lys Gly Val Lys Gly Lys Gly Thr
    50                  55                  60

Ala Leu Lys Gly Arg Ser Asp Ala Asp Leu Val Val Phe Leu Asn Asn
65                  70                  75                  80

Leu Thr Ser Phe Glu Asp Gln Leu Asn Gln Gln Gly Val Leu Ile Lys
                85                  90                  95

Glu Ile Lys Lys Gln Leu Cys Glu Val Gln His Glu Arg Arg Cys Gly
            100                 105                 110

Val Lys Phe Glu Val His Ser Leu Arg Ser Pro Asn Ser Arg Ala Leu
        115                 120                 125

Ser Phe Lys Leu Ser Ala Pro Asp Leu Leu Lys Glu Val Lys Phe Asp
    130                 135                 140

Val Leu Pro Ala Tyr Asp Leu Leu Asp His Leu Asn Ile Leu Lys Lys
145                 150                 155                 160

Pro Asn Gln Gln Phe Tyr Ala Asn Leu Ile Ser Gly Val Pro Ala Gly
                165                 170                 175

Lys Glu Gly Lys Leu Ser Ile Cys Phe Met Gly Leu Gln Lys Tyr Phe
            180                 185                 190

Leu Asn Cys Arg Pro Thr Lys Leu Lys Arg Leu Ile Arg Leu Val Thr
        195                 200                 205

His Trp Tyr Gln Leu Cys Lys Glu Lys Leu Gly Asp Pro Leu Pro Pro
    210                 215                 220

Gln Tyr Ala Leu Glu Leu Leu Thr Leu Asp Ala Trp Glu Tyr Gly Ser
225                 230                 235                 240

Arg Val Thr Lys Phe Asn Thr Ala Gln Gly Phe
                245                 250

<210> SEQ ID NO 13
<211> LENGTH: 367
<212> TYPE: PRT
<213> ORGANISM: Mouse

<400> SEQUENCE: 13

Met Glu His Gly Leu Arg Ser Ile Pro Ala Trp Thr Leu Asp Lys Phe
1               5                   10                  15

Ile Glu Asp Tyr Leu Leu Pro Asp Thr Thr Phe Gly Ala Asp Val Lys
            20                  25                  30

Ser Ala Val Asn Val Val Cys Asp Phe Leu Lys Glu Arg Cys Phe Gln
        35                  40                  45

Gly Ala Ala His Pro Val Arg Val Ser Lys Val Val Lys Gly Gly Ser
    50                  55                  60

Ser Gly Lys Gly Thr Thr Leu Lys Gly Arg Ser Asp Ala Asp Leu Val
65                  70                  75                  80

```
Val Phe Leu Asn Asn Leu Thr Ser Phe Glu Asp Gln Leu Asn Arg Arg
                 85                  90                  95

Gly Glu Phe Ile Lys Glu Ile Lys Lys Gln Leu Tyr Glu Val Gln His
                100                 105                 110

Glu Arg Arg Phe Arg Val Lys Phe Glu Val Gln Ser Ser Trp Trp Pro
                115                 120                 125

Asn Ala Arg Ser Leu Ser Phe Lys Leu Ser Ala Pro His Leu His Gln
                130                 135                 140

Glu Val Glu Phe Asp Val Leu Pro Ala Phe Asp Val Leu Gly His Val
145                 150                 155                 160

Asn Thr Ser Ser Lys Pro Asp Pro Arg Ile Tyr Ala Ile Leu Ile Glu
                165                 170                 175

Glu Cys Thr Ser Leu Gly Lys Asp Gly Glu Phe Ser Thr Cys Phe Thr
                180                 185                 190

Glu Leu Gln Arg Asn Phe Leu Lys Gln Arg Pro Thr Lys Leu Lys Ser
                195                 200                 205

Leu Ile Arg Leu Val Lys His Trp Tyr Gln Leu Cys Lys Glu Lys Leu
210                 215                 220

Gly Lys Pro Leu Pro Pro Gln Tyr Ala Leu Glu Leu Leu Thr Val Phe
225                 230                 235                 240

Ala Trp Glu Gln Gly Asn Gly Cys Tyr Glu Phe Asn Thr Ala Gln Gly
                245                 250                 255

Phe Arg Thr Val Leu Glu Leu Val Ile Asn Tyr Gln His Leu Arg Ile
                260                 265                 270

Tyr Trp Thr Lys Tyr Tyr Asp Phe Gln His Gln Glu Val Ser Lys Tyr
                275                 280                 285

Leu His Arg Gln Leu Arg Lys Ala Arg Pro Val Ile Leu Asp Pro Ala
                290                 295                 300

Asp Pro Thr Gly Asn Val Ala Gly Gly Asn Pro Glu Gly Trp Arg Arg
305                 310                 315                 320

Leu Ala Glu Glu Ala Asp Val Trp Leu Trp Tyr Pro Cys Phe Ile Lys
                325                 330                 335

Lys Asp Gly Ser Arg Val Ser Ser Trp Asp Val Pro Thr Val Val Pro
                340                 345                 350

Val Pro Phe Glu Gln Val Glu Gly Asn Trp Thr Cys Ile Leu Leu
                355                 360                 365

<210> SEQ ID NO 14
<211> LENGTH: 376
<212> TYPE: PRT
<213> ORGANISM: Mouse

<400> SEQUENCE: 14

Met Glu Gln Asp Leu Arg Ser Ile Pro Ala Ser Lys Leu Asp Lys Phe
1               5                   10                  15

Ile Glu Asn His Leu Pro Asp Thr Ser Phe Cys Ala Asp Leu Arg Glu
                20                  25                  30

Val Ile Asp Ala Leu Cys Ala Leu Leu Lys Asp Arg Phe Phe Arg Gly
                35                  40                  45

Pro Val Arg Arg Met Arg Ala Ser Lys Gly Val Lys Gly Lys Cys Thr
                50                  55                  60

Ala Leu Lys Gly Arg Ser Asp Ala Asp Leu Val Val Phe Leu Asn Asn
65                  70                  75                  80

Leu Thr Tyr Phe Glu Asp Gln Leu Asn Gln Gln Gly Val Leu Ile Lys
```

```
                    85                  90                  95
Glu Ile Lys Lys Gln Leu Tyr Glu Val Gln His Glu Arg Arg Phe Gly
                100                 105                 110

Val Lys Phe Glu Val Gln Ser Leu Arg Ser Pro Asn Ser Arg Ala Leu
            115                 120                 125

Ser Phe Lys Leu Ser Ala Pro Asp Leu Leu Lys Glu Val Lys Phe Asp
    130                 135                 140

Val Leu Pro Ala Tyr Asp Leu Leu Asp His Leu Asn Ile Leu Lys Lys
145                 150                 155                 160

Pro Asn Gln Gln Phe Tyr Ala Asn Leu Ile Ser Gly Arg Thr Pro Leu
                165                 170                 175

Gly Lys Glu Gly Lys Leu Leu Thr Cys Phe Met Gly Leu Arg Lys Tyr
            180                 185                 190

Phe Leu Asn Cys Arg Pro Thr Lys Leu Lys Arg Leu Ile His Leu Val
    195                 200                 205

Thr His Trp Tyr Gln Leu Cys Lys Glu Lys Leu Gly Asp Pro Leu Pro
            210                 215                 220

Pro Gln Tyr Ala Leu Glu Leu Leu Thr Val Tyr Ala Trp Glu Tyr Gly
225                 230                 235                 240

Ser Arg Val Thr Lys Phe Asn Thr Ala Gln Gly Phe Arg Thr Val Leu
                245                 250                 255

Glu Leu Val Thr Lys Tyr Lys Gln Leu Arg Ile Tyr Trp Thr Val Tyr
            260                 265                 270

Tyr Asp Phe Arg His Gln Glu Val Ser Glu Tyr Leu His Gln Gln Leu
    275                 280                 285

Lys Lys Asp Arg Pro Val Ile Leu Asp Pro Ala Asp Pro Thr Arg Asn
290                 295                 300

Ile Ala Gly Leu Asn Pro Lys Asp Trp Arg Arg Leu Ala Gly Glu Ala
305                 310                 315                 320

Ala Ala Trp Leu Gln Tyr Pro Cys Phe Lys Tyr Arg Asp Gly Ser Pro
                325                 330                 335

Val Cys Ser Trp Glu Val Pro Thr Glu Val Ala Val Pro Thr Lys Tyr
            340                 345                 350

Leu Phe Cys Arg Ile Phe Trp Leu Leu Phe Trp Ser Leu Phe His Phe
    355                 360                 365

Ile Phe Gly Lys Thr Ser Ser Gly
            370                 375

<210> SEQ ID NO 15
<211> LENGTH: 358
<212> TYPE: PRT
<213> ORGANISM: Mouse

<400> SEQUENCE: 15

Met Glu His Gly Leu Arg Ser Ile Pro Ala Trp Thr Leu Asp Lys Phe
1               5                   10                  15

Ile Glu Asp Tyr Leu Leu Pro Asp Thr Thr Phe Gly Ala Asp Val Lys
            20                  25                  30

Ser Ala Val Asn Val Val Cys Asp Phe Leu Lys Glu Arg Cys Phe Gln
        35                  40                  45

Gly Ala Ala His Pro Val Arg Val Ser Lys Val Val Lys Gly Gly Ser
    50                  55                  60

Ser Gly Lys Gly Thr Thr Leu Lys Gly Arg Ser Asp Ala Asp Leu Val
65              70                  75                  80
```

```
Val Phe Leu Asn Asn Leu Thr Ser Phe Glu Asp Gln Leu Asn Arg Arg
                85                  90                  95

Gly Glu Phe Ile Lys Glu Ile Lys Lys Gln Leu Tyr Glu Val Gln His
            100                 105                 110

Glu Arg Arg Phe Arg Val Lys Phe Glu Val Gln Ser Ser Trp Trp Pro
        115                 120                 125

Asn Ala Arg Ser Leu Ser Phe Lys Leu Ser Ala Pro His Leu His Gln
    130                 135                 140

Glu Val Glu Phe Asp Val Leu Pro Ala Phe Asp Val Leu Gly His Gly
145                 150                 155                 160

Ser Ile Asn Lys Lys Pro Asn Pro Leu Ile Tyr Thr Ile Leu Ile Trp
                165                 170                 175

Glu Cys Thr Ser Leu Gly Lys Asp Gly Glu Phe Ser Thr Cys Phe Thr
            180                 185                 190

Glu Leu Gln Arg Asn Phe Leu Lys Gln Arg Pro Thr Lys Leu Lys Ser
        195                 200                 205

Leu Ile Arg Leu Val Lys His Trp Tyr Gln Leu Cys Lys Glu Lys Leu
    210                 215                 220

Gly Lys Pro Leu Pro Pro Gln Tyr Ala Leu Glu Leu Leu Thr Val Tyr
225                 230                 235                 240

Ala Trp Glu Gln Gly Asn Gly Cys Asn Glu Phe Asn Thr Ala Gln Gly
                245                 250                 255

Phe Arg Thr Val Leu Glu Leu Val Ile Asn Tyr Gln His Leu Arg Ile
            260                 265                 270

Tyr Trp Thr Lys Tyr Tyr Asp Phe Gln His Lys Glu Val Ser Lys Tyr
        275                 280                 285

Leu His Arg Gln Leu Arg Lys Ala Arg Pro Val Ile Leu Asp Pro Ala
    290                 295                 300

Asp Pro Thr Gly Asn Val Ala Gly Gly Asn Pro Glu Gly Trp Arg Arg
305                 310                 315                 320

Leu Ala Glu Glu Ala Asp Val Trp Leu Trp Tyr Pro Cys Phe Met Lys
                325                 330                 335

Asn Asp Gly Ser Arg Val Ser Ser Trp Asp Val Pro Thr Val Val Pro
            340                 345                 350

Val Pro Phe Glu Gln Val
        355

<210> SEQ ID NO 16
<211> LENGTH: 473
<212> TYPE: PRT
<213> ORGANISM: Mouse

<400> SEQUENCE: 16

Met Asp Pro Phe Pro Asp Leu Tyr Ala Thr Pro Gly Asp Ser Leu Asp
1               5                   10                  15

His Phe Leu Glu His Ser Leu Gln Pro Gln Arg Asp Trp Lys Glu Glu
            20                  25                  30

Gly Gln Asp Ala Trp Glu Arg Ile Glu Arg Phe Phe Arg Glu Gln Cys
        35                  40                  45

Phe Arg Asp Glu Leu Leu Leu Asp Gln Glu Val Arg Val Ile Lys Val
    50                  55                  60

Val Lys Gly Gly Ser Ser Gly Lys Gly Thr Thr Leu Asn His Arg Ser
65                  70                  75                  80

Asp Gln Asp Met Ile Leu Phe Leu Ser Cys Phe Ser Ser Phe Glu Glu
                85                  90                  95
```

```
Gln Ala Arg Asn Arg Glu Val Val Ile Ser Phe Ile Lys Lys Arg Leu
            100                 105                 110

Ile His Cys Ser Arg Ser Leu Ala Tyr Asn Ile Ile Val Leu Thr His
        115                 120                 125

Arg Glu Gly Lys Arg Ala Pro Arg Ser Leu Thr Leu Lys Val Gln Ser
    130                 135                 140

Arg Lys Thr Asp Asp Ile Ile Trp Met Asp Ile Leu Pro Ala Tyr Asp
145                 150                 155                 160

Ala Leu Gly Pro Ile Ser Arg Asp Ser Lys Pro Ala Pro Ala Ile Tyr
                165                 170                 175

Glu Thr Leu Ile Arg Ser Lys Gly Tyr Pro Gly Asp Phe Ser Pro Ser
            180                 185                 190

Phe Thr Glu Leu Gln Arg His Phe Val Lys Thr Arg Pro Val Lys Leu
        195                 200                 205

Lys Asn Leu Leu Arg Leu Val Lys Phe Trp Tyr Leu Gln Cys Leu Arg
    210                 215                 220

Arg Lys Tyr Gly Arg Gly Ala Val Leu Pro Ser Lys Tyr Ala Leu Glu
225                 230                 235                 240

Leu Leu Thr Ile Tyr Ala Trp Glu Met Gly Thr Glu Ser Ser Asp Ser
                245                 250                 255

Phe Asn Leu Asp Glu Gly Phe Val Ala Val Met Glu Leu Leu Val Asn
            260                 265                 270

Tyr Arg Asp Ile Cys Ile Tyr Trp Thr Lys Tyr Tyr Asn Phe Gln Asn
        275                 280                 285

Glu Val Val Arg Asn Phe Leu Lys Lys Gln Leu Lys Gly Asp Arg Pro
    290                 295                 300

Ile Ile Leu Asp Pro Ala Asp Pro Thr Asn Asn Leu Gly Arg Arg Lys
305                 310                 315                 320

Gly Trp Glu Gln Val Ala Ala Glu Ala Ala Phe Cys Leu Leu Gln Val
                325                 330                 335

Cys Cys Thr Thr Val Gly Pro Ser Glu Arg Trp Asn Val Gln Arg Ala
            340                 345                 350

Arg Asp Val Gln Val Arg Val Lys Gln Thr Gly Thr Val Asp Trp Thr
        355                 360                 365

Leu Trp Thr Asn Pro Tyr Ser Pro Ile Arg Lys Met Lys Ala Glu Ile
    370                 375                 380

Arg Arg Glu Lys Asn Phe Gly Gly Glu Leu Arg Ile Ser Phe Gln Glu
385                 390                 395                 400

Pro Gly Gly Glu Arg Gln Leu Leu Ser Ser Arg Lys Thr Leu Ala Asp
                405                 410                 415

Tyr Gly Ile Phe Ser Lys Val Asn Ile Gln Val Leu Glu Thr Phe Pro
            420                 425                 430

Pro Glu Ile Leu Val Phe Val Lys Tyr Pro Gly Gly Gln Ser Lys Pro
        435                 440                 445

Phe Thr Ile Asp Pro Asp Asp Thr Ile Leu Asp Leu Lys Glu Lys Ile
    450                 455                 460

Glu Asp Ala Gly Ala Gly Gly Leu Thr
465                 470

<210> SEQ ID NO 17
<211> LENGTH: 362
<212> TYPE: PRT
<213> ORGANISM: Mouse
```

<400> SEQUENCE: 17

```
Met Glu Asn Gly Leu Cys Ser Ile Gln Ala Arg Glu Leu Asp Glu Phe
1               5                   10                  15

Ile Cys Asp Tyr Leu Phe Pro Asp Thr Thr Phe Leu Thr Glu Leu Arg
            20                  25                  30

Ala Asp Ile Asp Ser Ile Ser Ala Phe Leu Lys Glu Arg Cys Phe Gln
        35                  40                  45

Gly Ala Ala His Pro Val Arg Val Ser Arg Val Val Met Gly Gly Ser
    50                  55                  60

Tyr Asp Glu His Thr Ala Leu Lys Gly Lys Ser Glu Ala Lys Met Val
65                  70                  75                  80

Leu Phe Phe Asn Asn Leu Thr Ser Phe Glu Glu Gln Leu Lys Arg Arg
                85                  90                  95

Gly Glu Phe Val Glu Glu Ile Gln Lys His Leu Cys Gln Leu Gln Gln
            100                 105                 110

Glu Lys Pro Phe Lys Val Lys Phe Glu Val Gln Ser Ser Glu Glu Pro
        115                 120                 125

Asn Ser Arg Ser Leu Ser Phe Lys Leu Ser Ser Pro Glu Leu Gln Gln
130                 135                 140

Glu Val Glu Phe Asp Val Gln Pro Ala Tyr Asp Val Leu Tyr Glu Leu
145                 150                 155                 160

Arg Asn Asn Thr Tyr Ala Glu Pro Gln Phe Tyr Asn Lys Val Tyr Ala
                165                 170                 175

Gln Leu Ile His Glu Cys Thr Thr Leu Glu Lys Glu Gly Asp Phe Ser
            180                 185                 190

Ile Cys Phe Thr Asp Leu His Gln Asn Phe Met Arg Tyr Arg Ala Pro
        195                 200                 205

Lys Leu Trp Asn Leu Ile Arg Leu Val Lys His Trp Tyr Gln Leu Cys
210                 215                 220

Lys Glu Lys Leu Arg Glu Pro Leu Pro Pro Gln Tyr Ala Leu Glu Leu
225                 230                 235                 240

Leu Thr Val Tyr Val Trp Glu His Ser Asn Lys Asn Gln Glu Lys Val
                245                 250                 255

Thr Thr Ala Lys Asn Phe Arg Thr Phe Leu Glu Leu Val Ala Tyr Tyr
            260                 265                 270

Lys Asn Leu Arg Ile Tyr Trp Thr Trp Tyr Tyr Asp Phe Arg His Gln
        275                 280                 285

Glu Val Cys Ala Tyr Leu Cys Arg Gln Leu Lys Lys Ala Arg Pro Leu
    290                 295                 300

Ile Leu Asp Pro Ala Asp Pro Thr Arg Asn Val Ala Gly Ser Asp Leu
305                 310                 315                 320

Gln Ala Trp Asp Leu Leu Ala Lys Glu Ala Gln Thr Trp Met Gln Ser
                325                 330                 335

Ser Cys Phe Arg Asn Cys Asp Met Ser Phe Val Pro Thr Trp Asp Leu
            340                 345                 350

Ser Pro Glu Arg Gln Glu Cys Ala Phe Gln
        355                 360
```

<210> SEQ ID NO 18
<211> LENGTH: 1899
<212> TYPE: DNA
<213> ORGANISM: Mouse

<400> SEQUENCE: 18

```
gctgggagac ccaggaagct ccagacttag catggagcac ggactcagga gcatcccagc    60
ctggacgctg gacaagttca tagaggatta cctccttccc gacaccacct ttggtgctga   120
tgtcaaatca gccgtcaatg tcgtgtgtga tttcctgaag gagagatgct tccaaggtgc   180
tgcccaccca gtgagggtct ccaaggtggt gaaggtggcc tcctcaggca aaggcaccac   240
actcaagggc aagtcagacg ctgacctggt ggtgttcctt aacaatctca ccagctttga   300
ggatcagtta aaccgacggg gagagttcat caaggaaatt aagaaacagc tgtacgaggt   360
tcagcatgag agacgtttta gagtcaagtt tgaggtccag agttcatggt ggcccaacgc   420
ccggtctctg agcttcaagc tgagcgcccc ccatctgcat caggaggtgg agtttgatgt   480
gctgccagcc tttgatgtcc tgggtcatgt taatacttcc agcaagcctg atcccagaat   540
ctatgccatc ctcatcgagg aatgtacctc cctggggaag gatggcgagt ctctacctg    600 cttcacggag ctccagcgga acttcctgaa gcagcgccca accaagctga agagtctcat   660
ccgcctggtc aagcactggt accaactgtg taaggagaag ctggggaagc cattgcctcc   720
acagtacgcc ctagagttgc tcactgtctt tgcctgggaa caagggaatg gatgttatga   780
gttcaacaca gcccagggct tccggaccgt cttggaactg gtcatcaatt atcagcatct   840
tcgaatctac tggacaaagt attatgactt tcaacaccag gaggtctcca atacctgca    900 cagacagctc agaaaagcca ggcctgtgat cctggaccca gctgacccaa cagggaatgt   960
ggccggtggg aacccagagg gctggaggcg gttggctgaa gaggctgatg tgtgggtatg  1020
gtacccatgt tttattaaaa aggatggttc ccgagtgagc tcctgggatg tgccgacggt  1080
ggttcctgta ccttttgagc aggtagaaga gaactggaca tgtatcctgc tgtgagcaca  1140
gcagcacctg cccaggagac tgctggtcag gggcatttgc tgctctgctg caggcccatg  1200
acccagtgag ggagggcccc acctggcatc agactccgtg cttctgatgc ctgccagcca  1260
tgtttgactc ctgtccaatc acagccagcc ttcctcaaca gattcagaag gagaggaaag  1320
aacacacgct tggtgtccat ctgtccacct gttggaaggt tctgtctgac aaagtctgat  1380
caacaataaa ccacagcagg tgccgtcatg gtgtgtgaac tctgaggagt gggccataca  1440
agaacagtgc aggtgtgtga gcgtgtgtgt gcccatgcac atgcgtgtgt gtcttcacgg  1500
ttcaactaga tgcatttagt gagcacttac tacatatgct acatgattca gatgttcagc  1560
agtggttaga gcaaagccta actgctaggc ttttgatgc aagttggatt gggatccttc   1620
caggtctctt cttatacata cacacaagag aggaaccctt ggttttttt gcccatgacc   1680 ccaagacaag attctagccc tgccctatct gacacattag cggttctctg ctacacatg   1740 gacatggaac actgagattg tggcctgtgc tctcagggtg cccttgagtg gctacaacat  1800
gcaggctggg ggaccataga tatgatgaaa ataaaaggta cctggaattt ttgacacatg  1860
taactttgaa aaaaaaaaa aaaaaaaaa aaaaaaaa                             1899
```

<210> SEQ ID NO 19
<211> LENGTH: 1944
<212> TYPE: DNA
<213> ORGANISM: Mouse

<400> SEQUENCE: 19

```
gccagcctag gagacacagg aacctgctgg tgcagaggta aaagctggac ctaggatgga    60
gcaggatctg aggagcatcc cggcctcgaa gcttgataag ttcatagaga atcatctccc   120
ggacaccagc ttctgtgctg acctcagaga agtcatagat gccctgtgtg ctctcctgaa   180
ggacagattc ttccggggcc ccgtccgccg aatgagggcc tctaaggggg tcaagggcaa   240
```

-continued

```
atgcaccgcg ctcaagggca ggtcagacgc tgacctggtg gtgttcctta acaatctcac      300
ctactttgag gatcaattaa accaacaggg agtgttgatt aaggaaatta agaaacagct      360
gtacgaggtt cagcatgaga gacgttttgg agtcaagttt gaggtccaga gtttaaggag      420
tcccaactcc cgggctctga gcttcaagct gagcgccccc gacctgctga aggaggtgaa      480
gtttgacgtg ctgccagcct atgatttact ggatcatctt aacatcctca agaagcctaa      540
ccaacaattc tacgccaatc tcatcagtgg gcgtaccccg ctggggaagg agggcaagtt      600
attgacctgc tttatggggc ttcggaagta cttcctgaac tgtcgcccaa ccaagctgaa      660
gcgcctcatc cacctggtca cgcactggta ccaactgtgt aaggagaagc tgggggaccc      720
gctgccccca cagtatgccc tggagctgct cacagtctat gcctgggagt atgggagtcg      780
agtaactaaa ttcaacacag cccagggctt ccgaaccgtc ttggaactgg ttaccaagta      840
caaacagctt cgaatctact ggacagtgta ttatgacttt cgacatcaag aggtctctga      900
atacctgcac caacagctca aaaagacag gcctgtgatc ttggaccccg ctgatccaac      960
aaggaatata gctggttttga acccaaagga ctggcggcgt ctagcaggag aggctgccgc     1020
ctggctgcaa tacccatgct ttaagtacag ggacggttcc ccagtgtgct cctgggaggt     1080
gccgacggag gttgcagtgc caacgaagta tctcttttgt cgtatttcct ggttattgtt     1140
ttggtctttg tttcatttca tctttgggaa gacttcatct ggatagccca gagtgtcttg     1200
gatattgcca tcctcctgcc ttagcgctgg catgactgca gcgtaggcct gttatgccct     1260
gcctcccctc catcctcaag tggacaagaa ctgggcatgt gttttcctgt gagcccagtg     1320
ggacctgtcc aggatgctcc agagtcagac gcatgtcctg ctctgctgca gggccttgac     1380
ccagagaaga caggaaggtg cccaaagccc aagagaggga ggttccaacc tgtgatcaga     1440
ctccaggctt ctgtcccctg ccctcaaccc ctgcacagac agcctttctc acagcctgct     1500
ttatctgtct tgtcccccaa caatgttctc tgggagacaa gagattcaga aggagaatat     1560
gatggtttgt atatggttgg cccagggaat ggcactgtta ggaggtgtgg ccatgttgga     1620
gtgggtgtgg ccttgtgtgt gtgggcttct ctcttgtctt agctgcctgg aagtcagtat     1680
gctgctagca gccttcagat gaagatgtag aactctcagc tcctcctgca ccatgcctgc     1740
ctggacgttg ccatgctctt gccttggtga atggactg aacttctgaa cctgtaagcc      1800
aactccaatt aaatgttgtt tttataaaaa aaaacaaaa aaaaaaaaa aaaaaaaaa       1860
aaaaaaaaaa aaaaaaaaaa aaaaaaaaaa aaaaaaaaaa aaaaaaaaaa aaaaaaaaaa     1920
aaaaaaaaaa aaaaaaaaaa aaaa                                            1944
```

```
<210> SEQ ID NO 20
<211> LENGTH: 1916
<212> TYPE: DNA
<213> ORGANISM: Mouse

<400> SEQUENCE: 20
```

```
tggacaagtt catagaggat tacctccttc ccgacaccac ctttggtgct gatgtcaaat       60
cagccgtcaa tgtcgtgtgt gatttcctga aggagagatg cttccaaggt gctgcccacc      120
cagtgagggt ctccaaggtg gtgaagggtg gctcctcagg caaaggcacc acactcaagg      180
gcaagtcaga cgctgacctg gtggtcttcc ttaacaatct caccagcttt gaggatcagt      240
taaaccgacg gggagagttc atcaaggaaa ttaagaaaca gctgtacgag gttcagcatg      300
agagacgttt tagagtcaag tttgaggtcc agagttcatg gtgcccaac gcccggtctc      360
```

```
tgagcttcaa gctgagcgcc ccccatctgc atcaggaggt ggagtttgat gtgcttccag      420
cctttgatgt cctgggtcat ggtagtatca ataagaagcc taatcccctta atctacacca     480 tcctcatctg ggaatgtacc tccctgggga aggatggcga gttctctacc tgcttcacgg      540
agctccagcg gaacttcctg aagcagcgcc caaccaagct gaagagtctc atccgcctgg      600
tcaaacactg gtaccaactg tgtaaggaga agctggggaa gccactgccc ccacagtatg      660
ccctggagct actcactgtc tatgcctggg aacagggaa tggatgtaat gagttcaaca      720
cagcccaggg cttccggacc gtcttggaac tggtcatcaa ttatcagcat cttcgaatct     780
actggacaaa gtattatgac tttcaacaca aggaggtctc caaatacctg cacagacagc     840
tcagaaaagc caggcctgtg atcctggacc cagctgaccc gacagggaat gtggctggtg     900
ggaacccaga gggctggagg cggttggctg aagaggctga tgtgtggctg tggtacccat     960
gttttatgaa aaatgatggt tcccgagtga gctcctggga tgtgccgacg gtggttcctg    1020 tacctttga gcaggtggag gagaactgga catgtatcct gctgtgagca cagcagcacc    1080
tgcccaggag actgctggtc aggggcattt gctgctctgc tgcaggccca tgacccagtg    1140
aggcagggcc ccacctggca tcagactccg tgcttctgat gcctgccagc catgtttgac    1200
tcctgtccaa tcacagccag ccttcctcaa cagattcaga aggagaggaa agaacacacg    1260
cttggtgtcc atctgtccac ctgttggaag gttctgtctg acaaagtctg atcaacaata    1320
aaccacagca ggtgcccgtc atggtgtgtg aactctgcag gagtgggcca tacaagaaca    1380
gtgcaggtgt gtgagcgtgt gtgtgcccat gacatgcgtg tgtgtcttca cggttcaact    1440
agatgcattt agtgagcact tactacatat gctacatgat tcagatgttc agcagtggtt    1500
agagcaaagc ctaactgcta ggcttttga tgcaagttgg attgggatcc ttccaggtct    1560
cttcttacac atacacacaa gagaggaccc ttggtttctt ctgcccatga cccaagacag    1620
attctagccc tgccctatga cacagaaact attccctgcc acacatggac atgaacactg    1680
agactgtggc ctgtgctctc aggtgccctt gagtggcatc aacatgcagg ctgggggccc    1740
ataggtatga tgaaaataaa aggtacctgg aattttgaca catgtaactt tgaaacaggg    1800
tcattggtag caacgatcag ctttatcaca tttagttaaa tcacaatgat tgtggtttcc    1860
tttctgagac atgaatttgt gtgacacacg ctgtcgtgga actcacagga aaaaaa       1916
```

<210> SEQ ID NO 21
<211> LENGTH: 3064
<212> TYPE: DNA
<213> ORGANISM: Mouse

<400> SEQUENCE: 21

```
ccgctcactg aagataacta gacagaaaac gtcgtgagac tacctcacgc tgtccattga      60
ccaggagcaa tcctttgtgc ctcacatctt tgggactgcg gtaggcatca gagaaatgtc     120
acctcgatgg gccctgcagc tggagagtct gaccctggat atggccttca gctaagacac     180
ctgcacagat gatgagcagc ctcggggaga ctagctgagg tcggtagtta ggaatgtgga    240
gtgtggatgt tgtgaccctc agcataagca ggaataacct agcctaaccc tatcgctcga    300
gacgccacta gtaacggaga cactatgcgt gattaagaat gaaataaatg catttgccac    360
tgccagatca ccaggcagat gagattatgt ggcggaattg ctgaatctta ctctgttgtg    420
gtaaacaaca tcctgtgctc acaacagagc cggtggggag actgcatcct taactcctgt    480
tcccttctgc cttgaagaag gtaaactgga tctccctgca gtttcacttt caattcttgt    540
caaagcttgg tttctgtttc cagtttctcc aaggagggag gggcagagcg cttttcttct    600
```

-continued

| | | | | |
|---|---|---|---|---|
| ttccatgcaa | ctctccatcc | cattgtctcc | tccagagaac gctgcaggaa | gcttctccca | 660 |
| tcagagctga | gcagaagctc | agaggattta | tctagaggac aggctggccc | agctgaaatg | 720 |
| gacccgttcc | ccgacctgta | tgcgacccct | ggggacagtc tagaccactt | cctggaacac | 780 |
| agccttcagc | cccagaggga | ctggaaagag | gaagggcagg atgcctggga | gagaatcgag | 840 |
| aggttctttc | gggaacagtg | cttccgtgat | gagctgctcc tggaccaaga | agtcagggtg | 900 |
| attaaggtgg | tgaagggagg | ctcctcggga | aaggggacaa ccctgaacca | cagatctgac | 960 |
| caagacatga | ttctgttctt | aagctgcttt | tccagtttcg aagagcaggc | gagaaaccgg | 1020 |
| gaggtcgtca | tcagcttcat | taagaagagg | ctgattcatt gtagcagaag | cctggcctac | 1080 |
| aacatcattg | tccttaccca | cagagagggc | aaaagggccc ctcgctccct | caccctaaag | 1140 |
| gttcagtccc | ggaagactga | tgacattatt | tggatggata tcctcccagc | ttacgatgct | 1200 |
| ttgggaccta | tttccagaga | ctcaaaacca | gcaccggcaa tctacgagac | tctgataaga | 1260 |
| agtaagggct | accctggtga | cttctcacca | agcttcacag agttacagag | acattttgtg | 1320 |
| aaaactcgcc | cagttaaact | gaagaacctc | ctccggttgg tgaagttctg | gtacctgcag | 1380 |
| tgcctgagac | gtaaatatgg | aagaggtgca | gtgttgccct caaaatatgc | tctggagctg | 1440 |
| ctgaccatct | acgcctggga | gatgggtaca | gagagcagtg atagcttcaa | tctggatgaa | 1500 |
| gggttcgtag | ccgtgatgga | gctcctcgta | aactaccgcg acatctgcat | ctactggacc | 1560 |
| aagtactaca | atttccaaaa | cgaggtcgtc | aggaactttc tgaagaaaca | gctgaaggga | 1620 |
| gaccggccca | tcatcctaga | cccagctgac | cccaccaaca acctgggaag | aagaaaggga | 1680 |
| tgggaacagg | tggctgcaga | agctgctttc | tgcctgctgc aggtctgttg | cacgactgta | 1740 |
| ggccccagcg | agcgctggaa | tgtacagcga | gcgagggatg ttcaggtgag | agtgaaacaa | 1800 |
| acgggaacag | tggattggac | actctggaca | aaccccctaca gcccatcag | aaagatgaag | 1860 |
| gcagagatca | ggagggaaaa | gaactttgga | ggggaactgc gcatctcctt | ccaggagccc | 1920 |
| ggagggggaga | gacagctgct | cagcagcagg | aagaccctag cagattatgg | gatattctct | 1980 |
| aaggtgaaca | ttcaagtgct | ggagacccttt | cctcctgaga tcctggtctt | tgtgaagtat | 2040 |
| cctggtggcc | agagcaagcc | tttcaccatc | gaccctgatg ataccatctt | agatctgaaa | 2100 |
| gagaagatag | aagatgctgg | agctggaggc | cttacgtagg cccttgtgcg | gaggatcagg | 2160 |
| tactactgtt | ggatgaggta | atcgactagt | ctggctgctt gagtccgtgc | ctagagtctt | 2220 |
| acgcctccct | acctctaccc | tagactctga | tgggttcttt ctatagctta | aatatcaaca | 2280 |
| ttcccttctc | ttgcttaaac | cctctcctat | cagccgggcg tggtggtgca | tgcctttagc | 2340 |
| tcagcactta | gagaatttct | gagttcaagg | ccagcctggt ctatagagtg | agttacagaa | 2400 |
| cagccagagc | tatacggaga | aaccctgtct | cagataaaca aacaaacaaa | caaacaaacc | 2460 |
| ctctcctgtg | ttttccaata | atacagaatg | aagttcaagt ttcttttcct | aacagtcaat | 2520 |
| taagctgaac | cctgcttagt | ccccgacccc | caactctaaa cactcaactc | atactgaatg | 2580 |
| cagagtgaca | ccttgagtca | cactgagagc | tgagtcacac ctgtgtctct | ttcctcaaca | 2640 |
| tccttccctc | agcctctgtt | tttcattcat | ttctgttgag tcaccgaatc | ttcaaagagc | 2700 |
| agacccccaga | ctgttcagat | tccccacctt | cttccagaaa ccttcttaga | attggaaaac | 2760 |
| ttaacccaat | tccagacatt | tcaccgagac | tcagcggtcc tggacttaac | aagcctttca | 2820 |
| catcattctt | gcatgctcct | gtttgaaaac | aactactatc tggcccatgc | agcaggccaa | 2880 |
| atcatcttgt | gttccctccc | tctcccttca | tcctgttagc tcccgtggcg | taaatctatc | 2940 |

<210> SEQ ID NO 22
<211> LENGTH: 1940
<212> TYPE: DNA
<213> ORGANISM: Mouse

<400> SEQUENCE: 22

```
aaacactcct ggcctcagga tggagaatgg tctctgcagc atccaagcca gggagctgga      60
cgagttcata tgtgattacc tctttcctga caccaccttc cttactgagc tcagagcaga     120
catcgactcc ataagtgctt tcctgaagga gagatgcttc caaggtgccg cccatcctgt     180
gagggtctcc agggttgtga tgggcggctc ctatgatgaa cacactgcac tcaagggcaa     240
gtcagaggcc aaaatggtgt tgttctttaa caatctcacc agctttgagg agcagttaaa     300
gcgacgggga gagttcgttg aggaaattca gaaacacctg tgtcagctgc agcaagagaa     360
accatttaaa gtgaagtttg aggtgcagag ctcagaggag cccaactcca ggtctctgag     420
cttcaagctg agctcccccg agctccagca ggaggtggaa tttgatgtgc agccagccta     480
tgatgtccta tatgaactga gaaacaaacac gtatgctgaa ccccaattct acaacaaagt     540
ctacgcccaa ctcatccatg agtgcaccac cctggagaag gagggcgatt tctccatctg     600
cttcaccgac ctccatcaga acttcatgag gtatcgtgcg cccaagctct ggaacctcat     660
ccgtctggtc aagcactggt atcaactgtg taaggagaag ctgagggagc cgctgccccc     720
acagtacgcc ctggagctgc tcactgtcta tgtatgggaa cattcgaata aaaatcaaga     780
aaaagtaacc acagccaaga acttccggac cttcttagaa ctggtcgcct attacaagaa     840
tcttcgaatc tactggacat ggtattatga cttccgacat caagaggtct gtgcctacct     900
gtgcagacag ctcaaaaaag ccaggcctct gatcctggat ccagcagacc caacaaggaa     960
cgtggctggt tcagacttac aggcatggga cctgctggca aaggaggctc agacctggat    1020
gcagtcctct tgctttagaa actgtgatat gtcctttgtg cccacctggg atttgtcgcc    1080
agagagacaa gaatgtgcct tccagtgagc agtgcagcgc ttgctctgaa ggctccagag    1140
tcagggcat accttcctct gctgcaagac cttgacctag agaggacagg atggcactca    1200
aggctccagt gaggggcatc cagcctgtga tcagactcca ggcttctgat ccctgactgc    1260
ccatggatag ccttcctcac aggctgcttc atctgcctta gcttccaaca gtgttctctg    1320
ggagtcagac tgtgatggac agagaagaac gcaagctcga cttccatctg tccacctgtt    1380
gggaggttct gtccaacagt ggctgattgt catcaacaaa ccacagcaag ccatggggga    1440
gggtgcactc tgagagaagg aacctttaag tacacttgtg tgtctgtgtg tttaaggatg    1500
tggtgtgtcc atatgcaact agaaaccttg agcacgtgtt acaagctcca catgggccca    1560
ggtaattgcc agaaagggt ggacagagaa aaaccaaact gttacacgta ttgatgttgg    1620
gtagcttggg atccttctag atctctgatg caagaaaccc agactagaat ccatggctcc    1680
tgctgtccat tctcctgtga caaaatttta ggccttcccc atcccacaca gaaactgttc    1740
tccaaccaca catgaccctg gagccctggg aatctggcca gcgtgcatcg tggtgcactg    1800
attctgcagc atgcaggctg aggtccacag cagtgtggga aactatgtgc aatttgtgac    1860
cagtgatgac ttgaaagctt agctgtctgt gtgagggtga gatttgaagc actgaattaa    1920
atcacaatgc actggggctg                                                1940
```

<210> SEQ ID NO 23
<211> LENGTH: 1385
<212> TYPE: DNA
<213> ORGANISM: human

<400> SEQUENCE: 23

```
ggcacgaggc tcagtcagca gaagagataa aagcaaacag gtctgggagg cagttctgtt    60
gccactctct ctcctgtcaa tgatggatct cagaaatacc ccagccaaat ctctggacaa   120
gttcattgaa gactatctct tgccagacac gtgtttccgc atgcaaatca accatgccat   180
tgacatcatc tgtgggttcc tgaaggaaag gtgcttccga ggtagctcct accctgtgtg   240
tgtgtccaag gtggtaaagg gtggctcctc aggcaagggc accaccctca gaggccgatc   300
tgacgctgac ctggttgtct tcctcagtcc tctcaccact tttcaggatc agttaaatcg   360
ccggggagag ttcatccagg aaattaggag acagctggaa gcctgtcaaa gagagagagc   420
attttccgtg aagtttgagg tccaggctcc acgctgggc aacccccgtg cgctcagctt   480
cgtactgagt tcgctccagc tcggggaggg ggtggagttc gatgtgctgc ctgcctttga   540
tgccctgggt cagttgactg gcagctataa acctaaccc caaatctatg tcaagctcat   600
cgaggagtgc accgacctgc agaaagaggg cgagttctcc acctgcttca gaactaca   660
gagagacttc ctgaagcagc gccccaccaa gctcaagagc ctcatccgcc tagtcaagca   720
ctggtaccaa aattgtaaga gaagcttgg gaagctgcca cctcagtatg ccctggagct   780
cctgacggtc tatgcttggg agcgaggag catgaaaaca catttcaaca cagcccaggg   840
atttcggacg gtcttggaat tagtcataaa ctaccagcaa ctctgcatct actggacaaa   900
gtattatgac tttaaaaacc ccattattga aagtacctg agaaggcagc tcacgaaacc   960
caggcctgtg atcctggacc cggcggaccc tacaggaaac ttgggtggtg gagacccaaa  1020
gggttggagg cagctggcac aagaggctga ggcctggctg aattaccat gctttaagaa  1080
ttgggatggg tccccagtga gctcctggat tctgctggtg agacctcctg cttcctccct  1140
gccattcatc cctgccctc tccatgaagc ttgagacata tagctggaga ccattctttc  1200
caaagaactt acctcttgcc aaaggccatt tatattcata tagtgacagg ctgtgctcca  1260
tattttacag tcattttggt cacaatcgag ggtttctgga attttcacat cccttgtcca  1320
gaattcattc ccctaagagt aataataaat aatctctaac accaaaaaaa aaaaaaaaa  1380
aaaaa                                                              1385
```

<210> SEQ ID NO 24
<211> LENGTH: 364
<212> TYPE: PRT
<213> ORGANISM: human

<400> SEQUENCE: 24

```
Met Met Asp Leu Arg Asn Thr Pro Ala Lys Ser Leu Asp Lys Phe Ile
 1               5                  10                  15
Glu Asp Tyr Leu Leu Pro Asp Thr Cys Phe Arg Met Gln Ile Asn His
            20                  25                  30
Ala Ile Asp Ile Ile Cys Gly Phe Leu Lys Glu Arg Cys Phe Arg Gly
        35                  40                  45
Ser Ser Tyr Pro Val Cys Val Ser Lys Val Val Lys Gly Gly Ser Ser
    50                  55                  60
Gly Lys Gly Thr Thr Leu Arg Gly Arg Ser Asp Ala Asp Leu Val Val
65                  70                  75                  80
```

```
Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Phe Ser Val Lys Phe Glu Val Gln Ala Pro Arg Trp Gly Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Ser Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335

Gly Ser Pro Val Ser Ser Trp Ile Leu Leu Val Arg Pro Pro Ala Ser
            340                 345                 350

Ser Leu Pro Phe Ile Pro Ala Pro Leu His Glu Ala
        355                 360

<210> SEQ ID NO 25
<211> LENGTH: 2911
<212> TYPE: DNA
<213> ORGANISM: human

<400> SEQUENCE: 25
cggcagccag ctgagagcaa tgggaaatgg ggagtcccag ctgtcctcgg tgcctgctca      60
gaagctgggt tggtttatcc aggaatacct gaagccctac gaagaatgtc agacactgat     120
cgacgagatg gtgaacacca tctgtgacgt cctgcaggaa cccgaacagt tccccctggt     180
gcagggagtg gccataggtg gctcctatgg acggaaaaca gtcttaagag caactccga      240
tggtacccct tgtcctcttc tcagtgactt aaaacaattc caggatcaga agagaagcca     300
acgtgacatc ctcgataaaa ctggggataa gctgaagttc tgtctgttca cgaagtggtt     360
gaaaaacaat ttcgagatcc agaagtccct tgatgggttc accatccagg tgttcacaaa     420
aaatcagaga atctctttcg aggtgctggc cgccttcaac gctctgagct taaatgataa     480
```

-continued

| | |
|---|---|
| tcccagcccc tggatctatc gagagctcaa aagatccttg gataagacaa atgccagtcc | 540 |
| tggtgagttt gcagtctgct tcactgaact ccagcagaag ttttttgaca accgtcctgg | 600 |
| aaaactaaag gatttgatcc tcttgataaa gcactggcat caacagtgcc agaaaaaaat | 660 |
| caaggattta ccctcgctgt ctccgtatgc cctggagctg cttacggtgt atgcctggga | 720 |
| acagggtgc agaaaagaca actttgacat tgctgaaggc gtcagaaccg tactggagct | 780 |
| gatcaaatgc aggagaagc tgtgtatcta ttggatggtc aactacaact ttgaagatga | 840 |
| gaccatcagg aacatcctgc tgcaccagct ccaatcagcg aggccagtaa tcttggatcc | 900 |
| agttgaccca accaataatg tgagtggaga taaaatatgc tggcaatggc tgaaaaaaga | 960 |
| agctcaaacc tggttgactt ctcccaacct ggataatgag ttacctgcac catcttggaa | 1020 |
| tgttctgcct gcaccactct tcacgacccc aggccacctt ctggataagt tcatcaagga | 1080 |
| gtttctccag cccaacaaat gcttcctaga gcagattgac agtgctgtta acatcatccg | 1140 |
| tacattcctt aaagaaaact gcttccgaca atcaacagcc aagatccaga ttgtccgggg | 1200 |
| aggatcaacc gccaaaggca cagctctgaa gactggctct gatgccgatc tcgtcgtgtt | 1260 |
| ccataactca cttaaaagct acacctccca aaaaacgag cggcacaaaa tcgtcaagga | 1320 |
| aatccatgaa cagctgaaag cctttggag ggagaaggag gaggagcttg aagtcagctt | 1380 |
| tgagcctccc aagtggaagg ctcccagggt gctgagcttc tctctgaaat ccaaagtcct | 1440 |
| caacgaaagt gtcagctttg atgtgcttcc tgcctttaat gcactgggtc agctgagttc | 1500 |
| tggctccaca cccagcccg aggtttatgc agggctcatt gatctgtata atcctcgga | 1560 |
| cctcccggga ggagagttt ctacctgttt cacagtcctg cagcgaaact tcattcgctc | 1620 |
| ccggcccacc aaactaaagg atttaattcg cctggtgaag cactggtaca agagtgtga | 1680 |
| aaggaaactg aagccaaagg ggtctttgcc cccaaagtat gccttggagc tgctcaccat | 1740 |
| ctatgcctgg gagcagggga gtggagtgcc ggattttgac actgcagaag gtttccggac | 1800 |
| agtcctggag ctggtcacac aatatcagca gctctgcatc ttctggaagg tcaattacaa | 1860 |
| ctttgaagat gagaccgtga ggaagttct actgagccag ttgcagaaaa ccaggcctgt | 1920 |
| gatcttggac ccagccgaac ccacaggtga cgtgggtgga ggggaccgtt ggtgttggca | 1980 |
| tcttctggca aaagaagcaa aggaatggtt atcctctccc tgcttcaagg atgggactgg | 2040 |
| aaacccaata ccaccttgga agtgccgac aatgcagaca ccaggaagtt gtggagctag | 2100 |
| gatccatcct attgtcaatg agatgttctc atccagaagc catagaatcc tgaataataa | 2160 |
| ttctaaaaga aacttctaga gatcatctgg caatcgcttt taaagactcg gctcaccgtg | 2220 |
| agaaagagtc actcacatcc attcttccct tgatggtccc tattcctcct tcccttgctt | 2280 |
| cttggacttc ttgaaatcaa tcaagactgc aaacccttc ataaagtctt gccttgctga | 2340 |
| actccctctc tgcaggcagc ctgccttaa aaatagttgc tgtcatccac tttatgtgca | 2400 |
| tcttatttct gtcaacttgt atttttttc ttgtattttt ccaattagct cctccttttt | 2460 |
| ccttccagtc taaaaagga atcctctgtg tcttcaaagc aaagctcttt actttcccct | 2520 |
| tggttctcat aactctgtga tcttgctctc ggtgcttcca actcatccac gtcctgtctg | 2580 |
| tttcctctgt atacaaaacc ctttctgccc ctgctgacac agacatcctc tatgccagca | 2640 |
| gccagccaac ccttcattta gaacttcaag ctctccaaag gctcagatta taactgttgt | 2700 |
| catatttata tgaggctgtt gtcttttcct tctgagcctg cctttctccc ccccacccag | 2760 |
| gagtatcctc ttgccaaatc aaaagacttt tccttgggc tttagcctta aagatacttg | 2820 |
| aaggtctagg tgctttaacc tcacataccc tcacttaaac ttttatcact gttgcatata | 2880 |

-continued ccagttgtga tacaataaag aatgtatctg g                                          2911

<210> SEQ ID NO 26
<211> LENGTH: 719
<212> TYPE: PRT
<213> ORGANISM: human

<400> SEQUENCE: 26

Met Gly Asn Gly Glu Ser Gln Leu Ser Ser Val Pro Ala Gln Lys Leu
1               5                   10                  15

Gly Trp Phe Ile Gln Glu Tyr Leu Lys Pro Tyr Glu Glu Cys Gln Thr
            20                  25                  30

Leu Ile Asp Glu Met Val Asn Thr Ile Cys Asp Val Leu Gln Glu Pro
        35                  40                  45

Glu Gln Phe Pro Leu Val Gln Gly Val Ala Ile Gly Gly Ser Tyr Gly
    50                  55                  60

Arg Lys Thr Val Leu Arg Gly Asn Ser Asp Gly Thr Leu Val Leu Phe
65                  70                  75                  80

Phe Ser Asp Leu Lys Gln Phe Gln Asp Gln Lys Arg Ser Gln Arg Asp
                85                  90                  95

Ile Leu Asp Lys Thr Gly Asp Lys Leu Lys Phe Cys Leu Phe Thr Lys
            100                 105                 110

Trp Leu Lys Asn Asn Phe Glu Ile Gln Lys Ser Leu Asp Gly Phe Thr
        115                 120                 125

Ile Gln Val Phe Thr Lys Asn Gln Arg Ile Ser Phe Glu Val Leu Ala
    130                 135                 140

Ala Phe Asn Ala Leu Ser Leu Asn Asp Asn Pro Ser Pro Trp Ile Tyr
145                 150                 155                 160

Arg Glu Leu Lys Arg Ser Leu Asp Lys Thr Asn Ala Ser Pro Gly Glu
                165                 170                 175

Phe Ala Val Cys Phe Thr Glu Leu Gln Gln Lys Phe Phe Asp Asn Arg
            180                 185                 190

Pro Gly Lys Leu Lys Asp Leu Ile Leu Leu Ile Lys His Trp His Gln
        195                 200                 205

Gln Cys Gln Lys Lys Ile Lys Asp Leu Pro Ser Leu Ser Pro Tyr Ala
    210                 215                 220

Leu Glu Leu Leu Thr Val Tyr Ala Trp Glu Gln Gly Cys Arg Lys Asp
225                 230                 235                 240

Asn Phe Asp Ile Ala Glu Gly Val Arg Thr Val Leu Glu Leu Ile Lys
                245                 250                 255

Cys Gln Glu Lys Leu Cys Ile Tyr Trp Met Val Asn Tyr Asn Phe Glu
            260                 265                 270

Asp Glu Thr Ile Arg Asn Ile Leu Leu His Gln Leu Gln Ser Ala Arg
        275                 280                 285

Pro Val Ile Leu Asp Pro Val Asp Pro Thr Asn Asn Val Ser Gly Asp
    290                 295                 300

Lys Ile Cys Trp Gln Trp Leu Lys Lys Glu Ala Gln Thr Trp Leu Thr
305                 310                 315                 320

Ser Pro Asn Leu Asp Asn Glu Leu Pro Ala Pro Ser Trp Asn Val Leu
                325                 330                 335

Pro Ala Pro Leu Phe Thr Thr Pro Gly His Leu Leu Asp Lys Phe Ile
            340                 345                 350

Lys Glu Phe Leu Gln Pro Asn Lys Cys Phe Leu Glu Gln Ile Asp Ser
        355                 360                 365

```
Ala Val Asn Ile Ile Arg Thr Phe Leu Lys Glu Asn Cys Phe Arg Gln
        370                 375                 380

Ser Thr Ala Lys Ile Gln Ile Val Arg Gly Gly Ser Thr Ala Lys Gly
385                 390                 395                 400

Thr Ala Leu Lys Thr Gly Ser Asp Ala Asp Leu Val Val Phe His Asn
                405                 410                 415

Ser Leu Lys Ser Tyr Thr Ser Gln Lys Asn Glu Arg His Lys Ile Val
                420                 425                 430

Lys Glu Ile His Glu Gln Leu Lys Ala Phe Trp Arg Glu Lys Glu Glu
                435                 440                 445

Glu Leu Glu Val Ser Phe Glu Pro Pro Lys Trp Lys Ala Pro Arg Val
        450                 455                 460

Leu Ser Phe Ser Leu Lys Ser Lys Val Leu Asn Glu Ser Val Ser Phe
465                 470                 475                 480

Asp Val Leu Pro Ala Phe Asn Ala Leu Gly Gln Leu Ser Ser Gly Ser
                485                 490                 495

Thr Pro Ser Pro Glu Val Tyr Ala Gly Leu Ile Asp Leu Tyr Lys Ser
                500                 505                 510

Ser Asp Leu Pro Gly Gly Glu Phe Ser Thr Cys Phe Thr Val Leu Gln
                515                 520                 525

Arg Asn Phe Ile Arg Ser Arg Pro Thr Lys Leu Lys Asp Leu Ile Arg
530                 535                 540

Leu Val Lys His Trp Tyr Lys Glu Cys Glu Arg Lys Leu Lys Pro Lys
545                 550                 555                 560

Gly Ser Leu Pro Pro Lys Tyr Ala Leu Glu Leu Leu Thr Ile Tyr Ala
                565                 570                 575

Trp Glu Gln Gly Ser Gly Val Pro Asp Phe Asp Thr Ala Glu Gly Phe
                580                 585                 590

Arg Thr Val Leu Glu Leu Val Thr Gln Tyr Gln Gln Leu Cys Ile Phe
        595                 600                 605

Trp Lys Val Asn Tyr Asn Phe Glu Asp Glu Thr Val Arg Lys Phe Leu
        610                 615                 620

Leu Ser Gln Leu Gln Lys Thr Arg Pro Val Ile Leu Asp Pro Ala Glu
625                 630                 635                 640

Pro Thr Gly Asp Val Gly Gly Asp Arg Trp Cys Trp His Leu Leu
                645                 650                 655

Ala Lys Glu Ala Lys Glu Trp Leu Ser Ser Pro Cys Phe Lys Asp Gly
                660                 665                 670

Thr Gly Asn Pro Ile Pro Pro Trp Lys Val Pro Thr Met Gln Thr Pro
                675                 680                 685

Gly Ser Cys Gly Ala Arg Ile His Pro Ile Val Asn Glu Met Phe Ser
        690                 695                 700

Ser Arg Ser His Arg Ile Leu Asn Asn Asn Ser Lys Arg Asn Phe
705                 710                 715

<210> SEQ ID NO 27
<211> LENGTH: 6262
<212> TYPE: DNA
<213> ORGANISM: human

<400> SEQUENCE: 27
gccctgcttc cccttgcacc tgcgccgggc ggccatggac ttgtacagca ccccggccgc      60
tgcgctggac aggttcgtgg ccagaaggct gcagccgcgg aaggagttcg tagagaaggc     120
```

-continued

| | |
|---|---|
| gcggcgcgct ctgggcgccc tggccgctgc cctgagggag cgcggggggcc gcctcggtgc | 180 |
| tgctgccccg cgggtgctga aaactgtcaa ggggaggctc ctcgggccgg ggcacagctc | 240 |
| tcaaggtgg ctgtgattct gaacttgtca tcttcctcga ctgcttcaag agctatgtgg | 300 |
| accagagggc ccgccgtgca gagatcctca gtgagatgcg ggcatcgctg gaatcctggt | 360 |
| ggcagaaccc agtccctggt ctgagactca cgtttcctga gcagagcgtg cctggggccc | 420 |
| tgcagttccg cctgacatcc gtagatcttg aggactggat ggatgttagc ctggtgcctg | 480 |
| ccttcaatgt cctgggtcag gccggctccg gcgtcaaacc caagccacaa gtctactcta | 540 |
| ccctcctcaa cagtggctgc aaggggggcg agcatgcggc ctgcttcaca gagctgcgga | 600 |
| ggaactttgt gaacattcgc ccagccaagt tgaagaacct aatcttgctg gtgaagcact | 660 |
| ggtaccacca ggtgtgccta cagggttgt ggaaggagag ctgccccg gtctatgccc | 720 |
| tggaattgct gaccatcttc gcctgggagc agggctgtaa aaggatgct ttcagcctag | 780 |
| ccgaaggcct ccgaactgtc ctgggcctga tccaacagca tcagcacctg tgtgttttct | 840 |
| ggactgtcaa ctatggcttc gaggaccctg cagttgggca gttcttgcag cggcagctta | 900 |
| agagacccag gcctgtgatc ctggacccag ctgaccccac atgggacctg gggaatgggg | 960 |
| cagcctggca ctgggatttg ctagcccagg aggcagcatc ctgctatgac cacccatgct | 1020 |
| ttctgagggg gatgggggac ccagtgcagt cttggaaggg gccggccctt ccacgtgctg | 1080 |
| gatgctcagg tttgggccac cccatccagc tagaccctaa ccagaagacc cctgaaaaca | 1140 |
| gcaagagcct caatgctgtg tacccaagag cagggagcaa acctccctca tgcccagctc | 1200 |
| ctggccccac tggggcagcc agcatcgtcc cctctgtgcc gggaatggcc ttggacctgt | 1260 |
| ctcagatccc caccaaggag ctggaccgct tcatccagga ccacctgaag ccgagccccc | 1320 |
| agttccagga gcaggtgaaa aaggccattg acatcatctt gcgctgcctc catgagaact | 1380 |
| gtgttcacaa ggcctcaaga gtcagtaaag ggggctcatt tggccggggc acagacctaa | 1440 |
| gggatggctg tgatgttgaa ctcatcatct tcctcaactg cttcacggac tacaaggacc | 1500 |
| agggggccccg ccgcgcagag atccttgatg agatgcgagc gcagctagaa tcctggtggc | 1560 |
| aggaccaggt gcccagcctg agccttcagt ttcctgagca gaatgtgcct gaggctctgc | 1620 |
| agttccagct ggtgtccaca gccctgaaga gctggacgga tgttagcctg ctgcctgcct | 1680 |
| tcgatgctgt ggggcagctc agttctggca ccaaaccaaa tccccaggtc tactcgaggc | 1740 |
| tcctcaccag tggctgccag gagggcgagc ataaggcctg cttcgcagag ctgcggagga | 1800 |
| acttcatgaa cattcgccct gtcaagctga gaaacctgat tctgctggtg aagcactggt | 1860 |
| accgccaggt tgcggctcag aacaaaggaa aaggaccagc ccctgcctct ctgcccccag | 1920 |
| cctatgccct ggagctcctc accatctttg cctgggagca gggctgcagg caggattgtt | 1980 |
| tcaacatggc ccaaggcttc cggacggtgc tggggctcgt gcaacagcat cagcagctct | 2040 |
| gtgtctactg gacggtcaac tatagcactg aggacccagc catgagaatg caccttcttg | 2100 |
| gccagcttcg aaaacccaga cccctggtcc tggaccccgc tgatcccacc tggaacgtgg | 2160 |
| gccacggtag ctgggagctg ttggcccagg aagcagcagc gctggggatg caggcctgct | 2220 |
| ttctgagtag agacgggaca tctgtgcagc cctgggatgt gatgccagcc tcctttacc | 2280 |
| aaacccagc tggggacctt gacaagttca tcagtgaatt tctccagccc aaccgccagt | 2340 |
| tcctggccca ggtgaacaag gccgttgata ccatctgttc attttttgaag gaaaactgct | 2400 |
| tccggaattc tcccatcaaa gtgatcaagg tggtcaaggg tggctcttca gccaaaggca | 2460 |
| cagctctgcg aggccgctca gatgccgacc tcgtggtgtt cctcagctgc ttcagccagt | 2520 |

-continued

```
tcactgagca gggcaacaag cgggccgaga tcatctccga gatccgagcc cagctggagg    2580
catgtcaaca ggagcggcag ttcgaggtca gtttgaagt ctccaaatgg gagaatcccc     2640
gcgtgctgag cttctcactg acatcccaga cgatgctgga ccagagtgtg gactttgatg    2700
tgctgccagc ctttgacgcc ctaggccagc tggtctctgg ctccaggccc agctctcaag    2760
tctacgtcga cctcatccac agctacagca atgcgggcga gtactccacc tgcttcacag    2820
agctacaacg ggacttcatc atctctcgcc ctaccaagct gaagagcctg atccggctgg    2880
tgaagcactg gtaccagcag tgtaccaaga tctccaaggg gagaggctcc ctaccccac     2940 agcacgggct ggaactcctg actgtgtatg cctgggagca gggcgggaag gactcccagt    3000
tcaacatggc tgagggcttc cgcacggtcc tggagctggt cacccagtac cgccagctct    3060
gtatctactg gaccatcaac tacaacgcca aggacaagac tgttggagac ttcctgaaac    3120
agcagcttca gaagcccagg cctatcatcc tggatccggc tgacccgaca ggcaacctgg    3180
gccacaatgc ccgctgggac ctgctggcca aggaagctgc agcctgcaca tctgccctgt    3240
gctgcatggg acggaatggc atccccatcc agccatggcc agtgaaggct gctgtgtgaa    3300
gttgagaaaa tcagcggtcc tactggatga agagaagatg gacaccagcc ctcagcatga    3360
ggaaattcag ggtcccctac cagatgagag agattgtgta catgtgtgtg tgagcacatg    3420
tgtgcatgtg tgtgcacacg tgtgcatgtg tgtgttttag tgaatctgct ctcccagctc    3480
acacactccc ctgcctccca tggcttacac actaggatcc agactccatg gtttgacacc    3540
agcctgcgtt tgcagcttct ctgtcacttc catgactcta tcctcatacc accactgctg    3600
cttcccaccc agctgagaat gcccctcct ccctgactcc tctctgccca tgcaaattag    3660
ctcacatctt tcctcctgct gcaatccatc ccttcctccc attggcctct ccttgccaaa    3720
tctaaatagt ttatataggg atggcagaga gttcccatct catctgtcag ccacagtcat    3780
ttggtactgg ctacctggag ccttatcttc tgaagggttt taaagaatgg ccaattagct    3840
gagaagaatt atctaatcaa ttagtgatgt ctgccatgga tgcagtagag gaaagtggtg    3900
gtacaagtgc catgattgat tagcaatgtc tgcactggat acggaaaaaa gaaggtgctt    3960
gcaggtttac agtgtatatg tgggctattg aagagccctc tgagctcggt tgctagcagg    4020
agagcatgcc catattggct tactttgtct gccacagaca cagacagagg gagttgggac    4080
atgcatgcta tggggaccct cttgttggac acctaattgg atgcctcttc atgagaggcc    4140
tccttttctt caccttttat gctgcactcc tcccctagtt tacacatctt gatgctgtgg    4200
ctcagtttgc cttcctgaat tttattggg tccctgtttt ctctcctaac atgctgagat    4260
tctgcatccc cacagcctaa actgagccag tggccaaaca accgtgctca gcctgttct     4320 ctctgccctc tagagcaagg cccaccaggt ccatccagga ggctctcctg acctcaagtc    4380
caacaacagt gtccacacta gtcaaggttc agcccagaaa acagaaagca ctctaggaat    4440
cttaggcaga aagggatttt atctaaatca ctggaaaggc tggaggagca gaaggcagag    4500
gccaccactg gactattggt ttcaatatta gaccactgta gccgaatcag aggccagaga    4560
gcagccactg ctactgctaa tgccaccact accctgcca tcactgcccc acatggacaa    4620
aactggagtc gagacctagg ttagattcct gcaaccacaa acatccatca gggatggcca    4680
gctgccagag ctgcgggaag acggatccca cctccctttc ttagcagaat ctaaattaca    4740
gccagacctc tggctgcaga ggagtctgag acatgtatga ttgaatgggt gccaagtgcc    4800 aggggggcgga gtccccagca gatgcatcct ggccatctgt tgcgtggatg agggagtggg    4860
```

-continued

```
tctatctcag aggaaggaac aggaaacaaa gaaaggaagc cactgaacat cccttctctg      4920
ctccacagga gtgccttaga cagcctgact ctccacaaac cactgttaaa acttacctgc      4980
taggaatgct agattgaatg ggatgggaag agccttccct cattattgtc attcttggag      5040
agaggtgagc aaccaaggga agctcctctg attcacctag aacctgttct ctgccgtctt      5100
tggctcagcc tacagagact agagtaggtg aagggacaga ggacagggct tctaatacct      5160
gtgccatatt gacagcctcc atccctgtcc cccatcttgg tgctgaacca acgctaaggg      5220
caccttctta gactcacctc atcgatactg cctggtaatc caaagctaga actctcagga      5280
ccccaaactc cacctcttgg attggccctg gctgctgcca cacacatatc caagagctca      5340
gggccagttc tggtgggcag cagagacctg ctctgccaag ttgtccagca gcagagtggc      5400
cctggcctgg gcatcacaag ccagtgatgc tcctgggaag accaggtggc aggtcgcagt      5460
tgggtacctt ccattcccac cacacagact ctgggcctcc ccgcaaaatg gctccagaat      5520
tagagtaatt atgagatggt gggaaccaga gcaactcagg tgcatgatac aaggagaggt      5580
tgtcatctgg gtagggcaga gaggagggct tgctcatctg aacagggtg tatttcattc       5640 caggccctca gtctttggca atggccaccc tggtgttggc atattggccc cactgtaact      5700
tttgggggct tcccggtcta gccacaccct cggatggaaa gacttgactg cataaagatg      5760
tcagttctcc ctgagttgat tgataggctt aatggtcacc ctaaaaacac ccacatatgc      5820
ttttcgatgg aaccaggtaa gttgacgcta agttcttat ggaaaaatac acacgcaata       5880
gctaggaaaa cacagggaaa gaagagttct gagcagggcc tagtcttagc caatattaaa      5940
acatactatg aagcctctga tacttaaaca gcatggcgct ggtacgtaaa tagaccaatg      6000
cagttaggtg gctctttcca agactctggg gaaaaaagta gtaaaaagct aaatgcaatc      6060
aatcagcaat tgaaagctaa gtgagagagc cagagggcct ccttggtggt aaaagagggt      6120
tgcatttctt gcagccagaa ggcagagaaa gtgaagacca agtccagaac tgaatcctaa      6180
gaaatgcagg actgcaaaga aattggtgtg tgtgtgtgtg tgtgtgtgtg tgtgtgtgtt      6240
taatttttaa aaagttttta tt                                               6262
```

<210> SEQ ID NO 28
<211> LENGTH: 987
<212> TYPE: PRT
<213> ORGANISM: human

<400> SEQUENCE: 28

```
Met Arg Ala Ser Leu Glu Ser Trp Trp Gln Asn Pro Val Pro Gly Leu
1               5                   10                  15

Arg Leu Thr Phe Pro Glu Gln Ser Val Pro Gly Ala Leu Gln Phe Arg
            20                  25                  30

Leu Thr Ser Val Asp Leu Glu Asp Trp Met Asp Val Ser Leu Val Pro
        35                  40                  45

Ala Phe Asn Val Leu Gly Gln Ala Gly Ser Gly Val Lys Pro Lys Pro
    50                  55                  60

Gln Val Tyr Ser Thr Leu Leu Asn Ser Gly Cys Gln Gly Gly Glu His
65                  70                  75                  80

Ala Ala Cys Phe Thr Glu Leu Arg Arg Asn Phe Val Asn Ile Arg Pro
                85                  90                  95

Ala Lys Leu Lys Asn Leu Ile Leu Leu Val Lys His Trp Tyr His Gln
            100                 105                 110

Val Cys Leu Gln Gly Leu Trp Lys Glu Thr Leu Pro Pro Val Tyr Ala
        115                 120                 125
```

-continued

```
Leu Glu Leu Leu Thr Ile Phe Ala Trp Glu Gln Gly Cys Lys Lys Asp
    130                 135                 140

Ala Phe Ser Leu Ala Glu Gly Leu Arg Thr Val Leu Gly Leu Ile Gln
145                 150                 155                 160

Gln His Gln His Leu Cys Val Phe Trp Thr Val Asn Tyr Gly Phe Glu
                    165                 170                 175

Asp Pro Ala Val Gly Gln Phe Leu Gln Arg Gln Leu Lys Arg Pro Arg
                180                 185                 190

Pro Val Ile Leu Asp Pro Ala Asp Pro Thr Trp Asp Leu Gly Asn Gly
        195                 200                 205

Ala Ala Trp His Trp Asp Leu Leu Ala Gln Glu Ala Ala Ser Cys Tyr
    210                 215                 220

Asp His Pro Cys Phe Leu Arg Gly Met Gly Asp Pro Val Gln Ser Trp
225                 230                 235                 240

Lys Gly Pro Gly Leu Pro Arg Ala Gly Cys Ser Gly Leu Gly His Pro
                245                 250                 255

Ile Gln Leu Asp Pro Asn Gln Lys Thr Pro Glu Asn Ser Lys Ser Leu
                260                 265                 270

Asn Ala Val Tyr Pro Arg Ala Gly Ser Lys Pro Pro Ser Cys Pro Ala
                275                 280                 285

Pro Gly Pro Thr Gly Ala Ala Ser Ile Val Pro Ser Val Pro Gly Met
                290                 295                 300

Ala Leu Asp Leu Ser Gln Ile Pro Thr Lys Glu Leu Asp Arg Phe Ile
305                 310                 315                 320

Gln Asp His Leu Lys Pro Ser Pro Gln Phe Gln Glu Gln Val Lys Lys
                325                 330                 335

Ala Ile Asp Ile Ile Leu Arg Cys Leu His Glu Asn Cys Val His Lys
                340                 345                 350

Ala Ser Arg Val Ser Lys Gly Gly Ser Phe Gly Arg Gly Thr Asp Leu
                355                 360                 365

Arg Asp Gly Cys Asp Val Glu Leu Ile Ile Phe Leu Asn Cys Phe Thr
    370                 375                 380

Asp Tyr Lys Asp Gln Gly Pro Arg Arg Ala Glu Ile Leu Asp Glu Met
385                 390                 395                 400

Arg Ala Gln Leu Glu Ser Trp Trp Gln Asp Val Pro Ser Leu Ser
                405                 410                 415

Leu Gln Phe Pro Glu Gln Asn Val Pro Glu Ala Leu Gln Phe Gln Leu
                420                 425                 430

Val Ser Thr Ala Leu Lys Ser Trp Thr Asp Val Ser Leu Leu Pro Ala
        435                 440                 445

Phe Asp Ala Val Gly Gln Leu Ser Ser Gly Thr Lys Pro Asn Pro Gln
    450                 455                 460

Val Tyr Ser Arg Leu Leu Thr Ser Gly Cys Gln Glu Gly Glu His Lys
465                 470                 475                 480

Ala Cys Phe Ala Glu Leu Arg Arg Asn Phe Met Asn Ile Arg Pro Val
                485                 490                 495

Lys Leu Lys Asn Leu Ile Leu Leu Val Lys His Trp Tyr Arg Gln Val
                500                 505                 510

Ala Ala Gln Asn Lys Gly Lys Gly Pro Ala Pro Ala Ser Leu Pro Pro
    515                 520                 525

Ala Tyr Ala Leu Glu Leu Leu Thr Ile Phe Ala Trp Glu Gln Gly Cys
    530                 535                 540
```

-continued

```
Arg Gln Asp Cys Phe Asn Met Ala Gln Gly Phe Arg Thr Val Leu Gly
545                 550                 555                 560

Leu Val Gln Gln His Gln Leu Cys Val Tyr Trp Thr Val Asn Tyr
            565                 570                 575

Ser Thr Glu Asp Pro Ala Met Arg Met His Leu Leu Gly Gln Leu Arg
            580                 585                 590

Lys Pro Arg Pro Leu Val Leu Asp Pro Ala Asp Pro Thr Trp Asn Val
            595                 600                 605

Gly His Gly Ser Trp Glu Leu Ala Gln Glu Ala Ala Leu Gly
610                 615                 620

Met Gln Ala Cys Phe Leu Ser Arg Asp Gly Thr Ser Val Gln Pro Trp
625                 630                 635                 640

Asp Val Met Pro Ala Leu Leu Tyr Gln Thr Pro Ala Gly Asp Leu Asp
                645                 650                 655

Lys Phe Ile Ser Glu Phe Leu Gln Pro Asn Arg Gln Phe Leu Ala Gln
                660                 665                 670

Val Asn Lys Ala Val Asp Thr Ile Cys Ser Phe Leu Lys Glu Asn Cys
                675                 680                 685

Phe Arg Asn Ser Pro Ile Lys Val Ile Lys Val Val Lys Gly Gly Ser
690                 695                 700

Ser Ala Lys Gly Thr Ala Leu Arg Gly Arg Ser Asp Ala Asp Leu Val
705                 710                 715                 720

Val Phe Leu Ser Cys Phe Ser Gln Phe Thr Glu Gln Gly Asn Lys Arg
                725                 730                 735

Ala Glu Ile Ile Ser Glu Ile Arg Ala Gln Leu Glu Ala Cys Gln Gln
                740                 745                 750

Glu Arg Gln Phe Glu Val Lys Phe Glu Val Ser Lys Trp Glu Asn Pro
            755                 760                 765

Arg Val Leu Ser Phe Ser Leu Thr Ser Gln Thr Met Leu Asp Gln Ser
770                 775                 780

Val Asp Phe Asp Val Leu Pro Ala Phe Asp Ala Leu Gly Gln Leu Val
785                 790                 795                 800

Ser Gly Ser Arg Pro Ser Ser Gln Val Tyr Val Asp Leu Ile His Ser
                805                 810                 815

Tyr Ser Asn Ala Gly Glu Tyr Ser Thr Cys Phe Thr Glu Leu Gln Arg
            820                 825                 830

Asp Phe Ile Ile Ser Arg Pro Thr Lys Leu Lys Ser Leu Ile Arg Leu
        835                 840                 845

Val Lys His Trp Tyr Gln Gln Cys Thr Lys Ile Ser Lys Gly Arg Gly
850                 855                 860

Ser Leu Pro Pro Gln His Gly Leu Glu Leu Leu Thr Val Tyr Ala Trp
865                 870                 875                 880

Glu Gln Gly Gly Lys Asp Ser Gln Phe Asn Met Ala Glu Gly Phe Arg
                885                 890                 895

Thr Val Leu Glu Leu Val Thr Gln Tyr Arg Gln Leu Cys Ile Tyr Trp
            900                 905                 910

Thr Ile Asn Tyr Asn Ala Lys Asp Lys Thr Val Gly Asp Phe Leu Lys
        915                 920                 925

Gln Gln Leu Gln Lys Pro Arg Pro Ile Ile Leu Asp Pro Ala Asp Pro
930                 935                 940

Thr Gly Asn Leu Gly His Asn Ala Arg Trp Asp Leu Leu Ala Lys Glu
945                 950                 955                 960

Ala Ala Ala Cys Thr Ser Ala Leu Cys Cys Met Gly Arg Asn Gly Ile
```

```
                    965              970             975
Pro Ile Gln Pro Trp Pro Val Lys Ala Ala Val
            980             985

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
cttttcagca gtgcatgtgg                                                    20

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
ttcaatgcgt tttgctttaa ttt                                                23

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
cgtcttggaa ctggtcatca                                                    20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ggcacctgct gtggtttatt                                                    20
```